US007405299B2

(12) United States Patent
Beight et al.

(10) Patent No.: US 7,405,299 B2
(45) Date of Patent: Jul. 29, 2008

(54) COMPOUNDS AS PHARMACEUTICAL AGENTS

(75) Inventors: Douglas Wade Beight, Frankfort, IN (US); Timothy Paul Burkholder, Carmel, IN (US); Todd Vincent Decollo, Noblesville, IN (US); Alexander Glenn Godfrey, Mooresville, IN (US); Charles Raymond Heap, West Sand Lake, NY (US); Chi-Hsin Richard King, Slingerlands, NY (US); Hong-Yu Li, Zionsville, IN (US); William Thomas McMillen, McCordsville, IN (US); Jason Scott Sawyer, Indianapolis, IN (US); Yan Wang, Carmel, IN (US); Clive Gideon Diefenbacher, Greenwood, IN (US); Thomas Albert Engler, Indianapolis, IN (US); Sushant Malhotra, Indianapolis, IN (US); Sreenivasa Reedy Mundla, Westfield, IN (US)

(73) Assignee: Eli Lilly and Company, Indianapolis, IN (US)

( * ) Notice: Subject to any disclaimer, the term of this patent is extended or adjusted under 35 U.S.C. 154(b) by 330 days.

(21) Appl. No.: 10/535,381

(22) PCT Filed: Nov. 24, 2003

(86) PCT No.: PCT/US03/35969

§ 371 (c)(1),
(2), (4) Date: May 16, 2005

(87) PCT Pub. No.: WO2004/050659

PCT Pub. Date: Jun. 17, 2004

(65) Prior Publication Data

US 2006/0058295 A1    Mar. 16, 2006

(51) Int. Cl.
*C07D 241/36*   (2006.01)
*C07D 217/00*   (2006.01)
*C07D 401/00*   (2006.01)

(52) U.S. Cl. .................. 544/353; 546/139; 546/275.7
(58) Field of Classification Search .............. 546/275.7, 546/121, 139; 540/579, 470; 544/353
See application file for complete search history.

(56) References Cited

U.S. PATENT DOCUMENTS

| 7,087,626 B2* | 8/2006 | Beight et al. ............... 514/338 |
| 2006/0040983 A1* | 2/2006 | Beight et al. ............... 514/314 |
| 2006/0079680 A1* | 4/2006 | Sawyer ....................... 540/579 |

FOREIGN PATENT DOCUMENTS

| WO | WO 02 062787 | 8/2002 |
| WO | WO 02 062794 | 8/2002 |
| WO | WO 02 066462 | 8/2002 |
| WO | 2002094833 | * 11/2002 |
| WO | WO 02 094833 | 11/2002 |

OTHER PUBLICATIONS

Freshney (Culture of Animal Cells, A Manual of Basic Technique, Alan R. Liss, Inc., 1983, New York, pp. 1-6.*
Dermer (Bio/Technology, 1994, 12:320).*

* cited by examiner

*Primary Examiner*—D. Margaret Seaman
*Assistant Examiner*—Niloofar Rahmani
(74) *Attorney, Agent, or Firm*—Danica Hostettler; Tina M. Tucker

(57) ABSTRACT

The current invention relates to compounds of the formula: (Ia) and the pharmaceutically acceptable salts thereof and their use as TGF-beta signal transduction inhibitors for treating cancer and other diseases in a patient in need thereof by administration of said compounds.

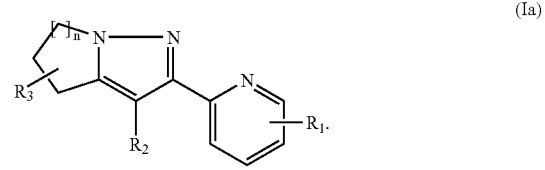

(Ia)

1 Claim, No Drawings

COMPOUNDS AS PHARMACEUTICAL AGENTS

The invention relates to new compounds and their use as pharmaceutical agents, in particular their use as TGF-beta signal transduction inhibitors.

BACKGROUND OF THE INVENTION

The transforming growth factor-beta (TGF-beta) ("TGF-β3") polypeptides influence growth, differentiation, and gene expression in many cell types. The first polypeptide of this family that was characterized, TGF-β1, has two identical 112 amino acid subunits that are covalently linked. TGF-β3, is a highly conserved protein with only a single amino acid difference distinguishing humans from mice. There are two other members of the TGF-β3 gene family that are expressed in mammals. TGF-β2 is 71% homologous to TGF-β1 (de Martin, et al. (1987) EMBO J. 6:3673-3677), whereas TGF-β3 is 80% homologous to TGF-β1 (Derynck, et al. (1988) EMBO J. 7:3737-3743). There are at least three different extracellular TGF-β receptors, Type I, II and III that are involved in the biological functions of TGF-β1, -β2 and -β3 (For reviews, see Derynck (1994) TIBS 19:548-553 and Massague (1990) Ann. Rev. Cell Biol. 6:597-641). The Type I and Type II receptors are transmembrane serine/threonine kinases that in the presence of TGF-β form a heteromeric signaling complex (Wrana, et al (1992) Cell 71: 1003-1014).

The mechanism of activation of the heteromeric signaling complex at the cell surface has been elucidated (Wrana, et al. (1994) Nature 370: 341-347). TGF-β3 first binds the type II receptor that is a constitutively active transmembrane serine/threonine kinase. The type I receptor is subsequently recruited into the complex, phosphorylated at the GS domain and activated to phosphorylate downstream signaling components (e.g. Smad proteins) to initiate the intracellular signaling cascade. A constitutively active type I receptor (T204D mutant) has been shown to effectively transduce TGF-β responses, thus bypassing the requirement for TGF-β and the type II receptor (Wieser, et al. (1995) EMBO J. 14: 2199-2208). Although no signaling function has been discovered for the type III receptor, it does increase the affinity of TGF-β2 for the type II receptor making it essentially equipotent with TGF-β1 and TGF-β3 (Lopez-Casillas, et al. (1993) Cell 73: 1435-1444).

Vascular endothelial cells lack the Type III receptor. Instead endothelial cells express a structurally related protein called endoglin (Cheifetz, et al. (1992) J. Biol. Chem. 267: 19027-19030), which only binds TGF-β1 and TGF-β3 with high affinity. Thus, the relative potency of the TGF-β's reflects the type of receptors expressed in a cell and organ system. In addition to the regulation of the components in the multi-factorial signaling pathway, the distribution of the synthesis of TGF-β polypeptides also affects physiological function. The distribution of TGF-β2 and TGF-β3 is more limited Derynck, et al. (1988) EMBO J. 7:3737-3743) than TGF-β1, e.g., TGF-β3 is limited to tissues of mesenchymal origin, whereas TGF-β1 is present in both tissues of mesenchymal and epithelial origin.

TGF-β1 is a multifunctional cytokine critical for tissue repair. High concentrations of TGF-β1 are delivered to the site of injury by platelet granules (Assoian and Sporn (1986) J. Cell Biol. 102:1217-1223). TGF-β1 initiates a series of events that promote healing including chemo taxis of cells such as leukocytes, monocytes and fibroblasts, and regulation of growth factors and cytokines involved in angiogenesis, cell division associated with tissue repair and inflammatory responses. TGF-β1 also stimulates the synthesis of extracellular matrix components (Roberts, et al. (1986) Proc. Natl. Acad. Sci. USA 83:4167-4171; Sporn, et al. (1983) Science 219:1329-1330; Massague (1987) Cell 49:437-438) and most importantly for understanding the pathophysiology of TGF-β1, TGF-β1 autoregulates its own synthesis (Kim, et al. (1989) J. Biol. Chem. 264:7041-7045).

The compounds disclosed herein may also exhibit other kinase activity, such as p38 kinase inhibition and/or KDR (VEGFR2) kinase inhibition. Assays to determine such kinase activity are known in the art and one skilled in the art would be able to test the disclosed compounds for such activity.

The compounds disclosed and claimed in this patent application are generally related to compounds disclosed and claimed in PCT patent application number PCT/US002/11884, filed 13 May 2002, which claims priority from U.S. patent application U.S. Ser. No. 60/293,464, filed 24 May 2001, and is herein incorporated by reference.

SUMMARY OF THE INVENTION

A compound of the formula:

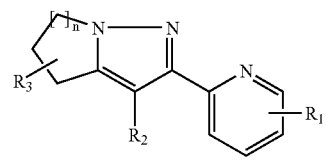

Formula Ia wherein n is 1-4;

$R_1$ may be one or more optional substituents selected from the group consisting of: (C1-C6)alkyl, (C2-C6)alkenyl, (C2-C6)alkynyl, (C1-C6)alkoxy, (C2-C6)alkenyloxy, (C2-C6)alkynyloxy, (C1-C6)alkylthio, (C1-C6)alkylsulphinyl, (C1-C6)alkylsulphonyl, ($C_1$-C6)alkylamino, di-[(C1-C6)alkyl]amino, (C1-C6)alkoxycarbonyl, N-(C1-C6)alkylcarbamoyl, N,N-di-[(C1-C6)alkyl]carbamoyl, (C2-C6)alkanoyl, (C2-C6)alkanoyloxy, (C2-C6)alkanoylamino, N-(C1-C6)alkyl-(C2-C6)alkanoylamino, (C3-C6)alkenoylamino, N-(C1-C6)alkyl-(C3-C6)alkenoylamino, (C3-C6)alkynoylamino, N-(C1-C6)alkyl-(C3-C6)alkynoylamino, N-(C1-C6)alkylsulphamoyl, N,N-di-[($C_1$-C6)alkyl]sulphamoyl, (C1-C6)alkanesulphonylamino, N-(C1-C6)alkyl-(C1-C6)alkanesulphonylamino, carboxamide, ethylene, thiophenyl, aminophenyl, trifluoromethyl, halo, trifluoromethoxy, hydroxymethyl, N-pyrrolidino, N-morpholino, phenylthio, (C1-C4)dialkylaminomethyl, methoxyphenyl, amino, hydroxy, carboxyl, phenyl, arylalky;

$R_2$ is selected from the group comprising unsubstituted or substituted thiophene; unsubstituted or substituted oxazole; unsubstituted or substituted pyrazine; unsubstituted or substituted pyrido[2,3-b]pyrazine; unsubstituted or substituted furan; unsubstituted or substituted imidazo[1,2-a]pyridine; unsubstituted or substituted benzoimidazole; unsubstituted or substituted quinoxaline; unsubstituted or substituted quinoxaline-2-one; unsubstituted or substituted isoquinoline; unsubstituted or substituted benzothiazole; unsubstituted or substituted indole; unsubstituted or substituted imidazo[4,5-b]pyridine; unsubstituted or substituted imidazo[4,5-c]pyridine; unsubstituted or substituted oxazolo[4,5-b]pyridine; unsubstituted or substituted dihydrobenzofuran; unsubstituted or substituted benzofuran; unsubstituted or substituted benzo[2,1,3]thiadiazole; unsubstituted or substituted benzo[1,2,5]thiadiazole; unsubstituted or substituted pyrazolo[1,5-a]pyrimidine; unsubstituted or substituted 3,4-dihydro-2H-benzo[b][1,4]dioxepine; unsubstituted or substituted [1,5]naphthyridine; unsubstituted or substituted [1,6]naphthyridine; or unsubstituted or substituted [1,8]naphthyridine;

wherein the substitution may independently be one or more of the following: (C1-C6)alkyl; (C1-C6)alkoxy; halogen; hydroxy; nitro; amino;

phenyl or substituted phenyl, wherein the phenyl may independently be substituted by one or two of the following: halogen, (C1-C6)alkyl, (C1-C6)alkoxy, nitro, amino, or hydroxy;
—$(CH_2)_m R^8$;
—$(CH_2)_o(O)R^9$;
—$(CH_2)_o C(O)$morpholine;
—$C(O)R^6$;
—$C(O)OR^4$;
—$C(O)NR^4R^5$;
—$C(O)NR^4(CH_2)_o NR_4 R^5$;
—$NR^4$(C1-C9)alkyl;
—$NR^4 C(O)(CH_2)_m CH_3$
—$NR^4 C(O)(CH_2)_o NR^4 R^5$;
—$O(CH_2)_o R^7$;
or —$OC(O)R^4$;

wherein
m is 0, 1, 2 or 3;
o is 1, 2 or 3;
$R^4$ and $R^5$ are each independently hydrogen or (C1-C6)alkyl;
$R^6$ is hydrogen, (C1-C6)alkyl or —$NR^4R^5$;
$R^7$ is hydroxy, cyano, pyrrolidine or $NR^4R^5$;
$R_8$ is morpholine, hydroxy, pyrrolidine, tetrahydropyran, (C1-C6)alkyl or $NR_4R^5$;
$R^9$ is morpholine, pyrrolidine, tetrahydropyran, or (C1-C6) alkyl;
$R_3$ is hydrogen or (C1-C6)alkyl;

and the pharmaceutically acceptable salts thereof.

A more preferred embodiment of the invention are compounds of the formula:

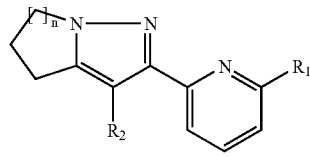

Formula II wherein n is 0 or 1;
$R_1$ is hydrogen or (C1-C4alkyl);
$R_2$ is selected from the group comprising unsubstituted or substituted thiophene; unsubstituted or substituted oxazole; unsubstituted or substituted pyrazine; unsubstituted or substituted furan; unsubstituted or substituted imidazo[1,2-a]pyridine; unsubstituted or substituted benzoimidazole; unsubstituted or substituted quinoxaline; unsubstituted or substituted isoquinoline; unsubstituted or substituted benzothiazole; unsubstituted or substituted indole; unsubstituted or substituted imidazo[4,5-b]pyridine; unsubstituted or substituted imidazo[4,5-c]pyridine; unsubstituted or substituted oxazolo[4,5-b]pyridine; unsubstituted or substituted dihydrobenzofuran; unsubstituted or substituted benzofuran; unsubstituted or substituted benzo[2,1,3]thiadiazole; unsubstituted or substituted benzo[1,2,5]thiadiazole; unsubstituted or substituted pyrazolo[1,5-a]pyrimidine; unsubstituted or substituted 3,4-dihydro-2H-benzo[b][1,4]dioxepine; unsubstituted or substituted [1,5]naphthyridine; unsubstituted or substituted [1,6]naphthyridine; or unsubstituted or substituted [1,8]naphthyridine;

wherein the substitution may independently be one or more of the following: (C1-C6)alkyl; (C1-C6)alkoxy; halogen; hydroxy; nitro; amino;

phenyl or substituted phenyl, wherein the phenyl is substituted by one or two halogens;
—$(CH_2)_m R^8$;
—$(CH_2)_o(O)R^9$;
$(CH_2)_o C(O)$morpholine;
—$C(O)R^6$;
—$C(O)OR^4$;
—$C(O)NR^4R^5$;
—$C(O)NR^4(CH_2)_o NR_4 R^5$;
—$NR^4$(C1-C9)alkyl;
—$NR^4 C(O)(CH_2)_m CH_3$
—$NR^4 C(O)(CH_2)_o NR^4 R^5$;
—$O(CH_2)_o R^7$;
or —$OC(O)R^4$;

wherein
m is 0, 1, 2 or 3;
o is 1, 2 or 3;
$R^4$ and $R^5$ are each independently hydrogen or (C1-C6)alkyl;
$R^6$ is hydrogen, (C1-C6)alkyl or —$NR_4R_5$;
$R^7$ is hydroxy, cyano, pyrrolidine or $NR^4R^5$;
$R^8$ is morpholine, hydroxy, pyrrolidine, tetrahydropyran, (C1-C6)alkyl or $NR^4R^5$;
$R^9$ is morpholine, pyrrolidine, tetrahydropyran, or (C1-C6) alkyl;

and the pharmaceutically acceptable salts thereof.

The disclosed invention also relates to compounds of the formula:

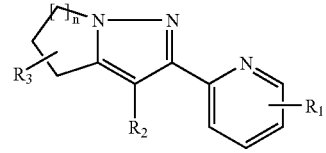

Formula I wherein n is 1-4;
$R_1$ may be one or more optional substituents selected from the group consisting of: (C1-C6)alkyl, (C2-C6)alkenyl, (C2-C6)alkynyl, (C1-C6)alkoxy, (C2-C6)alkenyloxy, (C2-C6)alkynyloxy, (C1-C6)alkylthio, (C1-C6)alkylsulphinyl, (C1-C6)alkylsulphonyl, (C1-C6)alkylamino, di-[(C1-C6)alkyl]amino, (C1-C6)alkoxycarbonyl, N-(C1-C6)alkylcarbamoyl, N,N-di-[(C1-C6)alkyl]carbamoyl, (C2-C6)alkanoyl, (C2-C6)alkanoyloxy, (C2-C6)alkanoylamino, N-(C1-C6)alkyl-(C2-C6)alkanoylamino, (C3-C6)alkenoylamino, N-(C1-C6)alkyl-(C3-C6)alkenoylamino, (C3-C6)alkynoylamino, N-(C1-C6)alkyl-(C3-C6)alkynoylamino, N-(C1-C6)alkylsulphamoyl, N,N-di-[($C_1$-C6)alkyl]sulphamoyl, (C1-C6)alkanesulphonylamino, N-(C1-C6)alkyl-(C1-C6)alkanesulphonylamino, carboxamide, ethylene, thiophenyl, aminophenyl, trifluoromethyl, halo, trifluoromethoxy, hydroxymethyl, N-pyrrolidino, N-morpholino, phenylthio, (C1-C4)dialkylaminomethyl, methoxyphenyl, amino, hydroxy, carboxyl, phenyl, arylalkyl;

$R_2$ is selected from the group comprising oxazole; benzo[2,1,3]thiadiazole; quinoxaline; 1H-imidazo[4,5-c]pyridine; imidazo[1,2-a]pyridine; indole; pyrazine; dihydrobenzofuran; furan; thiophene; isoquinoline; benzofuran; benzothiazole; 3,4-dihydro-2H-benzo[b][1,4]dioxepine; 1H-imidazo[4,5-b]pyridine; pyrazolo[1,5-a]pyrimidine; oxazolo[4,5-b]pyridine; 1H-benzoimidazole; [1,8]naphthyridine; or [1,5]naphthyridine;

$R_3$ may be one or more optional substituents selected from the group consisting of (C1-C6 alkyl);

and the pharmaceutically acceptable salts thereof.

Preferred embodiments also include compounds wherein $R^2$ may be as follows. The numbers preceding the specified heterocycle indicate the point of attachment of the specified heterocycle:

a) substituted or unsubstituted 2, 5, 6 or 7-quinoxaline;
b) substituted or unsubstituted 7-quinoxaline-2-one;
c) substituted or unsubstituted 6 or 7-isoquinoline;
d) substituted or unsubstituted 5 or 6-benzothiazole;
e) substituted or unsubstituted 4 or 5-indole;
f) substituted or unsubstituted 5-(3,4)dihydrobenzofuran;
g) substituted or unsubstituted 2, 3, 5 or 7-benzofuran;
h) substituted or unsubstituted 3, 5 or 6-pyrazolo[1,5-a]pyrimidine;
i) substituted or unsubstituted 2 or 3-[1,5]naphthyridine;
j) substituted or unsubstituted 4 or 8-[1,6]naphthyridine;
k) substituted or unsubstituted 5-oxazole;
l) substituted or unsubstituted 4 or 5-benzo[1,2,5]thiadiazole;
m) substituted or unsubstituted 2-pyrazine;
n) substituted or unsubstituted 7-pyrido[2,3-b]pyrazine;
o) substituted or unsubstituted 3-thiophene;
p) substituted or unsubstiued 3-furan;
q) substituted or unsubstituted 2-1H-imidazo[4,5-b]pyridine;
r) substituted or unsubstituted 6-imidazo[1,2-a]pyridine;
s) substituted or unsubstituted 5,6-1H-benzoimidazole;
t) substituted or unsubstituted 2-oxazolo[4,5-b]pyridine; or
u) substituted or unsubstituted 7-3,4-dihydro-2H-benzo[b][1,4]dioxepine.

Some preferred substituents include (C1-C4) alkyl; (C1-C4 alkoxy); halogen; —O(CH$_2$)$_m$NR$^4$R$^5$; —C(O)NR$^4$R$^5$; —O(CH$_2$)$_m$OH; NR$^4$R$_5$; —OC(O)(C1-C4)alkyl; —C(O)OR$^4$; or —C(O)NH(CH$_2$)$_m$NR$^4$R$^5$.

More preferred embodiments of the invention include the following:

Compounds according to the formula:

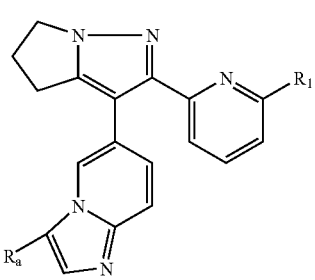

Formula III wherein:
$R_1$ is hydrogen or methyl;

$R_4$ is hydrogen; —CH$_2$ N-morpholino; —CH$_2$C(O)N-morpolino; —C(O)OCH$_2$CH$_3$; —C(O)NH(CH$_2$)$_2$N(CH$_3$)$_2$; —NHCH(CH$_2$)$_2$CH$_2$CH(CH$_2$)$_2$CH$_3$; —NHC(O)CH$_3$; —C(O)NH$_2$; or 4-chlorophenyl;

and the pharmaceutically acceptable salts thereof.

Other preferred embodiments of the invention include the following:

Compounds of the formula:

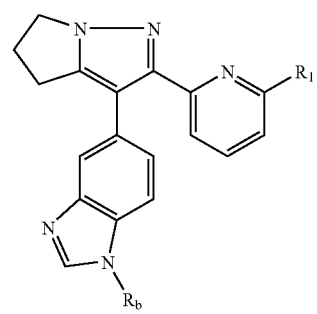

Formula IV wherein:
$R_1$ is hydrogen or methyl;
$R_b$ is hydrogen; methyl; or —(CH$_2$)$_3$O-tetrahydropyran; and the pharmaceutically acceptable salts thereof.

Also compounds according to the formula:

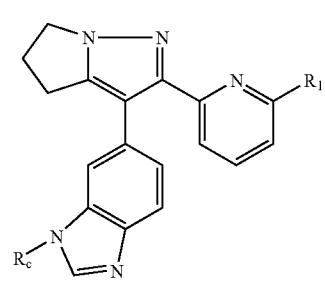

Formula V wherein:
$R_1$ is hydrogen or methyl; & is hydrogen; -methyl; —(CH$_2$)$_3$OH; —(CH$_2$)$_3$N(CH$_3$)$_2$; —(CH$_2$)$_3$N(CH$_2$CH$_3$)$_2$; or —(CH$_2$)X, wherein X is either N-morpholine, N-pyrrolidine or N-piperidine; and the pharmaceutically acceptable salts thereof.

DETAILED DESCRIPTION OF THE INVENTION

The term "effective amount" as used in "an effective amount of a compound of Formula I," for example, refers to an amount of a compound of the present invention that is capable of inhibiting TGF beta.

The general chemical terms used herein have their usual meanings. For example, as used herein, the term "C$_1$-C$_4$ alkyl", alone or in combination, denotes a straight-chain or branched-chain C$_1$-C$_4$ alkyl group consisting of carbon and hydrogen atoms, examples of which are methyl, ethyl, propyl, isopropyl, butyl, sec-butyl, tert-butyl, and the like.

The term "C$_1$-C$_4$ alkoxy", alone or in combination, denotes an alkyl group as defined earlier, which is attached via an oxygen atom, such as, for example, methoxy, ethoxy, propoxy, isopropoxy, butoxy, tert-butoxy, and the like. The term "$C_1$-$C_4$ alkylthio", alone or in combination, denotes an alkyl group as defined earlier and is attached via a sulfur atom, and includes methylthio, ethylthio, isobutylthio, and the like.

As used herein, the term "halo" or "halogen" represents fluorine, chlorine, bromine, or iodine. The term "hydroxy," alone or in combination, represents an —H moiety. The term "carboxy" or "carboxyl" refers to a carboxylic acid. The term "carboxamide" refers to a carbonyl substituted with an —$NH_2$ moiety. The term "oxo" refers to a carbonyl group.

As used herein, the term "aryl" represents a substituted or unsubstituted phenyl or naphthyl. Aryl may be optionally substituted with one or more groups independently selected from hydroxy, carboxy, $C_1$-$C_6$ alkoxy, $C_1$-$C_6$ alkyl, halogen, carboxamide, trifluoromethyl, hydroxymethyl, and hydroxy ($C_1$-$C_4$)alkyl.

As used herein, the term "$C_1$-$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$-$C_6$ alkyl" includes within its definition the terms "$C_1$-$C_4$ alkyl" and "$C_1$-$C_3$ alkyl."

As used herein, the term "$C_1$-$C_9$ alkyl" refers to straight or branched, monovalent, saturated aliphatic chains of 1 to 9 carbon atoms and includes, but is not limited to, methyl, ethyl, propyl, isopropyl, butyl, isobutyl, t-butyl, pentyl, isopentyl, and hexyl, etc.

"$C_1$-$C_6$ alkenyl" refers to a straight or branched, divalent, unsaturated aliphatic chain of 1 to 6 carbon atoms and includes, but is not limited to, methylenyl, ethylenyl, propylenyl, isopropylenyl, butylenyl, isobutylenyl, t-butylenyl, pentylenyl, isopentylenyl, hexylenyl.

"$C_1$-$C_6$ alkoxycarbonyl" represents a straight or branched $C_1$-$C_6$ alkoxy chain, as defined above, that is attached via the oxygen atom to a carbonyl moiety. Typical $C_1$-$C_6$ alkoxycarbonyl groups include methoxycarbonyl, ethoxycarbonyl, propoxycarbonyl, isopropoxycarbonyl, butoxycarbonyl, t-butoxycarbonyl and the like.

The term "di[(C1-C6 alkyl)]amino" refers to a group of the formula:

wherein each R group independently represents a "$C_1$-$C_6$ alkyl" group, as defined above.

As used herein, the term "heteroaryl" means an aryl moiety, which contains 1-5 heteroatoms selected from O, S, and N. Examples of heteroaryl groups include pyrrolyl, pyrazolyl, pyranyl, thiopyranyl, furanyl, imidazolyl, pyridyl, thiazolyl, triazinyl, phthalimidyl, indolyl, purinyl, and benzothiazolyl.

"Arylalkyl" refers to aryl groups attached to alkyl groups, preferably having 1 to 6 carbon atoms in the alkyl moiety and 6 to 10 carbon atoms in the aryl moiety. Such arylalkyl groups are exemplified by benzyl, phenethyl, and the like.

Unless otherwise constrained by the definition for arylalkyl, such arylalkyl groups can be optionally substituted with 1 to 5 substituents, more preferably 1 to 3 substituents, selected from the group consisting of halo, hydroxy, nitro, cyano, $C_1$-$C_6$ alkyl, $C_1$-$C_6$ alkoxy, di($C_1$-$C_6$ alkyl)amino, trifluoromethyl, trifluoromethoxy, carbamoyl, pyrrolidinyl, —S(O)$_m$—($C_1$-$C_6$ alkyl), and —S(O)$_m$-(phenyl), wherein m can be 0, 1, or 2. The arylalkyl groups may be optionally substituted on the aryl, moiety, the alkyl moiety, or both the aryl moiety and the alkyl moiety.

Abbreviations used herein include the following:
The term $Pd_2(dba)_3$ refers to tris(dibenzylideneacetone) dipalladium.
The term dppf refers to 1,1'-bis(diphenylphosphino) ferrocene.
The term DMAP=4-(N,N-dimethylamino)pyridine.
The term DMF refers to N,N-dimethylformamide.
The term DMSO refers to dimethylsulfoxide.
The term eq refers to equivalent.
The term ES refers to electron spray.
The term h refers to hour(s).
The term HPLC refers to high performance liquid chromatography.
The term L refers to liter.
The term min refers to minutes.
The term mL refers to milliliter.
The term mmol refers to millimole.
The term Mp refers to melting point.
The term MPLC refers to medium pressure liquid chromatography.
The term MS refers to mass spectrum.
The term THF refers to tetrahydrofaran.
The term THP refers to tetrahydropyran.
The term TLC refers to thin layer chromatography.
The term W refers to watts.

Compounds Exemplified in the Application Include the Following

It will be understood that the number preceding the compound name corresponds to the example wherein the compound is exemplified.

a) 2-(Pyridin-2-yl)-3-(thiophen-2-yl)-5,6-dihydro-4H-pyrrolo[1,2-b]pyrazole (Example 1)
b) 5-[2-(Pyridin-2-yl)-5,6-dihydro-4H-pyrrolo[1,2-b]pyrazol-3-yl]-1H-indole (Ex. 2)
c) 3-(2-Phenyl-oxazol-5-yl)-2-(pyridin-2-yl)-5,6-dihydro-4H-pyrrolo[1,2-b]pyrazole (Ex. 3)
d) 4-[2-(Pyridin-2-yl)-5,6-dihydro-4H-pyrrolo [1,2-b]pyrazol-3-yl]-benzo[2,1,3]thiadiazole (Ex. 4)
e) 5-[2-(Pyridin-2-yl)-5,6-dihydro-4H-pyrrolo[1,2-b]pyrazol-3-yl]benzo[2,1,3]thiadiazole (Ex. 5)
f) 6-[2-(Pyridin-2-yl)-5,6-dihydro-4H-pyrrolo[1,2-b]pyrazol-3-yl]-quinoxaline (Ex. 6)
g) 5-[2-(Pyridin-2-yl)-5,6-dihydro-4H-pyrrolo[1,2-b]pyrazol-3-yl]-quinoxaline (Ex. 7)
h) 2-[2-(Pyridin-2-yl)-5,6-dihydro-4H-pyrrolo [1,2-b]pyrazol-3-yl]-1H-imidazo[4,5-b]pyridine (Ex. 8)
i) 2-[2-(Pyridin-2-yl)-5,6-dihydro-4H-pyrrolo[1,2-b]pyrazol-3-yl]-1H-imidazo[4,5-c]pyridine (Ex. 9)
j) 2-[2-(Pyridin-2-yl)-5,6-dihydro-4H-pyrrolo[1,2-b]pyrazol-3-yl]-1H-benzoimidazole (Ex. 10)
k) 2-[2-(Pyridin-2-yl)-5,6-dihydro-4H-pyrrolo[1,2-b]pyrazol-3-yl]-oxazolo[4,5-b]pyridine (Ex. 11)
l) 2-Dimethylamino-N-[6-[2-(pyridin-2-yl)-5,6-dihydro-4H-pyrrolo[1,2-b]pyrazol-3-yl]-[1,8]naphthyridin-2-yl]-acetamide (Ex. 12)
m) 4-[2-(Pyridin-2-yl)-5,6-dihydro-4H-pyrrolo[1,2-b]pyrazol-3-yl]-[1,8]naphthyridine (Ex. 13)
n) 2-(Pyridin-2-yl)-3-(imidazo[1,2-a]pyridin-6-yl)-5,6-dihydro-4H-pyrrolo[1,2-b]pyrazole (Ex. 14)
o) 7-[2-(6-Methyl-pyridin-2-yl)-5,6-dihydro-4H-pyrrolo[1,2-b]pyrazol-3-yl]-isoquinoline (Ex. 15)
p) 4-[2-(Pyridin-2-yl)-5,6-dihydro-4H-pyrrolo[1,2-b]pyrazol-3-yl]-isoquinoline (Ex. 16)

q) 3-(4-Fluoro-benzofuran-7-yl)-2-(pyridin-2-yl)-5,6-dihydro-4H-pyrrolo[1,2-b]pyrazole (Ex. 17)
r) 2-Methyl-5-[2-(pyridin-2-yl)-5,6-dihydro-4H-pyrrolo[1,2-b]pyrazol-3-yl]-benzothiazole (Ex. 18)
s) 2-Methyl-5-[2-(6-methyl-pyridin-2-yl)-5,6-dihydro-4H-pyrrolo[1,2-b]pyrazol-3-yl]-benzothiazole (Ex. 19)
t) 3-(4-Fluoro-benzofuran-7-yl)-2-(6-methyl-pyridin-2-yl)-5,6-dihydro-4H-pyrrolo[1,2-b]pyrazole (Ex. 20)
u) 7-[2-(Pyridin-2-yl)-5,6-dihydro-4H-pyrrolo[1,2-b]pyrazol-3-yl]-isoquinoline (Ex. 21)
v) 1-Methyl-5-[2-(6-methyl-pyridin-2-yl)-5,6-dihydro-4H-pyrrolo[1,2-b]pyrazol-3-yl]-1H-indole (Ex. 22)
w) 1-Methyl-5-[2-(pyridin-2-yl)-5,6-dihydro-4H-pyrrolo[1,2-b]pyrazol-3-yl]-1H indole (Ex. 23)
x) 3-(Pyrazin-2-yl)-2-(pyridin-2-yl)-5,6-dihydro-4H-pyrrolo[1,2-b]pyrazole (Ex. 24)
y) 2-(6-Methyl-pyridin-2-yl)-3-(pyrazin-2-yl)-5,6-dihydro-4H-pyrrolo[1,2-b]pyrazole (Ex. 25)
z) 3-(2,3-Dihydro-benzofuran-5-yl)-2-(6-methyl-pyridin-2-yl)-5,6-dihydro-4H-pyrrolo[1,2-b]pyrazole (Ex. 26)
aa) 3-(Furan-3-yl-2)-(6-methyl-pyridin-2-yl)-5,6-dihydro-4H-pyrrolo[1,2-b]pyrazole (Ex. 27)
bb) 3-(Furan-3-yl)-2-(pyridin-2-yl)-5,6-dihydro-4H-pyrrolo[1,2-b]pyrazole (Ex. 28)
cc) 2-(6-Methyl-pyridin-2-yl)-3-(thiophen-3-yl)-5,6-dihydro-4H-pyrrolo[1,2-b]pyrazole (Ex. 29)
dd) 3-(Benzofuran-5-yl)-2-(6-methyl-pyridin-2-yl)-5,6-dihydro-4H-pyrrolo[1,2-b]pyrazole (Ex. 30)
ee) 6-[2-(Pyridin-2-yl)-5,6-dihydro-4H-pyrrolo[1,2-b]pyrazol-3-yl]-pyrazolo[1,5-a]pyrimidine (Ex. 31)
ff) 3-(3,4-Dihydro-2H-benzo[b][1,4]dioxepin-7-yl)-2-(pyridin-2-yl)-5,6-dihydro-4H-pyrrolo[1,2-b]pyrazole (Ex. 32)
gg) 3-Morpholin-4-ylmethyl-6-[2-(pyridin-2-yl)-5,6-dihydro-4H-pyrrolo[1,2-b]pyrazol-3-yl]-imidazo[1,2-a]pyridine (Ex. 33)
hh) 1-Morpholin-4-yl-2-[6-(2-pyridin-2-yl-5,6-dihydro-4H-pyrrolo[1,2-b]pyrazol-3-yl)-imidazo[1,2-a]pyridin-3-yl]-ethanone (Ex. 34)
ii) 6-[2-(Pyridin-2-yl)-5,6-dihydro-4H-pyrrolo[1,2-b]pyrazol-3-yl]-imidazo[1,2-a]pyridine-3-carboxylic acid (Ex. 35)
jj) 6-[2-(Pyridin-2-yl)-4,5,6,7-tetrahydro-pyrazolo[1,5-a]pyridin-3-yl]-imidazo[1,2-a]pyridine (Ex. 36)
kk) 1-Morpholin-4-yl-2-[6-(2-pyridin-2-yl)-5,6-dihydro-4H-pyrrolo[1,2-b]pyrazol-3-yl)-imidazo[1,2-a]pyridin-2-yl]-ethanone (Ex. 37)
ll) 6-[2-(Pyridin-2-yl)-5,6-dihydro-4H-pyrrolo[1,2-b]pyrazol-3-yl]-imidazo[1,2-a]pyridine-3-carboxylic acid (2-dimethylamino-ethyl)-amide (Ex. 38)
mm) 6-[2-(6-Methyl-pyridin-2-yl)-5,6-dihydro-4H-pyrrolo[1,2-b]pyrazol-3-yl]-imidazo[1,2-a]pyridine-2-carboxylic acid ethyl ester (Ex. 39)
nn) 6-[2-(6-Methyl-pyridin-2-yl)-5,6-dihydro-4H-pyrrolo[1,2-b]pyrazol-3-yl]-imidazo[1,2-a]pyridine-2-carboxylic acid amide (Ex. 40)
oo) 8-Fluoro-6-[2-(pyridin-2-yl)-5,6-dihydro-4H-pyrrolo[1,2-b]pyrazol-3-yl]-imidazo[1,2-a]pyridine (Ex. 41)
pp) [6-[2-(Pyridin-2-yl)-5,6-dihydro-4H-pyrrolo[1,2-b]pyrazol-3-yl]-imidazo[1,2-a]pyridin-3-yl]-(1,1,3,3-tetramethyl-butyl)-amine (Ex. 42)
qq) N-[6-[2-(Pyridin-2-yl)-5,6-dihydro-4H-pyrrolo[1,2-b]pyrazol-3-yl]-imidazo[1,2-a]pyridin-3-yl]-acetamide (Ex. 43)
rr) 6-[2-(Pyridin-2-yl)-5,6-dihydro-4H-pyrrolo[1,2-b]pyrazol-3-yl]-imidazo[1,2-a]pyridine-3-carboxylic Acid Amide (Ex. 44)
ss) 6-[2-(6-Methyl-pyridin-2-yl)-5,6-dihydro-4H-pyrrolo[1,2-b]pyrazol-3-yl]-imidazo[1,2-a]pyridine-2-carboxylic Acid (2-Dimethylamino-ethyl)-amide (Ex. 45)
tt) 6-[2-(6-Methyl-pyridin-2-yl)-5,6-dihydro-4H-pyrrolo[1,2-b]pyrazol-3-yl]-imidazo[1,2-a]pyridine-3-carboxylic Acid Amide (Ex. 46)
uu) 7-[2-(Pyridin-2-yl)-5,6-dihydro-4H-pyrrolo[1,2-b]pyrazol-3-yl]-imidazo[1,2-a]pyridine (Ex. 47)
vv) 3-(4-Chloro-phenyl)-6-[2-(6-methyl-pyridin-2-yl)-5,6-dihydro-4H-pyrrolo[1,2-b)pyrazol-3-yl]-imidazo[1,2-a]pyridine (Ex. 48)
ww) 5-[2-(6-Methyl-pyridin-2-yl)-5,6-dihydro-4H-pyrrolo[1,2-b]pyrazol-3-yl]-1H-benzoimidazole (Ex. 49)
xx) 1-Methyl-6-[2-(6-methyl-pyridin-2-yl)-5,6-dihydro-4H-pyrrolo[1,2-b]pyrazol-3-yl]-1H-benzoimidazole (Ex. 50)
yy) 1-Methyl-6-[2-(pyridin-2-yl)-5,6-dihydro-4H-pyrrolo[1,2-b]pyrazol-3-yl]-1H-benzoimidazole (Ex. 51)
zz) 1-Methyl-5-[2-(pyridin-2-yl)-5,6-dihydro-4H-pyrrolo[1,2-b]pyrazol-3-yl]-1H-benzoimidazole (Ex. 52)
aaa) 1-Methyl-5-[2-(6-methyl-pyridin-2-yl)-5,6-dihydro-4H-pyrrolo[1,2-b]pyrazol-3-yl]-1H-benzoimidazole (Ex. 53)
bbb) 5-[2-(6-Methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole (Ex. 54)
ccc) 6-[2-(6-Methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole (Ex. 54)
ddd) 5-[2-(Pyridin-2-yl)-5,6-dihydro-4H-pyrrolo[1,2-b]pyrazol-3-yl]-1-[3-(tetrahydro-pyran-2-yloxy)-propyl]-1H-benzoimidazole (Ex. 55)
eee) 6-[2-(Pyridin-2-yl)-5,6-dihydro-4H-pyrrolo[1,2-b]pyrazol-3-yl]-1-[3-(tetrahydro-pyran-2-yloxy)-propyl]-1H-benzoimidazole (Ex. 55)
fff) 2-{7-[2-(6-Methyl-pyridin-2-yl)-5,6-dihydro-4H-pyrrolo[1,2-b]pyrazol-3-yl]-pyrido[2,3-b]pyrazin-2-yloxy}-ethanol (Ex. 55a)
ggg) 7-[2-(6-Methyl-pyridin-2-yl)-5,6-dihydro-4H-pyrrolo[1,2-b]pyrazol-3-yl]-1H-quinoxalin-2-one (Ex. 55b)
hhh) 3-[2-(6-Methyl-pyridin-2-yl)-5,6-dihydro-4H-pyrrolo[1,2-b]pyrazol-3-yl][1,5]naphthyridine (Ex. 55c)

iii) 3-[6-[2-(6-Methyl-pyridin-2-yl)-5,6-dihydro-4H-pyrrolo [1,2-b]pyrazol-3-yl]-benzoimidazol-1-yl]-propan-1-ol (Ex. 56)

jjj) 3-[6-[2-(Pyridin-2-yl)-5,6-dihydro-4H-pyrrolo[1,2-b] pyrazol-3-yl]-benzoimidazol-1-yl]-propan-1-ol (Ex. 57)

kkk) Methanesulfonic Acid 3-[6-[2-(6-Methyl-pyridin-2-yl)-5,6-dihydro-4H-pyrrolo[1,2-b]pyrazol-3-yl]-benzoimidazol-1-yl]-propyl Ester (Ex. 57a)

lll) Methanesulfonic acid 3-[6-[2-(pyridin-2-yl)-5,6-dihydro-4H-pyrrolo[1,2-b]pyrazol-3-yl]-benzoimidazol-1-yl]-propyl ester (Ex. 57b)

mmm) Dimethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine (Ex. 58)

nnn) Diethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine (Ex. 59)

ooo) 6-[2-(6-Methyl-pyridin-2-yl)-5,6-dihydro-4H-pyrrolo[1,2-b]pyrazol-3-yl]-1-(3-morpholin-4-yl-propyl)-1H-benzoimidazole (Ex. 60)

ppp) 6-[2-(6-Methyl-pyridin-2-yl)-5,6-dihydro-4H-pyrrolo[1,2-b]pyrazol-3-yl]-1-(3-pyrrolidin-1-yl-propyl)-1H-benzoimidazole (Ex. 61)

qqq) 6-[2-(6-Methyl-pyridin-2-yl)-5,6-dihydro-4H-pyrrolo[1,2-b]pyrazol-3-yl]-1-(3-piperidin-1-yl-propyl)-1H-benzoimidazole (Ex. 62)

rrr) 5-[2-(Pyridin-2-yl)-5,6-dihydro-4H-pyrrolo[1,2-b] pyrazol-3-yl]-1-H-benzoimidazole (Ex. 63)

sss) 6-[2-(6-Methyl-pyridin-2-yl)-5,6-dihydro-4H-pyrrolo[1,2-b]pyrazol-3-yl]-quinoxaline (Ex. 64)

ttt) 2-[2-(Pyridin-2-yl)-5,6-dihydro-4H-pyrrolo[1,2-b] pyrazol-3-yl]-quinoxaline (Ex. 65)

uuu) 2-[7-[2-(6-Methyl-pyridin-2-yl)-5,6-dihydro-4H-pyrrolo[1,2-b]pyrazol-3-yl]-quinoxalin-2-yloxy]-ethanol (Ex. 66)

vvv) 4-[2-(Pyridin-2-yl)-5,6-dihydro-4H-pyrrolo[1,2-b] pyrazol-3-yl]-[1,6]naphthyridine (Ex. 66a)

www) 6-[2-(6-Methyl-pyridin-2-yl)-5,6-dihydro-4H-pyrrolo[1,2-b]pyrazol-3-yl]-isoquinoline (Ex. 67)

xxx) 6-[2-(Pyridin-2-yl)-5,6-dihydro-4H-pyrrolo[1,2-b] pyrazol-3-yl]-benzothiazole (Ex. 68)

yyy) 2-[2-(Pyridin-2-yl)-5,6-dihydro-4H-pyrrolo[1,2-b] pyrazol-3-yl]-benzothiazole (Ex. 69)

zzz) 5-[2-(Pyridin-2-yl)-5,6-dihydro-4H-pyrrolo[1,2-b] pyrazol-3-yl]-benzothiazol-2-ylamine (Ex. 70)

aaaa) 4-[2-(Pyridin-2-yl)-5,6-dihydro-4H-pyrrolo[1,2-b] pyrazol-3-yl]-1H-indole (Ex. 71)

bbbb) 3-[2-(Pyridin-2-yl)-5,6-dihydro-4H-pyrrolo[1,2-b] pyrazol-3-yl]-1H-indole (Ex. 72)

cccc) 3-(2,3-Dihydro-benzofuran-5-yl)-2-(pyridin-2-yl)-5,6-dihydro-4H-pyrrolo[1,2-b]pyrazole (Ex. 73)

dddd) Acetic acid 5-[2-(6-methyl-pyridin-2-yl)-5,6-dihydro-4H-pyrrolo[1,2-b]pyrazol-3-yl]-benzofuran-3-yl ester (Ex. 74)

eeee) 3-(5-Methoxy-benzofuran-3-yl)-2-(6-methyl-pyridin-2-yl)-5,6-dihydro-4H-pyrrolo[1,2-b]pyrazole (Ex. 75)

ffff) 5-[2-(6-Methyl-pyridin-2-yl)-5,6-dihydro-4H-pyrrolo[1,2-b]pyrazol-3-yl]-benzofuran-2-carboxylic acid (Ex. 76)

gggg) 3-(Benzofuran-2-yl)-2-(6-methyl-pyridin-2-yl)-5, 6-dihydro-4H-pyrrolo[1,2-b]pyrazole (Ex. 77)

hhhh) 5-[2-(Pyridin-2-yl)-5,6-dihydro-4H-pyrrolo[1,2-b] pyrazol-3-yl]-pyrazolo[1,5-a]pyrimidine (Ex. 78)

iiii) 5-[2-(6-Methyl-pyridin-2-yl)-5,6-dihydro-4H-pyrrolo [1,2-b]pyrazol-3-yl]-pyrazolo[1,5-a]pyrimidine (Ex. 79)

jjjj) 5-[2-(Pyridin-2-yl)-4,5,6,7-tetrahydro-pyrazolo[1,5-a]pyridin-3-yl]-pyrazolo[1,5-a]pyrimidine (Ex. 80)

kkkk) 8-(2-Pyridin-2-yl-5,6-dihydro-4H-pyrrolo[1,2-b] pyrazol-3-yl)-[1,6]naphthyridine (Ex. 80a)

llll) 3-[2-(Pyridin-2-yl)-5,6-dihydro-4H-pyrrolo[1,2-b] pyrazol-3-yl)-pyrazolo[1,5-a]pyrimidine (Ex. 81)

mmmm) 2-[2-(Pyridin-2-yl)-5,6-dihydro-4H-pyrrolo[1,2-b]pyrazol-3-yl]-[1,5]naphthyridine (Ex. 82)

nnnn) 2-Chloro-7-[2-(6-methyl-pyridin-2-yl)-5,6-dihydro-4H-pyrrolo[1,2-b]pyrazol-3-yl]-quinoxaline (Ex. 83)

oooo) Dimethyl-(2-{7-[2-(6-methyl-pyridin-2-yl)-5,6-dihydro-4H-pyrrolo[1,2-b]pyrazol-3-yl]-quinoxalin-2-yloxy}-ethyl)-amine (Ex. 84)

pppp) Dimethyl-(2-{7-[2-(6-methyl-pyridin-2-yl)-5,6-dihydro-4H-pyrrolo[1,2-b]pyrazol-3-yl]-quinoxalin-2-yloxy}-propyl)-amine (Ex. 85)

qqqq) 7-[2-(6-Methyl-pyridin-2-yl)-5,6-dihydro-4H-pyrrolo[1,2-b]pyrazol-3-yl]-quinoxaline-2-carboxylic acid amide (Ex. 86)

The compounds exemplified above are merely representative of the invention and are not limiting in any fashion.

The compounds disclosed herein can be made according to the following schemes and examples. The examples should in no way be understood to be limiting in any way as to how the compounds may be made.

The skilled artisan will appreciate that the introduction of certain substituents will create asymmetry in the compounds of Formula (I), (Ia), (II), (III), (IV) and (V). The present invention contemplates all enantiomers and mixtures of enantiomers, including racemates. It is preferred that the compounds of the invention containing chiral centers are single enantiomers.

The compounds of the present invention can be prepared by a variety of procedures, some of which are illustrated in the Schemes below. It will be recognized by one of skill in the art that the individual Steps in the following schemes may be varied to provide the compounds of Formula (Ia). The particular order of Steps required to produce the compounds of Formula (Ia) is dependent upon the particular compound being synthesized, the starting compound, and the relative lability of the substituted moieties.

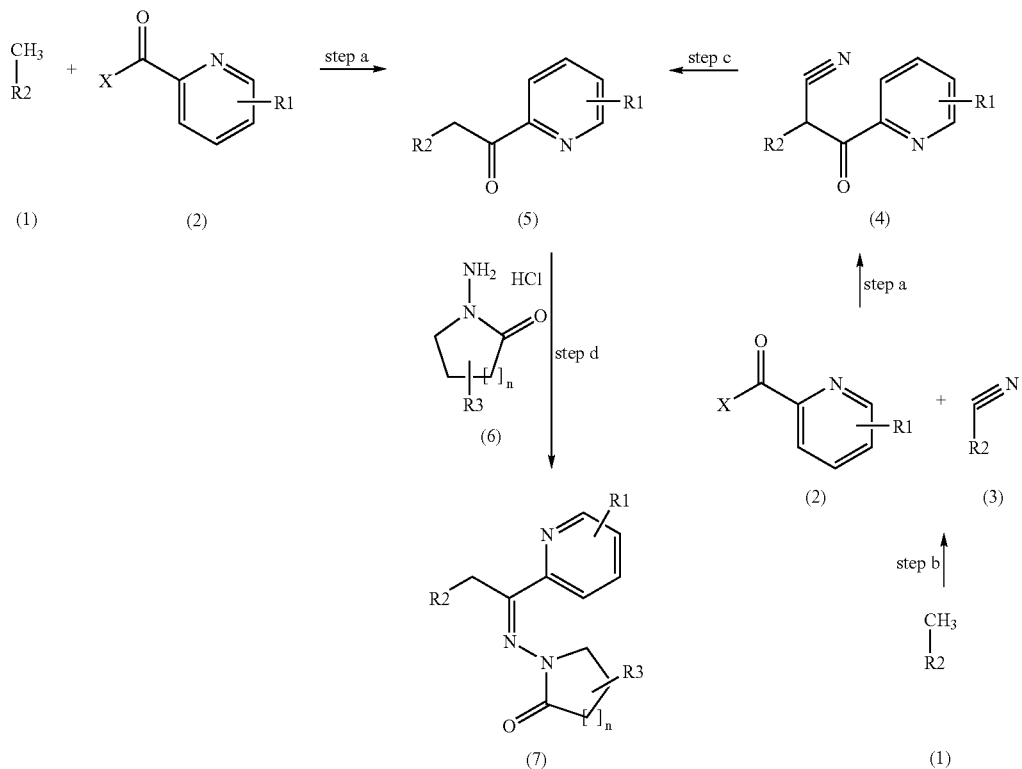

SCHEME I

Scheme I, step a, depicts an acylation of an appropriate aromatic and/or heteroaromatic compound of formula (1) and an appropriate carbonyl compound of formula (2) to give a compound of formula (5). The aromatic and/or heteroaromatic compounds of formula (1) are commercially available or can be produced by methods known in the art (*Chem. Pharm. Bull.* 1971, 1857). Compounds of formula (2) are commercially available or can be made as taught in PCT/US002/11884. The acylation of formula (1) requires that X, of formula (2), be a suitable leaving group, such as C1-C6 alkoxy, halo, C1-C6 thioether, or preferably disubstituted amino. The reaction is typically carried out in the presence of a suitable base, such as lithium diisopropylamide, potassium bis(trimethylsilyl)amide, lithium bis(trimethylsilyl)amide, sodium bis(trimethylsilyl)amide, sodium hydride, lithium hydride, potassium hydride, sodium alkoxides (sodium methoxide, or sodium ethoxide) or potassium alkoxides (potassium methoxide, or potassium ethoxide), or preferably potassium bis(trimethylsilyl)amide. Generally, the reaction is carried out in suitable solvents, such as tetrahydrofuran, toluene, or a combination of such, at temperatures of about −78° C. to ambient temperature. The product, formula (5), can be isolated and purified by techniques well known in the art, such as precipitation, filtration, extraction, evaporation, trituration, chromatography, and recrystallization. Another variation of the acylation, step a, is to use a nitrile compound of formula (3) in place of the aromatic- or heteroaromatic-methyl compounds of formula (1). The product, formula (4), can be transformed to formula (5) by hydrolysis of the nitrile group and then subsequent decarboxylation. Generally, a compound of formula (4) is dissolved in a hydrogen halide acid solution, preferably hydrogen chloride. The reaction is carried out at temperatures of about ambient to refluxing for 1 to 48 hours. This type of reaction is well known and appreciated in the art (Larock, R. C., *Comprehensive Organic Transformations*, copyright 1989, VCH, pp 993). Compounds of formula (3) can be acquired by treatment of an appropriately substituted aromatic- or heteroaromatic-methyl group with a halogenating reagent, such as N-halosuccinimides, preferably N-bromosuccinimide in a suitable solvent, preferably carbon tetrachloride and subsequently reacting the aromatic-halomethylene intermediate with a nitrile source, such as lithium cyanide, potassium cyanide, trimethylsilyl cyanide, or preferably sodium cyanide. The reaction is carried out in a suitable solvent such as water, tetrahydrofuran, N-methylpyrrolidin-2-one, dimethylsulfoxide or preferably N,N-dimethylformamide. The reaction is carried out at 0° C. to refluxing for 1 to 48 hours, as shown in step b, to afford the nitrile compounds of formula (3), (Larock, R. C., *Comprehensive Organic Transformations, copyright* 1989, VCH, pp 313; Eur. J. Org. Chem. 1999, 2315-2321).

In Scheme I, step d, compound of formula (5) is contacted to an appropriate compound of formula (6), this type of compound is known and appreciated in the art (Taylor, Edward C.; Haley, Neil F.; Clemens, Robert J., *J. Amer. Chem. Soc.*, 1981, 7743-7752), to give the compound of formula (7). Typically, the reaction is carried out in an appropriate solvent, such as acetic acid, ethanol, triethylamine, or preferably pyridine. The reaction is carried out at temperatures of about 60° C. to ambient for 4-24 hours. The products can be isolated and purified by techniques described above.

SCHEME II

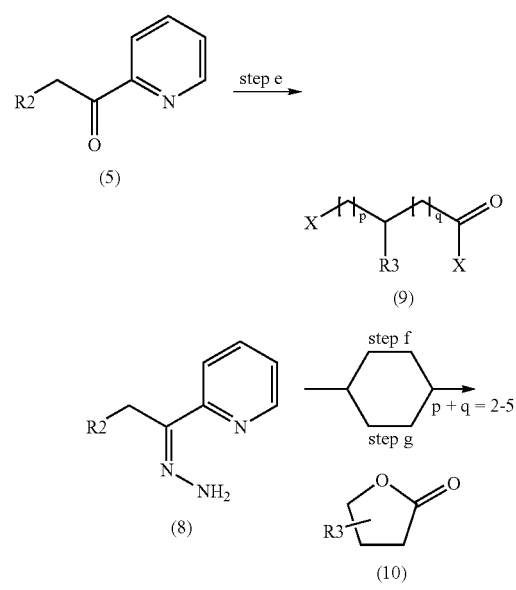

-continued

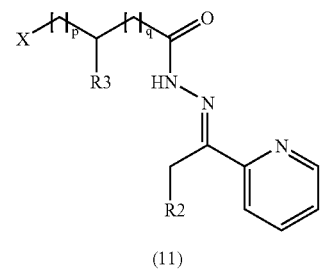

Scheme II, step e, depicts a ketone of formula (5) affording a hydrazone compound of formula (8). Typically the reaction is carried out with a suitable source of hydrazine, preferably hydrazine hydrate in an acidic solution consisting of an alcohol, such as methanol, ethanol, or propanol, and a hydrogen halo acid catalyst, preferably hydrogen chloride. The product can be isolated and purified by techniques described above. Compounds of formula (9) are commercially available. Step a previously described, transform the hydrazones of formula (8) to the hydrazides of formula (11), by acylation with compounds formula (9). The compound of formula (9) can be an appropriate carboxylic acid derivative, where X can be a leaving group previously described, preferably a halogen, most preferably a chloride, and where the sum of p and q can equal 2 or 5 carbons. The reaction is carried out in the presence of an acid scavenger such as pyridine or triethylamine. The reagents are combined, and products isolated and purified by techniques described above. The conversion of amines to amides by acylation is well known and appreciated in the art (Larock, R. C., *Comprehensive Organic Transformations, copyright* 1989, VCH, pp 979).

Scheme II, step g depicts ring opening of substituted lactones of formula (10) to afford hydrazones of formula (11). Typically, a compound of formula (8) is contacted with a suitable Lewis acid, preferably trimethyl aluminum followed by addition of a compound of formula (10) which can give the corresponding alcohol derivatives to be further transformed to give compound of formula (11).

SCHEME III

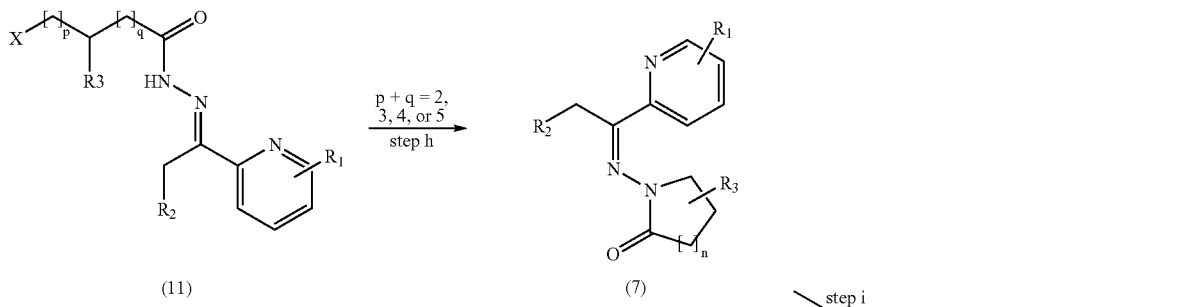

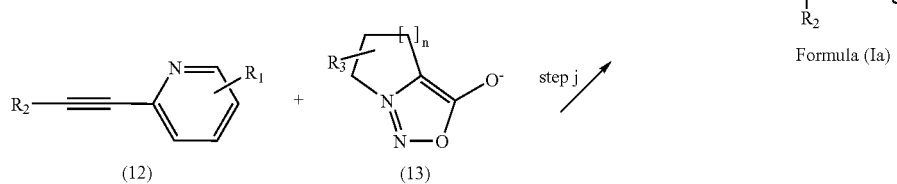

In Scheme III, step h depicts the cyclization of a compound of formula (II), where the R group(s) can be any group(s), previously defined as $R_1$, $R_2$ or $R_3$ of Formula (Ia). Typically, the appropriate compound of formula (11) is contacted to a suitable base such as lithium diisopropylamide, potassium bis(trimethylsilyl)amide, lithium bis(trimethylsilyl)amide, sodium bis(trimethylsilyl)amide, cesium carbonate, lithium hydride, potassium hydride, sodium alkoxides (sodium hydoxide, sodium methoxide, or sodium ethoxide) or potassium alkoxides (potassium hydroxide, potassium methoxide, or potassium ethoxide), or preferably sodium hydride. The reaction is carried out in a suitable solvent, such as tetrahydrofuran, N,N-dimethylformamide, N-methylpyrrolidin-2-one, dimethylsulfoxide, toluene, or preferably tetrahydrofaran, at temperatures of about 0 to 100° C. Step i depicts the cyclization of a compound of formula (7). Typically, the appropriate compound of formula (7) is contacted to a suitable base such as lithium diisopropylamide, potassium bis (trimethylsilyl)amide, lithium bis(trimethylsilyl)amide, sodium bis(trimethylsilyl)amide, sodium hydride, lithium hydride, potassium hydride, sodium alkoxides (sodium hydoxide, sodium methoxide, or sodium ethoxide) or potassium alkoxides (potassium hydroxide, potassium methoxide, or potassium ethoxide), or preferably cesium carbonate. The reaction is carried out in a suitable solvent, such as tetrahydrofuran, N,N-dimethylformamide, dimethylsulfoxide, toluene, or preferably N-methylpyrrolidin-2-one, at temperatures of about 0 to 100° C. The products can be isolated and purified by techniques well known in the art, such as precipitation, filtration, extraction, evaporation, trituration, chromatography, and recrystallization.

Another variation a skilled artisan would appreciate is Method B for the formation of Formula (I), in Scheme III, step j, which is known and appreciated in the art (Ranganathan, Darshan; Bamezai, Shakti, *Tetrahedron Lett.*, 1983, 1067-1070). For example, an alkyne (12) is reacted with a compound (13) in a suitable solvent, such as tetrahydrofuran, N,N-dimethylformamide, or toluene, preferably xylene at temperatures of about 0 to 150° C. The products can be isolated and purified by techniques described above.

SCHEME IV

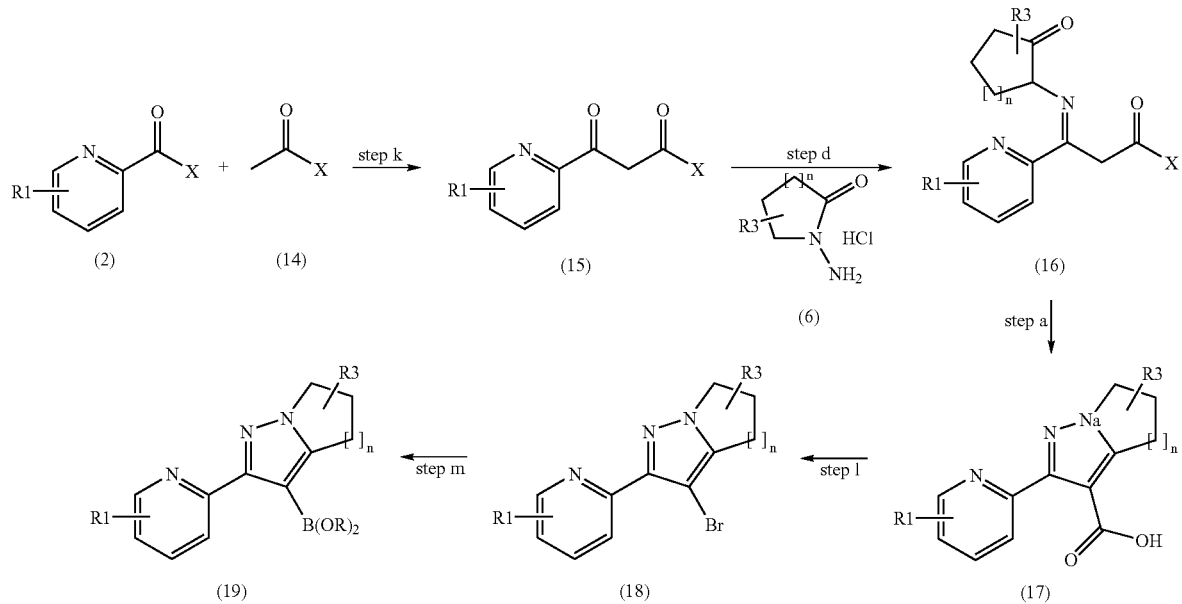

Another useful intermediate in the synthesis of compounds of Formula I is shown in Scheme IV. Scheme IV, step k, depicts a Claisen condensation of two appropriately substituted carbonyl esters, where X for both compounds of formula (2) and formula (14) is a suitable leaving group as previously described, preferably a C1-C6 alkoxy group. The Claisen condensation is well known and appreciated in the art (March, J., *Advanced Organic Chemistry*, copyright 1985, John Wiley and Sons, Inc., pp 437-439). The products of formula (15) can be isolated and purified by techniques described above.

In Scheme IV, step d, conditions can be applied to a compound of formula (I 5) with the appropriate compound of formula (6), to give a compound of formula (16). Typically, the reaction is carried out in a suitable solvent such as ethanol, N-methylpyrrolidin-2-one, or preferably pyridine. The reaction is carried out at temperatures of about 60° C. to ambient for 4-24 hours. The products can be isolated and purified by techniques described above.

Step a, as described above, depicts the cyclization of a compound of formula (16) to give an optionally substituted compound of formula (17). Typically, the appropriate compound of formula (16) is reacted with a suitable base, preferably cesium carbonate, in a suitable solvent, preferably N,N-dimethylformamide, at temperatures of about 0 to 100° C. Optionally, a hydrolysis of the carboxyl ester of formula (117) can be performed. The products can be isolated and purified by techniques described above.

Step l depicts the transformation of a carboxylic acid, formula (17), to a halide of formula (118). This transformation is well known and appreciated in the art (Larock, R. C., *Comprehensive Organic Transformations*, 2$^{nd}$ Ed., copyright 1999, John Wiley & Sons, pp 741-742).

Step m depicts the transformation of a heteroaryl halide, formula (118), to a heteroaryl boronic acid or ester formula (19). This transformation is well known and appreciated in the art (Li, Wenjie; Nelson, Dorian P. et al, *J. Org. Chem*, 2002, 5394-5397).

SCHEME V

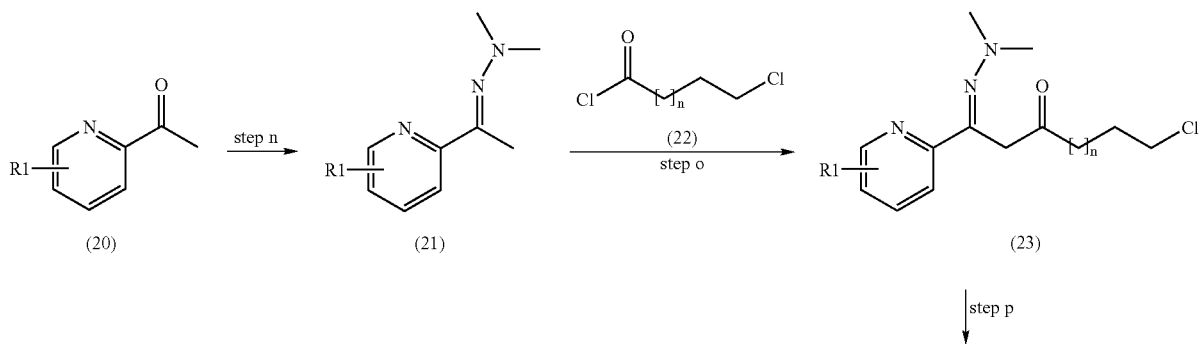

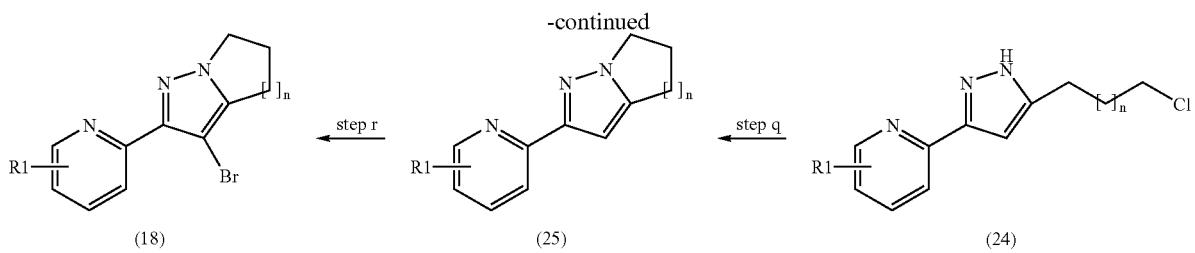

(18)     (25)     (24)

Scheme V depicts an alternative approach to the synthesis of the compound of formula (18). One skilled in the art would appreciate the conversion of various acetylpyridines of formula (20) to hydrazones of formula (21) through step n. This conversion is known in the art (Org. Synth. 1988, VI, pg. 12, J. Org. Chem. 1997, 62, 287-291). Scheme V, step o depicts the acylation of a hydrazone compound of formula (21) with a compound of formula (22) to give the product of formula (23). Typically the compound of formula (21) is contacted with a suitable base, such as potassium bis(trimethylsilyl)amide, lithium bis(trimethylsilyl)amide, sodium bis(trimethylsilyl)amide, sodium hydride, lithium hydride, potassium hydride, sodium alkoxides (sodium methoxide, or sodium ethoxide) or potassium alkoxides (potassium methoxide, or potassium ethoxide), or preferably lithium diisopropylamine. Generally, the reaction is carried out in suitable solvents, such as tetrahydrofuran, toluene, or a combination of such, at temperatures of about −78° C. to ambient temperature. The product, formula (23), can be isolated and purified by techniques well known in the art, such as precipitation, filtration, extraction, evaporation, trituration, chromatography, and recrystallization, or can be carried forward in scheme (IV) without purification. Scheme (IV), step p, depicts the conversion of a β-ketohydrazone of formula (23) to a substituted pyrazole of formula (24). Typically, a compound of formula (23) is treated with a source of hydrazine such as hydrazine, hydrazine monohydrate, hydrazine hydrate, or preferably hydrazine hydrochloride in an appropriate solvent such as tetrahydrofuran, ethanol, methanol, water, or preferably a combination of these at temperatures of about ambient temperature to reflux. The product, formula (24), can be isolated and purified by techniques well known in the art, such as precipitation, filtration, extraction, evaporation, trituration, chromatography, and recrystallization. Step q depicts the cyclization of a haloalkylpyrazole compound of formula (24) to a 5,6-dihydro-4H-pyrrolo[1,2-b]pyrazole of formula (25). Typically, the appropriate compound of formula (24) is reacted with a suitable base, preferably sodium hydride, in a suitable solvent, preferably N,N-dimethylformamide, at temperatures of about 0 to 100° C. The products of formula (25) can be isolated by methods described above. Step r depicts the halogenation of a compound of formula (25) to give a compound of formula (18). Typically the appropriate compound of formula (25) is contacted with a halogenating agent such as N-chlorosuccinamide, N-iodosuccinamide, chlorine, bromine, iodine, or preferably N-bromosuccinamide in an appropriate solvent such as dichoromethane, chloroform, benzene, or preferably N,N-dimethylformamide at temperatures of about 0 to 50° C.

SCHEME VI

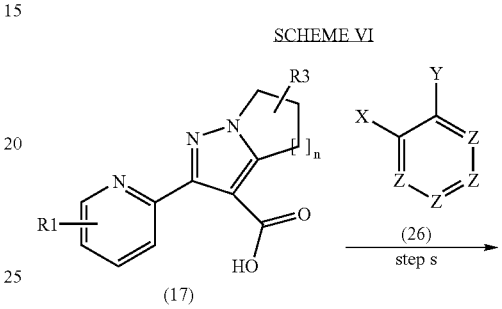

(17)

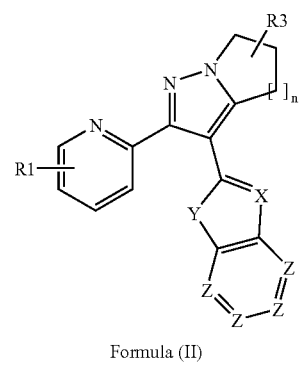

Formula (II)

Scheme VI, step s depicts the addition and cyclization of a compound of formula (26) to a compound of formula (17) to give additional compounds of the invention (Formula I). The R group(s) can be any group(s), previously defined as $R_1$, $R_2$, or $R_3$ of Formula II and the X, Y, and Z of formula (26) can be nitrogen, nitrogen or oxygen, and carbon or oxygen respectively. Typically, a compound capable of producing the acid halide of a compound of formula (17) such as phosphorous pentachloride, phosphorous oxybromide, or preferably phosphorous oxychloride is added to a mixture of a compound of formula (17) and a compound of formula (26). The reaction is heated at temperatures from 30 to about 120° C. for 1 to 18 hours. The products of Formula II can be purified by methods described above.

SCHEME VII

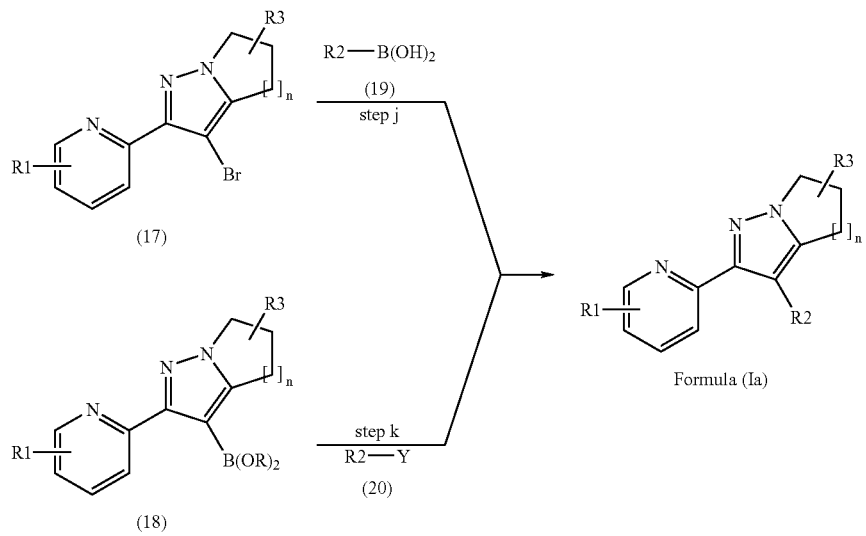

Scheme VII, step j, depicts the palladium-catalyzed coupling of a compound of formula (17) with a compound of formula (19) to give a compound of the invention (Formula Ia). Typically, the halide of formula (17) is used as a leaving group in combination with a compound of formula (19) in the presence of a suitable catalyst, preferably tetrakis(triphenylphosphine)palladium(0), and a suitable base, such as potassium carbonate, to further give compounds of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.* 1981, 513-518). The compounds of formula (19) are commercially available or can be produced by methods known in the art (Li, Wenjie; Nelson, Dorian P. et al, *J. Org. Chem.* 2002, 5394-5397). In the same way, a compound of formula (18) can be used in combination with a compound of formula (20), where Y can be an appropriate leaving group such as a halide, in the presence of a suitable palladium catalyst, preferably tetrakis(triphenylphosphine)palladium (0), and a suitable base, such as potassium carbonate, to further give compounds of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.* 1981, 513-518).

The skilled artisan will also appreciate that not all of the substituents in the compounds of Formula (Ia) will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The skilled artisan will appreciate that the compounds of Formula (Ia) may be formed into acid addition salts using pharmaceutically acceptable acids. The formation of acid-addition salts is well known and appreciated in the art.

The following preparations and examples further illustrate the preparation of compounds of the present invention and should not be interpreted in any way as to limit the scope. Those skilled in the art will recognize that various modifications may be made while not departing from the spirit and scope of the invention. All publications mentioned in the specification are indicative of the level of those skilled in the art to which this invention pertains.

Preparation 1

Preparation of 3-Bromo-2-(6-methyl-pyridin-2-yl)-5,6-dihydro-4H-pyrrolo [1,2-b]pyrazole

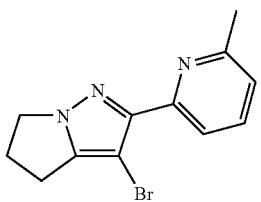

A. Preparation of 3-(6-Methyl-pyridin-2-yl)-3-oxo-propionic Acid Ethyl Ester

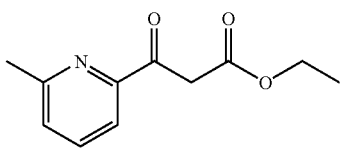

Stir a mixture of sodium ethoxide (90 g, 1.32 mol, 2 eq), toluene (0.5 L, 5 vol), and ethyl acetate (0.2 L, 1.98 mol, 3 eq) in a 2 L flask equipped with reflux condenser, mechanical stirrer, and nitrogen inlet. After 1 h, add 6-methyl-pyridine-2-carboxylic acid methyl ester (Cheung, Y, *Tetrahedron Lett.* 1979, 40, 3809-10; 100 g, 0.66 mol). Heat the mixture at reflux (92° C.) for 20 h. Cool the mixture to room temperature and acidify with glacial acetic acid to pH 6. Wash the resulting gel with water (0.5 L). Separate the layers and extract the aqueous layer with toluene (1×0.5 L) Dry the combined organic layers (sodium sulfate), filter, and concentrate in vacuo to yield the subtitled product (154 g) as a dark oil in 86% purity by HPLC analysis. MS ES+ m/e 208 (M+1).

B. Preparation of 3-(6-Methyl-pyridin-2-yl)-3-(2-oxo-pyrrolidin-1-ylimino)-propionic Acid Ethyl Ester

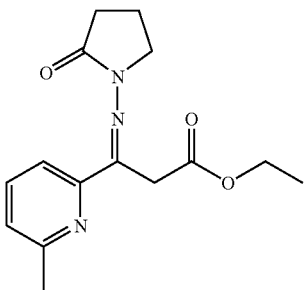

Add 1-aminopyrrolidin-2-one hydrochloride (Zubek, A. Z. Chem. 1969, 9(2), 58; 99.4 g, 0.73 mol) to a 3 L flask equipped with mechanical stirrer and nitrogen inlet. Add 3-(6-methyl-pyridin-2-yl)-3-oxo-propionic acid ethyl ester (Preparation 1, Part A; 154 g, 0.66 mol), then pyridine (280 mL). Stir the reaction mixture at room temperature for 20 h. Dilute the mixture with water (200 mL) and extract with toluene (2×250 mL). Combine the organic layers, filter, and concentrate in vacuo to yield the subtitled product (201 g) as a dark oil. MS ES+ m/e 290 (M+1).

C. Preparation of 2-(6-Methyl-pyridin-2-yl)-5,6-dihydro-4H-pyrrolo[1,2-b]pyrazole-3-carboxylic acid

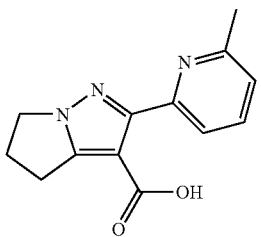

Add sodium ethoxide (90 g, 1.32 mol), toluene (5 L) and 3-(6-methyl-pyridin-2-yl)-3-(2-oxo-pyrrolidin-1-ylimino)-propionic acid ethyl ester (Preparation 1, Part B; 201 g, 0.661 mol) to a 22 L flask equipped with a mechanical stirrer, nitrogen inlet and a reflux condenser. Heat the mixture at 100° C. for 24 h then cool to room temperature. Add water (4 L) and adjust the pH to 4 with concentrated hydrochloric acid. Separate the organic layer and extract the aqueous portion with 10% isopropyl alcohol in chloroform is (3×4.5 L). Combine the organic layers, dry (sodium sulfate), filter, and concentrate in vacuo to yield the subtitled product (138 g, 86% yield) as a yellow solid in 78% purity by HPLC analysis. MS ES+ m/e 244 (M+1).

D. Preparation of 3-Bromo-2-(6-methyl-pyridin-2-yl)-5,6-dihydro-4H-pyrrolo[1,2b]pyrazole Treat a solution of 2-(6-methyl-pyridin-2-yl)-5,6-dihydro-4H-pyrrolo[1,2-b]pyrazole-3-carboxylic acid (1.4 g, 5.8 mmol) in N,N-dimethylformamide (20 mL) with N-bromo-succinamide (1 g, 5.6 mmol) and stir at room temperature for 16 h. Dilute the mixture with ethyl acetate and wash three times with water, once with brine, dry (sodium sulfate), filter, and concentrate in vacuo to yield the title compound (1.5 g, 94%) as light yellow solid. MS ES+ m/e 278 (M+1).

Preparation 2

Preparation of 2-(6-Methyl-pyridin-2-yl)-5,6-dihydro-4H-pyrrolo[1,2-b]pyrazole-3-boronic acid

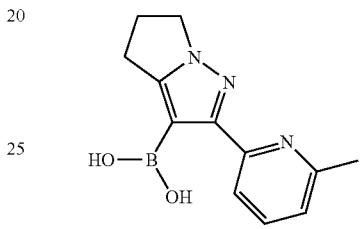

Place tetrahydrofuran (28.0 mL) in a 100 mL round-bottom flask equipped with a temperature probe, a magnetic stirrer, and a septum and put under a nitrogen atmosphere. Add 3-bromo-2-(6-methyl-pyridin-2-yl)-5,6-dihydro-4H-pyrrolo[1,2-b]pyrazole (Preparation 1, 1.44 g, 5.18 mmol) and tri-isopropyl borate (3.10 mL, 13.5 mmol). Cool the mixture to −78° C. using a dry ice/acetone bath. Add 1.4M n-butyl-lithium in hexanes (8.80 mL, 12.4 mmol) dropwise via a syringe pump over 10 min keeping the temperature below −40° C. Remove the dry ice/acetone bath and allow the reaction mixture to warm to room temperature. Add saturated aqueous ammonium chloride (10 mL) and extract with chloroform (2×1 00 mL). Combine the organic layers, dry over solid sodium chloride, and remove the solvent under reduced pressure to afford an oil. Purify the oil by normal phase flash chromatography (120 g Biotage KP-Sil 40 L: 100% ethyl acetate in hexanes for 25 min, 0-10% methanol in ethyl acetate in ramp over 15 min, then 10% methanol in ethyl acetate) to yield the title compound (910 mg, 73%). MS ES+ m/e 244 (M+1).

Preparation 3

Preparation of 2-(Pyridin-2-yl)-5,6-dihydro-4H-pyrrolo[1,2-b]pyrazole-3-carboxylic acid

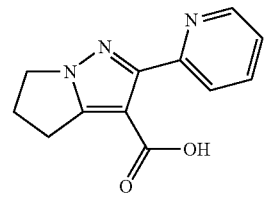

A. Preparation of 3-Oxo-3-(pyridin-2-yl)-propionic Acid Ethyl Ester

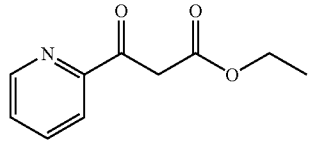

Stir a mixture of sodium ethoxide (360 g, 5.29 mol, 2 eq), toluene (4 L), ethanol (18 mL, 0.265 mol, 0.1 eq) and ethyl acetate (1.04 L, 10.58 mol, 4 eq) in a 22 L flask equipped with a reflux condenser, nitrogen inlet and mechanical stirrer. Stir for 1 h as the mixture warms to 26° C. Add pyridine-2-carboxylic acid ethyl ester (Fluka; 400 g, 2.65 mol, 1 eq) and heat the mixture to reflux (90° C.) for 18 h. Cool the mixture to room temperature. Dilute with toluene (8 L), wash with water (6 L), and separate the layers. Acidify the aqueous layer to pH 5 with glacial acetic acid. Extract with ethyl acetate (2×4 L), dry the combined organic layers (sodium sulfate), filter and concentrate in vacuo to yield the subtitled compound (466 g, 91% yield) as a dark oil in 93% purity by HPLC analysis. MS ES$^+$ m/e 194 (M+1).

B. Preparation of 3-(2-Oxo-pyrrolidin-1-ylimino)-3-(pyridin-2-yl)-propionic acid ethyl ester

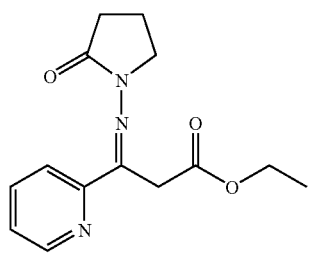

Place 1-aminopyrrolidin-2-one hydrochloride (Zubek, A. Z. *Chem.*, 1969, 9(2), 58; 155.6 g, 1.14 mol) in a 3 L flask equipped with mechanical stirrer and nitrogen inlet. Add 3-oxo-3-pyridin-2-yl-propionic acid ethyl ester (200 g, 1.04 mol) then pyridine (400 mL). Stir the reaction mixture at room temperature for 20 h. Dilute the mixture with water (500 mL), and extract with toluene (2×500 mL). Combine the organic layers, dry (sodium sulfate), filter and concentrate in vacuo to yield the subtitled compound as a dark oil (280 g, 98%). MS ES$^+$ m/e 276 (M+1).

A. Preparation of 2-(Pyridin-2-yl)-5,6-dihydro-4H-pyrrolo[1,2-b]pyrazole-3-carboxylic Acid Add sodium ethoxide (145 g, 2.03 mol), followed by toluene (7 L) and 3-(2-oxo-pyrrolidin-1-ylimino)-3-pyridin-2-yl-propionic acid (280 g, 1.02 mol) to a 22 L flask equipped with mechanical stirrer, nitrogen inlet and a reflux condenser. Heat the mixture to 100° C. for 21 h. Cool to room temperature. Add water (6 L) and adjust to pH 5 with concentrated hydrochloric acid. Separate the organic layer and extract the aqueous layer with 10% isopropyl alcohol in chloroform (2×9 L). Combine the organic layers, dry (sodium sulfate), filter and concentrate in vacuo to yield the title compound as a yellow solid (218 g, 93%). MS ES$^+$ m/e 230 (M+1).

Preparation 4

Preparation of 3-Bromo-2-(pyridin-2-yl)-5,6-dihydro-4H-pyrrolo[1,2-b]pyrazole

Stir a mixture of 2-(pyridin-2-yl)-5,6-dihydro-4H-pyrrolo[1,2-b]pyrazole-3-carboxylic acid (Preparation 3; 2 g, 8.7 mmol), sodium bicarbonate (3.3 g, 38.4 mmol) and N-bromosuccinamide (1.7 g, 9.6 mmol) in DMF (50 mL) at room temperature for 2 h. Dilute the crude mixture with 50 mL of water and 100 mL of ethyl acetate. Separate the ethyl acetate layer, extract with saturated brine, dry over anhydrous sodium sulfate, filter, and evaporate to a solid mass. Purify by MPLC (SiO$_2$, 50% ethyl acetate-hexane) to obtain the title compound (1.62 g, 70%) as a cream solid. MS ES$^+$ m/e 264 (M+1), MS ES$^+$ m/e 266 (M+2).

Preparation 4a

General Procedure for Preparation of 2-[5-(alkylchloro)-1H-pyrazol-3-yl]-pyridines Combine in a flask THF and diisopropylamine (1.3 eq) and cool to −78° C. and add 1.6M n-butyllithium in hexane (1.3 eq). Cool the solution of LDA to −78° C. and add the appropriate N,N-dimethylhydrazone (1 eq) drop-wise as a solution in THF via addition funnel over ~30 min. Stir the resulting maroon colored anion for ~30 min at −78° C. and canulate into flask containing THF and the appropriate acid chloride (2.5 eq) at −78° C. Remove the cold bath upon completion of addition and allow the reaction to warm to 0-5° C. Add hydrazine mono-hydrochloride (1.9 eq), 4:1 ethanol/water and heat at reflux for 2 h. Cool the reaction and concentrate. Dilute with methylene chloride and water and transfer to a separatory funnel. Add saturated sodium bicarbonate, shake and separate layers. Extract the aqueous layer with methylene chloride, wash the combined organic layer with 1:1 saturated bicarbonate/brine and dry over sodium sulfate. Purify using a silica gel plug in a scintered glass funnel using silica gel and topped with sand and piece of filter paper. Pre-wet the column with methylene chloride and pour the crude organic solution containing drying agent on top of the column. Elute with 75% hexane/25% EtOAc, 50% hexane/50% EtOAc, 25% hexane/75% EtOAc and concentrate to obtain the desired product in sufficient purity for use in the next step.

Preparation 4b

General Procedure for Prepartion of 3-Bromo-2-aryl-5,6-dihydro-4H-pyrrolo[1,2-b]pyrazoles and 3-Bromo-2-aryl-4,5,6,7-tetrahydro-pyrazolo[1,5-a]pyridines

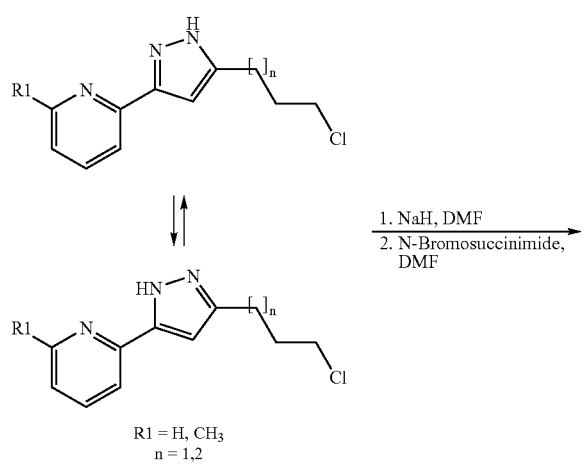

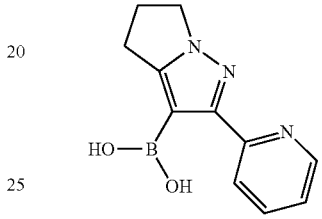

To a 2 L flask add NaH (60% oil dispersion, 1.2 eq). Wash the NaH with hexane three times and add DMF. Cool the mixture to 0° C. in an ice bath and introduce appropriate 2-[5-(alkylchloro)-1H-pyrazol-3-yl]-pyridine (1 eq) as a solution in DMF over 30 min. Remove the ice bath and stir for approximately 1 h or until cyclization is complete. Introduce sodium bicarbonate (1.2 eq) and cool to 0° C. Add N-bromosuccinimide (1.1 eq) slowly and stir for ~15 min. Remove the cold bath, pour into water, extract into methylene chloride, wash the combined organic layer with water and brine, dry over sodium sulfate, filter, and concentrate. Purify using silica gel plug in a scintered glass funnel using silica gel topped with sand and a piece filter paper. Pre-wet the column with 75% hexane/EtOAc and pour the crude organic on top of the column using methylene chloride for the transfer. Elute with 75% hexane/25% EtOAc, 50% hexane/50% EtOAc, 25% hexane/75% EtOAc, and EtOAc step gradients to obtain the corresponding product.

Preparation 5

Preparation of 2-(Pyridin-2-yl)-5,6-dihydro-4H-pyrrolo[1,2-b]pyrazole-3-boronic acid

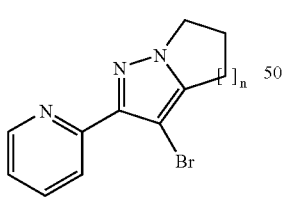

Place tetrahydrofuran (60.0 mL) in a 100 mL round-bottom flask equipped with a temperature probe, a magnetic stirrer, and a septum and put under a nitrogen atmosphere. Add 3-bromo-2-pyridin-2-yl-5,6-dihydro-4H-pyrrolo[1,2-b]pyrazole (Preparation 4, 3.00 g, 11.4 mmol) and triisopropyl borate (6.80 mL, 29.5 mmol). Cool the mixture to −78° C. using a dry ice/acetone bath. Add 1.41M n-butyllithium in hexanes (19.3 mL, 27.3 mmol) dropwise via a syringe pump over 10 min keeping the temperature below −40° C. Remove the dry ice/acetone bath and allow the reaction mixture to warm to room temperature. Add saturated aqueous ammonium chloride (20 mL) and extract with chloroform (2×150 mL). Combine the organic layers, dry over solid sodium chloride, and remove the solvent under reduced pressure to afford an oil. Purify by normal phase flash chromatography (120 g Biotage KP-Sil 40 L: ethyl acetate for 25 min, 0-10% methanol in ethyl acetate in ramp over 15 min, then 10% methanol in ethyl acetate) to obtain the title product (1.43 g, 55%). MS ES+ m/e 230 (M+1).

Preparation 5a

General Procedure for Preparation of 3-Boronic acid-2-aryl-5,6-dihydro-4H-pyrrolo[1,2-b]pyrazoles and 3-Boronic acid-2-aryl-4,5,6,7-tetrahydro-pyrazolo[1,5-a]pyridines

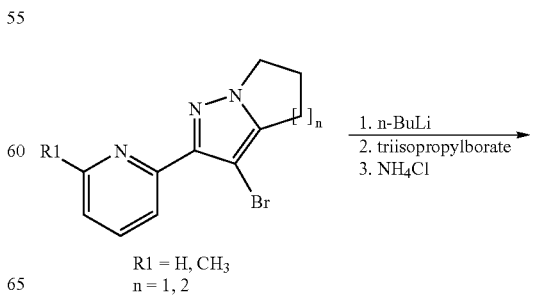

-continued

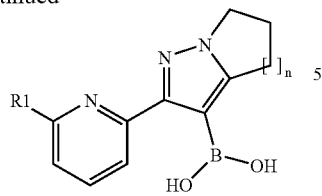

Cool a solution of the appropriate (1 eq) in THF using a dry ice/diethyl ether bath. (−74 C.°). Introduce 2.5 M n-butyllithium in hexanes (2 eq) at a rate such that the temperature does not exceed −60° C. and stir for 30 min. Add triisopropyl borate (4 eq) slowly and allow to warm to ~10° C. over 3 h. Dilute with saturated ammonium chloride and stir for 3 h to overnight. Concentrate and extract into methylene chloride. Collect white precipitate by filtration from the water layer and organic layer and rinse with water and dry. Concentrate the organic layer and triturate the residue with diethyl ether and or hexane to give the corresponding product as a white solid. Combine solids for final isolation of the title compound(s).

Preparations 6-8

General Preparation of Aryliodides

Add potassium iodide (2.0-5.0 eq) and copper(I) iodide (0.1-0.5 eq) to a solution of the arylbromide in anhydrous DMF (2.0-7.0 mL) in a 10 mL glass tube. Seal the reaction vessel with a septum and place in the microwave cavity. Use microwave irradiation of 150 W and heat to 130° C. over 30 seconds. Hold the reaction mixture at this temperature for 3-6 h. Cool the reaction vessel to room temperature before opening. Partition the reaction mixture between diethyl ether and water. Extract the water layer twice with ether then wash the combined extracts with saturated aqueous ammonium chloride, 5% aqueous lithium chloride, 5% aqueous sodium thiosulfate, water, and brine. Dry the ether layer over sodium chloride, decant, and then remove the solvent under reduced pressure using a rotary evaporator to give the title compound. Alternatively, add diethyl ether to the reaction mixture to precipitate the inorganic salts. Filter and remove the solvent under reduced pressure to give the title compound. Additional purification may be carried out by passage through silica gel or SCX resin.

The following compounds were prepared via the General Preparation of Aryliodides:

| PREPARATION | Product | Starting Material | Physical Data |
|---|---|---|---|
| 6 | 7-iodoisoquinoline | 7-bromoisoquinoline (Miller, R. B. et al, J. Org. Chem. 1980, 45, 5312-5315) | MS ES+ m/e 256 (M + 1) |
| 7 | 4-iodoisoquinoline | 4-bromoisoquinoline (Aldrich) | MS ES+ m/e 256 (M + 1) |
| 8 | 4-fluoro-7-iodo-benzofuran | 7-bromo-4-fluoro-benzofuran (PCT Int. Appl. (2000), WO 2000000196 A1) | MS ES+ m/e 263 (M + 1) |

Preparation 9

Preparation of 6-Bromo-3-(morpholin-4-yl)methyl-imidazo[1,2-a]pyridine

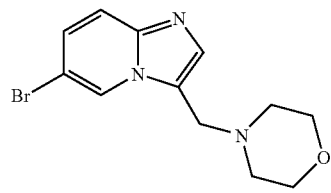

Reflux a solution of 6-bromo-imidazo[1,2-a]pyridine-3-carbaldehyde (J. Med. Chem. 1970, 13(6), 1048-51; 0.45 g, 1.99 mmol), morpholine (1.7 g, 19.9 mmol), and acetic acid (0.12 mL, 1.99 mmol) in toluene (200 mL) for 3 h. Concentrate to dryness and re-dissolve in methanol (100 mL). Add sodium borohydride (0.226 g, 5.99 mmol) in portions and stir for 30 min. Concentrate to ~25 mL, dilute with saturated aqueous sodium bicarbonate, extract into ethyl acetate, combine and concentrate. Flash chromatography gives the titled compound (0.25 g, 42%). MS ES+ m/e 295.8, 297.8 (M+1). $^1$H NMR (400 MHz, DMSO-$d_6$) δ 8.69 (s, 1H), 7.54 (d, J=10 Hz, 1H), 7.51 (s, 1H), 7.35 (d, J=10 Hz, 1H), 3.81 (s, 2H), 3.52 (t, J=4 Hz, 1H), 2.35 (t, J=4 Hz, 4H).

Preparation 10

Preparation of 2-(6-Bromo-imidazo[1,2-a]pyridin-3-yl)-1-morpholin-4-yl-ethanone

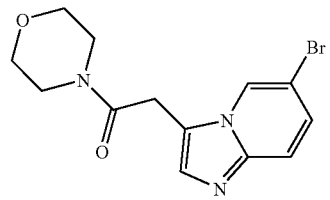

A. Preparation of (6-Bromo-imidazo[1,2-a]pyridin-3-yl)-acetic acid ethyl ester

Reflux a solution of 4,4-dimethoxy-but-2-enoic acid ethyl ester (3.3 g, 19.12 mmol) and toluene-4-sulfonic acid (0.02 g, 0.12 mmol) in a solution of 2:1 acetonitrile:water (90 mL) for 30 min. Add 2-amino-5-bromo-pyridine (1.65 g, 9.56 mmol) and reflux for 15 h. Cool and concentrate to ~20 mL. Dilute the reaction with saturated aqueous sodium bicarbonate and extract into ethyl acetate. Combine and concentrate organic extracts. Flash chromatography using ethyl acetate/dichloromethane/methanol mixtures gives the subtitled compound as a brown oil (2.9 g). TOF MS ES+ exact mass calculated for $C_{11}H_{11}BrN_2O_2$ (p+1): m/z=283.0075 Found: 283.0082. $^1$H NMR (400 MHz, DMSO-$d_6$) δ 8.68 (s, 1H), 7.55 (d, J=10 Hz, 1H), 7.49 (s, 1H), 7.34 (d, J=10 Hz, 1H), 4.15 (s, 2H), 4.09 (q, J=4 Hz, 2H), 1.18 (t, J=4 Hz, 3H). EA Calcd. For $C_{11}H_{11}BrN_2O_2$: C, 46.66; H, 3.92; N, 9.89; Found C, 46.56; H, 4.02; N, 9.60.

B. Preparation of 2-(6-Bromo-imidazo[1,2-a]pyridin-3-yl)-1-morpholin-4-yl-ethanone Add 0.5M diisobutylaluminum hydride in toluene (4.6 mL, 2.29 mmol) to a solution of (6-bromo-imidazo[1,2-a]pyridin-3-yl)-acetic acid ethyl ester (0.65 g, 2.29 mmol) and morpholine (5 mL) in THF (40 mL) at −78° C. Gently warm the reaction to room temperature and dilute carefully with methanol. Filter and concentrate the filtrate. Flash chromatography gives the subtitled compound (0.24 g, 32%) as a white solid. MS ES+ m/e 324.0, 326.0 (M+1).

Preparation 11

Preparation of 2-(6-Bromo-imidazo[1,2-a]pyridin-2-yl)-1-morpholin-4-yl-ethanone

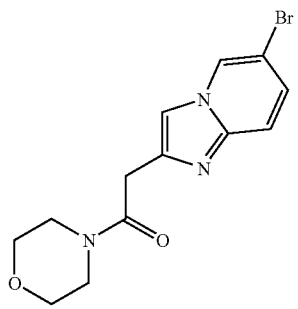

A. Preparation of (6-Bromo-imidazo[1,2-a]pyridin-2-yl)-acetic Acid Ethyl Ester Add 4-bromo-3-oxo-butyric acid ethyl ester (12.08 g, 57.8 mmol) to a solution of 2-amino-5-bromo pyridine (5.0 g, 28.9 mmol) in acetonitrile (80 mL). Reflux for 4 days and concentrate to dryness. Purify by flash chromatography using appropriate ethyl acetate/methanol mixtures to give the subtitled compound (5.75 g, 70%) as a brown oil. TOF MS ES+ exact mass calculated for C, HI BrN$_2$O$_2$ (p+1): m/z=283.0082 Found: 283.0084. $^1$H NMR (400 MHz, DMSO-d$_6$) δ 8.68 (m, 1H), 7.82 (s, 1H), 7.45 (d, J=10 Hz, 1H), 7.30 (dd, J=10, 2.0 Hz, 1H), 4.08 (q, J=7.0 Hz, 2H), 3.77 (s, 2H), 1.18 (t, J=7.0 Hz, 3H).

B. Preparation of 2-(6-Bromo-imidazo[1,2-a]pyridin-2-yl)-1-morpholin-4-yl-ethanone Add 2M trimethylaluminum in toluene (1.94 mL, 3.88 mmol) to a solution of morpholine (0.34 g, 3.88 mmol) in dichloromethane (10 mL). Stir for 10 min and add a solution of (6-bromo-imidazo[1,2-a]pyridin-2-yl)-acetic acid ethyl ester (1.1 g, 3.88 mmol) in dichloromethane (12 mL). Heat at 40° C. for 1 h, carefully dilute with saturated aqueous ammonium chloride and extract into dichloromethane. Concentration followed by filtration gives the titled compound (0.55 g, 43%) as a white solid. TOF MS ES+ exact mass calculated for C$_{13}$H$_{14}$BrN$_3$O$_2$ (p+1): m/z=324.0348; Found: 324.0330. $^1$H NMR (400 MHz, DMSO-d$_6$) δ 8.84 (m, 1H), 7.77 (s, 1H), 7.45 (d, J=10 Hz, 1H), 7.29 (dd, J=10, 2.0 Hz, 1H), 3.81 (s, 2H), 3.55-3.4 (m, 8H).

Preparation 12

Preparation of 6-Bromo-imidazo[1,2-a]pyridine-3-carboxylic acid (2-dimethylamino-ethyl)-amide

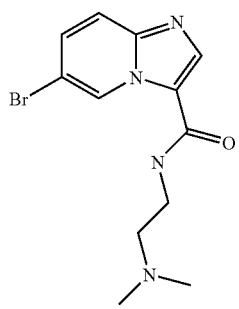

A. Preparation of 6-Bromo-imidazo[1,2-a]pyridine-3-carboxylic acid ethyl ester Add concentrated sulfuric acid (0.56 g, 5.78 mmol) to a suspension of 2-chloro-3-oxo-propionic acid ethyl ester potassium salt (*Tetrahedron* 2000, 58(40), 7915-7921; 3.27 g, 17.3 mmol) and 2-amino-5-bromopyridine (1.0 g, 5.78 mmol) in ethanol (100 mL). Reflux for 2 h, cool, and carefully dilute with saturated aqueous sodium bicarbonate. Extract in ethyl acetate, combine organic extracts, and concentrate. Flash chromatography using appropriate ethyl acetate/methanol mixtures gives 0.85 g (55%) of the subtitled compound as a white solid. MS ES+m/e 269.0, 271.0 (M+1) bromine isotope. $^1$H NMR (400 MHz, DMSO-d$_6$) δ 9.32 (m, 1H), 8.28 (s, 1H), 7.79 (d, J=10 Hz, 1H), 7.70 (dd, J=10, 2 Hz, 1H), 4.36 (q, J=7.0 Hz, 2H), 1.33 (t, J=7.0 Hz, 3H).

B. Preparation of 6-Bromo-imidazo[1,2-a]pyridine-3-carboxylic acid (2-dimethylamino-ethyl)-amide Add 6-bromo-imidazo[1,2-a]pyridine-3-carboxylic acid ethyl ester (0.11 g, 0.41 mmol) to a sealed tube containing N,N-dimethyl-ethane-1,2-diamine (5 mL). Heat the reaction at 150° C. for 24 h. Flash chromatography using appropriate mixtures of dichloromethane/2M ammonia in methanol gives 0.14 g of the product as a yellow oil. This material is progressed further without characterization. MS ES− m/e 269.0, 311.0 (M−1).

Preparation 13

Preparation of 6-Iodo-imidazo[1,2-a]pyridine-2-carboxylic acid ethyl ester

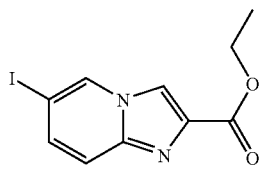

Add 3-bromo-2-oxo-propionic acid ethyl ester (1.75 g, 9.09 mmol) to a solution of 2-amino-5-iodo pyridine (*Tetrahedron* 2002, 58, 2885-2890; 1.0 g, 4.54 mmol) in acetonitrile (100 ml). Reflux for 12 h, concentrate to ~30 ml, and dilute with saturated aqueous sodium bicarbonate. Extract into dichloromethane, combine organic extracts, dry over anhydrous magnesium sulfate, and concentrate. Titurate the residue in diethyl ether and filter to give 0.8 g (56%) of the subtitled compound as an off-white solid. TOF MS ES+ exact mass calculated for $C_{10}H_{9}IN_2O_2$ (p+1): m/z=316.9787; Found: 316.9784. $^1$H NMR (400 MHz, DMSO-$d_6$) δ 8.97 (m, 1H), 8.46 (s, 1H), 7.57-7.49 (m, 2H), 4.32 (q, T 7.0 Hz, 2 Hz), 1.33 (t, J=7.0 Hz, 3H).

Preparation 14

Preparation of 6-Iodo-imidazo[1,2-a]pyridine-3-carboxylic acid ethyl ester

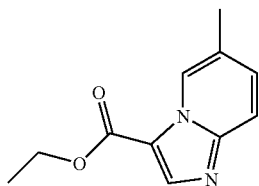

Reflux a solution of 3-oxo-propionic acid ethyl ester (*J. Med. Chem.* 2001, 44(12), 1193-2003; 3.4 g, 23.7 mmol) and 2-amino-5-iodopyridine in 1:1 acetonitrile/ethanol (100 mL) overnight. Dilute with saturated aqueous sodium bicarbonate, extract into dichloromethane (4×100 mL), combine organics, and concentrate. Flash chromatography using appropriate ethyl acetate/hexane mixtures gives 3.7 g (78%) of the subtitled compound as an off-white solid. ES+ m/e 316.7 (M+1).

Preparation 15

Preparation of 6-Bromo-8-fluoro-imidazo[1,2-a]pyridine

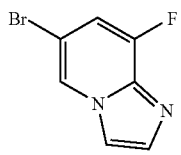

Prepared in a manner similar to Example 14, Part A. $^1$H NMR (400 MHz, DMSO-$d_6$) δ 8.8 (d, J=1, 1H), 8.03 (dd, J=3,1, 1H), 7.63 (d, J=1 Hz, 1H), 7.4 (dd, J=11, 1 Hz, 1H.

Preparation 15a

Preparation of (5-Iodopyridin-2-yl)-methylene-amine

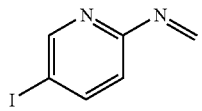

Add trifluoroacetic acid (3 drops) to a suspension of 2-amino-5-iodopyridine (1.0 g, 4.5 mmol) and paraformaldehyde (1.0 g). Heat the mixture at reflux for 15 h and concentrate. Purification by flash chromatography eluting with ethyl acetate gives 0.8 g (75%) of the title compound as a white solid. ES+ m/e 232.6 (M+1).

Preparation 16

Preparation of (6-Iodo-imidazo[1,2-a]pyridin-3-yl)-(1,1,3,3-tetramethyl-butyl)-amine

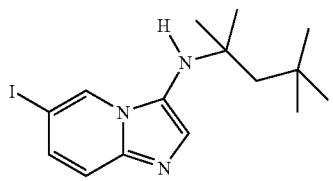

Add 1,1,3,3-tetramethylbutyl isocyanide (Aldrich; 0.57 g, 4.06 mmol) to a solution of (5-iodo-pyridin-2-yl)-methylene-amine (Preparation 15a; 0.8 g, 3.4 mmol) in methanol (20 mL). Reflux for 36 h and concentrate. Purify by flash chromatography eluting with a gradient of 100% hexanes to 50% EtOAc/50% hexanes (45 mL/min, 44 min) giving 0.5 g (40%) of the title compound as a dark brown semi-solid. ES+ m/e 371.8 (M+1).

Preparation 17

Preparation of N-Acetyl-N-(6-bromo-imidazo[1,2-a]pyridin-3-yl)-acetamide

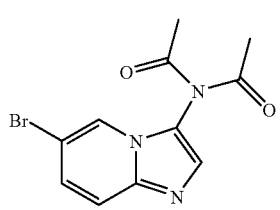

Add trifluoroacetic acid (10 ml) to a solution of (6-bromo-imidazo[1,2-a]pyridin-3-yl)-(1,1,3,3-tetramethyl-butyl)-amine (prepared in a manner similar to Preparation 12; 0.5 g, 1.54 mmol). Reflux for 1 h and concentrate to dryness. Flash chromatography using ethyl acetate/methanol mixtures gives the off-white solid intermediate 6-bromo-imidazo[1,2-a]pyridin-3-ylamine ES+ m/e 213.6 (bromine isotopes) (M+1). Immediately dissolve intermediate in dichloromethane and add pyridine (1 g, 12.64 mmol) followed by acetic anyhydride (1.5 g, 14.69 mmol) and reflux for 14 h. Concentration followed by purification by flash chromatography gives 0.38 g (83%) of the title compound. ES+ m/e 297.7 (bromine isotopes) (M+1).

Preparation 18

Alternate Preparation of 3-Boronic acid-2-(6-methyl-pyridin-2-yl)-5,6-dihydro-4H-pyrrolo[1,2-b]pyrazole

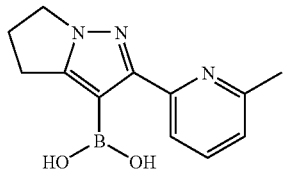

Dissolve 3-bromo-2-(6-methyl-pyridin-2-yl)-5,6-dihydro-4H-pyrrolo[1,2-b]pyrazole (20 g, 72 mmol) in dry THF (700 mL). Cool the solution to −75° C. under nitrogen. Add 2.5M n-butyllithium in hexanes (70 ml, 150 mmol) to the solution over 30 min. maintaining the temperature under −65° C. Stir the solution for 30 min. and add triisopropyl borate (Aldrich; 80 mL, 350 mmol) to the mixture over 20 min. Stir for 30 min., then allow the mixture to warm to room temperature over 3 h. Dilute the reaction with 300 mL of staturated ammonium chloride and stir for 2 h. Evaporate some of the solvent and dilute the crude product with 3:1 Chroloform/isopropyl alcohol (2 L). Wash organic layer with brine (500 mL×3), over sodium sulfate, and evaporate the solvent to give the titled compound (15.5 g, 87%) as a pale yellow solid. MS (electrospray, m/z) 244 (M+1).

Preparation 19

Preparation of 3-Boronic acid-2-(6-pentyl-pyridin-2-yl)-5,6-dihydro-4H-pyrrolo[1,2-b]pyrazole

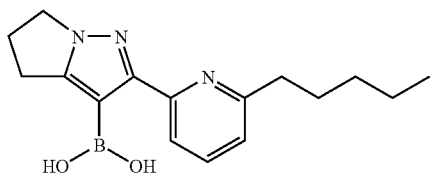

The title compound was obtained as a by-product from preparation 18.

Preparation 20

Alternate Preparation of 3-Boronic acid-2-(pyridin-2-yl)-5,6-dihydro-4H-pyrrolo [1,2-b]pyrazole

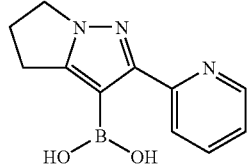

Prepare using identical procedures to that used in Preparation 18 except employing 3-bromo-2-(pyridin-2-yl)-5,6-dihydro-4H-pyrrolo[1,2-b]pyrazole.

Preparation 21a

2-Ethoxycarbonylmethoxy-5-iodo-benzoic acid methyl ester

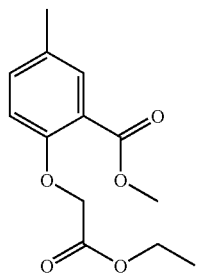

Reflux a mixture of 2-hydroxy-5-iodo-benzoic acid methyl ester (TCI; 5.5 g, 20 mmol) and ethyl bromoacetate (Aldrich; 6.7 g, 40 mmol) in acetone (60 mL) in the presence of potassium (5.5 g, 40 mmol) for 3 h. Filter out the solid and evaporate acetone to give a white residue. Dissolve the residue in ethyl acetate and wash with brine. Evaporate the solvent in vacuum to give final product as a white solid (7 g, 96%). MS (electrospray, m/z) 365 (M+1). $^1$H NMR (400 MHz, CDCl$_3$) δ 8.1 (d, J=2.0 Hz, 1H), 7.70 (dd, J=8.8, 2.8 Hz, 1H), 6.6 (d, J=8.8 Hz, 1H), 4.68 (s, 2H), 4.3 (q, J=6.8 Hz, 2H), 3.9 (s, 1H), 1.3 (t, J=6.8 Hz, 3H).

Preparation 21b

Acetic acid 5-Iodobenzofuran-3-yl ester

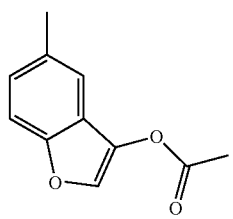

Place 2-carboxymethoxy-5-iodo-benzoic acid (Preparation 21a; 7 g, 21 mmol) acetic anhydride (35 ml), sodium acetate (4 g), and acetic acid (5 mL) into a 50 mL round bottom flask. Heat the resulting mixture at 140° C. under stirring for 5 h and cool to room temperature. Add water (12 mL) into the mixture gradually maintaining the temperature below 60° C. and continue to stir for 18 h. Dilute with water (200 mL) and collect the resulting precipitate via vacuum filtration. Wash the solid with water and dry to give the final product (6 g, 95%). MS (electrospray, m/z) 303 (M+1).

Preparation 22

Preparation of a Mixture of 6-Iodo-1-methyl-1H-benzoimidazole and 5-Iodo-1-methyl-1H-benzoimidazole

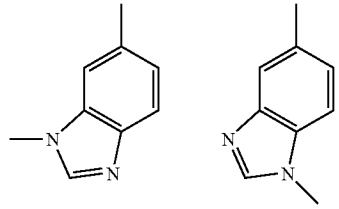

Stir 5-iodo-1H-benzoimidazole (U.S.S.R. 1616911, 30 Dec. 1990; 2.1 g, 8.6 mmol), iodomethane (1.6 mL, 25.8 mmol), and sodium hydride (0.62 g, 26.0 mmol) in DMF (20 mL) at room temperature for 2 h. Extract the product with 3:1 chloroform/isopropyl alcohol and wash the organic phase with saturated sodium chloride. Dry over sodium sulfate to give the desired product as a dark yellow solid (2.13 g, 96%). MS (electrospray, m/z) 259.0 (M+1).

Preparation 23

Preparation of a Mixture of 6-Iodo-1-[3-(tetrahydropyran-2-yloxy)-propyl]-1H-benzoimidazole and 5-Iodo-1-[3-(tetrahydro-pyran-2-yloxy)-propyl]-1H-benzoimidazole

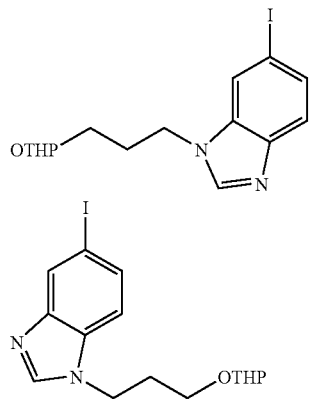

Stir 5-iodo-1H-benzoimidazole (U.S.S.R. pat. 1616911, 30 Dec. 1990; 2.0 g, 8.2 mmol), 2-(2-bromoethoxy)tetrahydro-2H-pyran (4.0 mL, 26.5 mmol), sodium hydride (0.78 g, 32.8 mmol) in DMF (20 m]L) at room temperature for 2 h.

Extract the product with 3:1 chloroform/isopropyl alcohol and wash with saturated sodium chloride. Dry the organic phase over sodium sulfate and filter to give a dark yellow oil. Purify by silica gel flash chromatography eluting with dichloromethane to 10% THF/90% dichloromethane to afford a light yellow oil as a mixture of the two titled compounds (2.59 g, 83%). MS (electrospray, m/z) 387.1 (M+1).

Preparations 24 and 25

Preparation of a Mixture of 5-Iodo-benzoimidazole-1-carboxylic acid tert-butyl ester and 6-Iodo-benzoimidazole-1-carboxylic acid tert-butyl ester

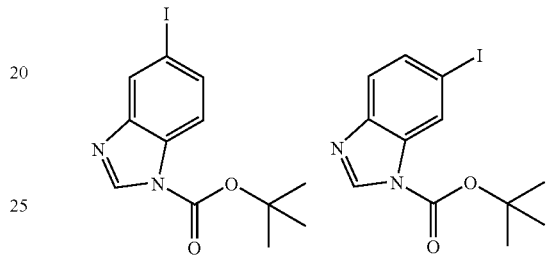

Add di-tert-butyl dicarbonate (0.37 g, 1.7 mmol) and DMAP (20 mg, 0.16 mmol) to a solution of 5- and 6-iodobenzimidazole (Rabiger, D. J.; Jouilie, M. M.; *J. Org. Chem.* 1961, 26, 1649; 0.38 g, 1.6 mmol) in dioxane (7.5 mL). Stir the reaction mixture for 17 h. Add N,N-dimethylethylenediamine (0.3 mL). Dilute the reaction mixture with ethyl acetate and wash the organic layer with 0.1N aqueous hydrochloric acid and brine. Concentrate in vacuo and purify by flash column chromatography, using an appropriate mixture of ethyl acetate/hexanes, to provide the subtitled compound as a 2:3 mixture of two regioisomers (136 mg, 25%).

Minor isomer: MS (ESI) m/e=345 (M+1). $^1$H NMR (CDCl$_3$) δ 8.36 (s, 1H), 8.13 (d, J=1 Hz, 1H), 7.76 (d, J=8 Hz, 1H), 7.67 (dd, J=8, 1 Hz, 1H), 1.70 (s, 9H). TLC (SiO$_2$): R$_f$0.7 (1:1 ethyl acetate/hexanes). Major isomer: MS (ESI) m/e=345 (M+1). $^1$H NMR (CDCl$_3$) δ 8.40 (d, J=2 Hz, 1H), 8.33 (s, 1H), 7.65 (dd, J=9, 2 Hz, 1H), 7.53 (d, J=9 Hz, 1H), 1.70 (s, 9H). TLC (SiO$_2$): R$_f$0.6 (1:1 ethyl acetate/hexanes).

Preparation 26

Preparation of 7-Bromo-2-chloro-quinoxaline

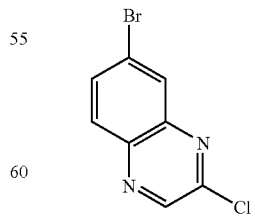

Heat benzene-1,2-diamine (7.5 g, 69 mmol) and oxo-acetic acid ethyl ester (20 mL) in ethanol (100 mL) at 120° C. for 18 h. Cool, filter the resulting precipitate, and wash with dry ether to give 1H-quinoxalin-2-one (6.7 g). Dissolve 1H-quinoxalin-2-one in acetic acid (300 mL), add bromine (5 mL), and stir the reaction mixture for 1 h. Filter the resulting crystals and wash with ether to afford 7-bromo-1H-quinoxalin-2-one (7.2 g). Reflux 7-bromo-1H-quinoxalin-2-one in POCl$_3$ (30 mL) for 18 h. Remove POCl$_3$ in vacuo, dissolve the product in 3:1 chloroform/isopropyl alcohol, and wash the organic phase with saturated sodium bicarbonate. Dry over sodium sulfate and purify by silica gel flash chromatography eluting with dichloromethane to 10% methanol/90% dichloromethane to afford the title compound as a yellow solid (4.5 g, 58%). MS (electrospray, m/z) 243.0 and 245.0 (M+1).

Preparation 27

Preparation of 2-(7-Bromo-quinoxalin-2-yloxy)-ethanol

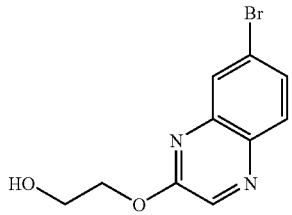

Suspend sodium hydride (310 mg, 13 mmol) in a solution of ethylene glycol (800 mg, 13 mmol) in DMF (50 mL) at 0° C. After stirring for 30 min at room temperature, 7-bromo-2-chloro-quinoxaline (Preparation 26; 610 mg, 2.5 mmol) is added. Stir for 2 h at room temperature and dilute with 3:1 chloroform/isopropyl alchol. Wash the organic phase with brine and purify by FCC to give the title compound (564 mg, 85%). MS m/e (268, M+1). $^1$H NMR (400 MHz, CDCl$_3$) δ 8.5 (s, 1H), 8.0 (d, J=2.0 Hz), 7.90 (dd, J=8.8, 2.0 Hz, 1H), 7.7 (d, J=8.8 Hz, 1H), 4.6 (t, d=4.8 Hz, 2H), 43.9 (t, J=4.8 Hz, 2H).

Preparation 28

Preparation of 6-Bromobenzothiazole

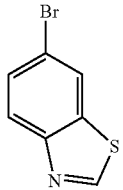

Add anhydrous copper (II) bromide (1.79 g, 7.99 mmol), tert-butyl nitrite (1.2 mL, 9.98 mmol) and anhydrous acetonitrile (20 mL) to a round bottom flask fitted with a reflux condenser and an addition funnel. Heat at 65° C. for 10 min. Add a solution of benzothiazol-6-ylamine (Lancaster; 1 g, 6.66 mmol) in acetonitrile (10 mL) over a period of 5 min via addition funnel. Stir at 65° C. for 30 min. Cool to room temperature, pour into 20% aqueous hydrochloric acid (100 mL), and extract with ether (2×100 mL). Wash the organic layer with 20% aqueous hydrochloric acid. Dry the organic phase with sodium sulfate, filter, evaporate and chromatograph (10% ethyl acetate/90% hexanes) to give the title product (0.4 g, 29%) as a pale yellow solid. MS (ESI) m/e 215 (M+1). $^1$H NMR (CDCl$_3$): δ 8.95 (s, 1H), 8.10-8.06 (m, 1H), 8.00-7.94 (m, 1H), 7.65-7.56 (m, 1H). TLC (SiO$_2$): R$_f$ 0.23 (50% ethyl acetate/50% hexanes).

Preparation 29

Preparation of 5-Iodo-pyrazolo[1,5-a]pyrimidine

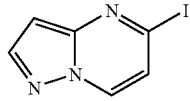

Dissolve 5-chloro-pyrazolo[1,5-a]pyrimidine (Hans Reimlinger et al., Chem. Ber. 1970, 103, 3252-3265; 1.15 g, 7.5 mmol) and sodium iodide (5.6-g, 37.4 mmol) in anhydrous acetonitrile (50 mL). Add acetyl chloride (2.7 ml, 37.9 mmol). Stir and reflux under nitrogen for 20 h. Pour the reaction mixture into a stirring mixture of 0.5M aqueous potassium carbonate (200 mL), 1.0M aqueous sodium sulfite (50 mL), and diethyl ether (350 mL). Separate the organic layer, dry over anhydrous magnesium sulfate, filter and concentrate under reduced pressure. Chromatograph the crude product on flash silica using neat dichloromethane to obtain 950 mg (51%) of the title compound as a yellow solid. TOF MS ES+ exact mass calculated for C$_6$H$_4$N$_3$$_1$$_0$): m/z=245.9528; Found: 245.9517. $^1$H NMR (400 MHz, DMSO-d$_6$) δ 8.82 (d, J=7 Hz, 1H), 8.18 (d, J=2 Hz, 1H), 7.32 (d, J=7 Hz, 1H), 6.69 (d, J=2 Hz, 1H).

Preparation 30

General Suzuki Coupling Method A

Add the heteroaryl halide (1-1.2 eq) and THF (0.2 M) to a round-bottom flask under argon. Purge the solution with argon for 10 min. Add tris(dibenzylideneacetone) dipalladium(0) (Strem; 0.1 eq) and bis[1,2-bis(diphenylphosphino)ethane]palladium(0) (Strem; 0.1 eq). Purge the reaction with argon for 2 min and stir at room temperature for 20 min. Add 2-(pyridin-2-yl)-5,6-dihydro-4H-pyrrolo[1,2-b]pyrazole-3-boronic acid or 2-(6-methyl-pyridin-2-yl)-5,6-dihydro-4H-pyrrolo[1,2-b]pyrazole-3-boronic acid (1.0 eq) in THF (0.3 M). Stir the reaction mixture for 10 min. Add 2M aqueous potassium carbonate (2.4 eq). Heat the reaction to 40° C. Add additional tris(dibenzylideneacetone) dipalladium(0) (0.1 eq) after 1.5 h and again after 3 h. Continue heating the reaction for ~15 hr. Cool the reaction mixture to room temperature and concentrate in vacuo. Purify by SCX resin, eluting with 2M ammonia in methanol, followed by flash column chromatography (silica gel, eluting with the appropriate mixture of methylene chloride/chloroform/methanol/concentrated aqueous ammonium hydroxide). Concentrate in vacuo to provide the final compound.

Preparation 31

General Suzuki Coupling Method B

Add 2-(pyridin-2-yl)-5,6-dihydro-4H-pyrrolo[1,2-b]pyrazole-3-boronic acid (1.0 eq), the hetroaryl halide (1.2 eq), cesium carbonate (2.0 eq), and THF (0.2M) to a round-bottom flask under argon. Purge the solution with argon for 10 min. Add tris(dibenzylideneacetone) dipalladium (0) (Strem; 0.1 eq.) and 1,3-bis(2,6-di-1-propylphenyl) imidazolium chloride (Strem; 0.2 eq.). Heat the reaction to 60° C. Add additional tris(dibenzylideneacetone) dipalladium (0) (0.1 eq.) and 1,3-bis(2,6-di-1-propylphenyl) imidazolium chloride (0.2 eq.) after 3 h. Stir the reaction mixture at 60° C. for ~15 h. Cool the reaction to room temperature and concentrate in vacuo. Purify by SCX resin, eluting with 2M ammonia in methanol, followed by flash column chromatography (silica gel, eluting with the appropriate mixture of methylene chloride/chloroform/methanol/concentrated aqueous ammonium hydroxide). Concentrate in vacuo to provide the final compound.

Preparation 32

General Suzuki Coupling Method C

Add 2-(pyridin-2-yl)-5,6-dihydro-4H-pyrrolo[1,2-b]pyrazole-3-boronic acid (1.0 eq), the hetroaryl halide (1.0-1.2 eq), sodium bicarbonate (2.0 eq), tetrakis(triphenylphosphine) palladium (0) (Strem; 0.02-0.05 eq), acetonitrile (0.1M), and water (0.1M) to a microwave reactor vessel. Seal the reactor vessel and irradiate with microwave radiation for 15 min at 110° C. Cool the reaction mixture to room temperature. Extract the reaction mixture with chloroform (3×25 mL), dry the combined extracts with sodium sulfate, and concentrate in vacuo. Purify by flash column chromatography (silica gel, eluting with the appropriate mixture of methylene chloride/chloroform/methanol/concentrated aqueous ammonium hydroxide) and concentrate in vacuo to provide the final compound.

Preparation 33

General Suzuki Coupling Method D

Add 2-(pyridin-2-yl)-5,6-dihydro-4H-pyrrolo[1,2-b]pyrazole-3-boronic acid (1.0 eq), the hetroaryl halide (1.0-1.2 eq), sodium bicarbonate (2.0 eq), tetrakis(triphenylphosphine) palladium(0) (Strem; 0.02-0.05 eq), acetonitrile (0.1M), and water (0.1M) to a round-bottom flask. Heat the reaction to 85° C. for 1-2 h. Cool the reaction mixture to room temperature. Extract the reaction mixture with chloroform (3×25 mL), dry the combined extracts with sodium sulfate, and concentrate in vacuo. Purify by flash column chromatography (silica gel, eluting with the appropriate mixture of methylene chloride/chloroform/methanol/concentrated aqueous ammonium hydroxide) and concentrate in vacuo to provide the final compound.

EXAMPLE 1

Preparation of 2-(Pyridin-2-yl)-3-(thiophen-2-yl)-5,6-dihydro-4H-pyrrolo[1,2-b]pyrazole

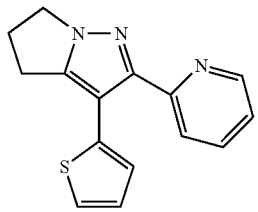

Add 3-bromo-2-(pyridin-2-yl)-5,6-dihydro-4H-pyrrolo[1,2-b]pyrazole (Preparation 4, 250 mg, 0.95 mmol) and anhydrous THF (2.5 mL) to a round bottom flask under nitrogen atmosphere. Purge the reaction flask with nitrogen for 10 min. Add tris(dibenzylideneacetone)dipalladium(0) (87 mg, 0.095 mmol) and bis(1,2-bis(diphenylphosphino)ethane) palladium(0) (86 mg, 0.095 mmol) to the reaction flask, purge with nitrogen for 2 min, and then stir at room temperature for 20 min. Add thiophene-2-boronic acid (Maybridge; 120 mg, 0.95 mmol) in DMF (1 mL) to the reaction and stir for 10 min. Add 2M aqueous potassium carbonate (1.11 mL, 2.3 mmol) and heat the reaction mixture to 65° C. Add additional tris (dibenzylideneacetone) dipalladium(0) (87 mg, 0.095 mmol) to the reaction after 1 h, 3 h, and 5 h. Heat the reaction for a total of 20 h, cool to room temperature, and filter through Celite® with chloroform/methanol (250 mL, 1:1 ratio). Concentrate in vacuo and purify by flash column chromatography to provide the title compound (13 mg, 5%) as a pale, yellow solid. MS ESI+ m/e 268 (M+1). $^1$H NMR (CDCl$_3$) δ 8.80-8.72 (m, 1H), 7.80-7.56 (m, 2H), 7.31-7.20 (m, 2H), 7.12-7.03 (m, 1H), 7.01-6.95 (m, 1H), 4.31-4.19 (m, 2H), 3.11-3.05 (m, 2H), 2.79-2.60 (m, 2H). HPLC: 98.0%, R$_t$=15.25 min. TLC (SiO$_2$): R$_f$ 0.4 (5:95 methanol/dichloromethane).

EXAMPLE 2

Preparation of 5-[2-(Pyridin-2-yl)-5,6-dihydro-4H-pyrrolo[1,2-b]pyrazol-3-yl]-1H-indole

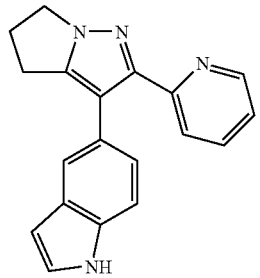

In a similar fashion to Example 1, react 1H-indole-5-boronic acid (Fluka; 150 mg, 0.95 mmol) with 3-bromo-2-(pyridin-2-yl)-5,6-dihydro-4H-pyrrolo[1,2-b]pyrazole (Preparation 4; 250 mg, 0.95 mmol) to provide the title compound (10 mg, 4%) as an off-white solid. MS ESI+ m/e 301 (M+1). $^1$H NMR (CDCl$_3$) δ 8.67-8.58 (m, 1H), 7.61 (s, 1H), 7.52-7.45 (m, 1H), 7.39-7.29 (m, 2H), 7.21-7.16 (m, 1H), 7.14-7.04 (m, 2H), 6.52-6.48 (m, 1H), 4.31-4.21 (m, 2H), 3.06-2.98 (m, 2H), 2.73-2.60 (m, 2H). TLC (SiO$_2$): R$_f$ 0.4 (1:3 [80:18:2 chloroform/methanol/concentrated aqueous ammonium hydroxide]/dichloromethane).

EXAMPLE 3

Preparation of 3-(2-Phenyl-oxazol-5-yl)-2-(pyridin-2-yl)-5,6-dihydro-4H-pyrrolo[1,2-b]pyrazole

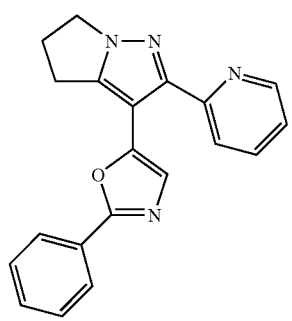

In a similar fashion to Example 1, react 5-bromo-2-phenyloxazole (Combi-Blocks; 120 mg, 0.52 mmol) with 2-(pyridin-2-yl)-5,6-dihydro-4H-pyrrolo[1,2-b]pyrazole-3-boronic acid (Preparation 5; 120 mg, 0.52 mmol) to provide the title compound (20 mg, 12%) as a white solid. MS ESI+ m/e 329 (M+1). $^1$H NMR (CDCl$_3$) δ 8.78-8.70 (m, 1H), 8.05-7.99 (m, 2H), 7.95-7.89 (m, 1H), 7.82 (s, 1H), 7.81-7.70 (m, 1H), 7.50-7.41 (m, 3H), 7.30-7.25 (m, 1H), 4.31-4.21 (m, 2H), 3.38-3.24 (m, 2H), 2.82-2.66 (m, 2H). HPLC: 97.2%, $R_t$=16.67 min. TLC (SiO$_2$): $R_f$ 0.3 (1:3 [80:18:2 chloroform/methanol/concentrated aqueous ammonium hydroxide]/dichloromethane).

EXAMPLE 4

Preparation of 4-[2-(Pyridin-2-yl)-5,6-dihydro-4H-pyrrolo[1,2-b]pyrazol-3-yl]-benzo [2,1,3]thiadiazole

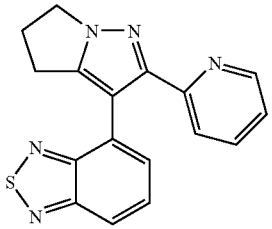

Add 4-iodo-[2,1,3]-benzothiadiazole (Maybridge; 350 mg, 1.3 mmol), 2-(pyridin-2-yl)-5,6-dihydro-4H-pyrrolo[1,2-b]pyrazole-3-boronic acid (Preparation 5; 300 mg, 1.3 mmol), potassium fluoride (250 mg, 4.3 mmol), and THF (6.0 mL) to a flask under nitrogen. Purge the system with nitrogen for 10 min and add tris(dibenzylideneacetone) dipalladium (0) (120 mg, 0.13 mmol) and tri-tert-butylphosphonium tetrafluoroborate (Strem; 100 mg, 0.039 mmol). Purge the system with nitrogen for 2 min and stir for 48 h at 45° C. Filter the reaction through Celite®, rinse with chloroform/methanol, and concentrate in vacuo. Purify by flash column chromatography followed by reverse-phase preparative HPLC. Collect the pure fractions from the HPLC, concentrate in vacuo, take up the residue in methanol, and treat with MP-carbonate beads. Filter and concentrate in vacuo to provide the title compound (46 mg, 11%) as a pale yellow solid. Melting Range: 140-142° C. MS APCI m/e 320 (M+1). $^1$H NMR (CDCl$_3$): δ 8.44-8.37 (m, 1H), 7.95-7.89 (m, 1H), 7.60-7.49 (m, 3H), 7.48-7.41 (m, 1H), 7.12-7.02 (m, 1H), 4.37-4.28 (m, 2H), 3.09-2.99 (m, 2H), 2.72-2.60 (m, 2H). HPLC: 98.3%, $R_t$=15.03 min. TLC (SiO$_2$): $R_f$ 0.3 (1:1 [80:18:2 chloroform/methanol/concentrated aqueous ammonium hydroxide]/dichloromethane).

EXAMPLE 5

Preparation of 5-[2-(Pyridin-2-yl)-5,6-dihydro-4H-pyrrolo[1,2-b]pyrazol-3-yl]benzo[2,1,3]thiadiazole

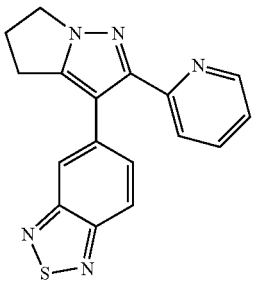

In a similar fashion to Example 4, react 5-bromo-[2,1,3]-benzothiadiazole (Maybridge; 180 mg, 0.83 mmol) with 2-(pyridin-2-yl)-5,6-dihydro-4H-pyrrolo[1,2-b]pyrazole-3-boronic acid (Preparation 5; 190 mg, 0.83 mmol) to provide the title compound (65 mg, 16%) as a tan solid. Melting Range: 184-186° C. MS ESI+ m/e 320 (M+1). $^1$H NMR (CDCl$_3$) δ 8.61-8.52 (m, 1H), 7.94 (s, 1H), 7.89-7.82 (m, 1H), 7.70-7.62 (m, 2H), 7.52-7.49 (m, 1H), 7.29-7.17 (m, 1H), 4.33-4.22 (m, 2H), 3.12-3.02 (m, 2H), 2.72-2.60 (m, 2H). HPLC: >99%, $R_t$=15.41 min. TLC (SiO$_2$): $R_f$ 0.3 (1:1 [80:18-2 chloroform/methanol/concentrated aqueous ammonium hydroxide]/dichloromethane).

EXAMPLE 6

Preparation of 6-[2-(Pyridin-2-yl)-5,6-dihydro-4H-pyrrolo[1,2-b]pyrazol-3-yl]-quinoxaline

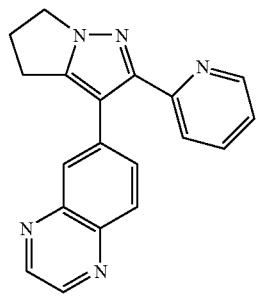

Add THF (2.2 mL) to 6-bromo-quinoxaline (Yamamoto, T. et al., J. Am. Chem. Soc. 1996, 118, 3930-3936; 219 mg, 1.05 mmol) and purge the solution with nitrogen for 10 min. Add tris(dibenzylideneacetone)dipalladium(0) (80 mg, 0.087 mmol) and bis(1,2-bis(diphenylphosphino)ethane)palladium (0) (78 mg, 0.087 mmol), purge the reaction with nitrogen for 2 min, and stir the reaction at room temperature for 20 min. Add (2-pyridin-2-yl)-5,6-dihydro-4H-pyrrolo[1,2-b]pyrazole-3-boronic acid (Preparation 5; 200 mg, 0.87 mmol) in 1:1 DMF/THF (2 mL each) and stir for 10 min. Add 2.0M aqueous potassium carbonate (1.04 mL, 2.1 mmol) and heat the reaction to 65° C. Add additional tris(dibenzylideneacetone)dipalladium(0) (80 mg, 0.087 mmol) after 1 h and 3 h. Stir the reaction at 65° C. for 18 h, filter through Celite® with methanol/chloroform, and concentrate in vacuo. Purify by flash column chromatography followed by reverse-phase preparative HPLC. Concentrate the pure fractions from the preparative HPLC in vacuo, take up in methanol, treat with MP-carbonate beads, filter, and concentrate in vacuo to provide the title compound (82 mg, 30%) as a clear, colorless oil. MS ESI+ m/e 314 (M+1). $^1$H NMR (CDCl$_3$) δ 8.86 (m, 3H), 8.11 (m, 1H), 8.05 (m, 2H), 7.79 (m, 2H), 7.47 (m, 1H), 4.33 (m, 2H), 3.11 (m, 2H), 2.72 (m, 2H). HPLC: 98.5%, $R_t$=13.61 min. TLC (SiO$_2$): $R_f$ 0.3 (1:3 [80:18:2 chloroform/methanol/concentrated aqueous ammonium hydroxide]/dichloromethane).

EXAMPLE 7

Preparation of 5-[2-(Pyridin-2-yl)-5,6-dihydro-4H-pyrrolo[1,2-b]pyrazol-3-yl]-quinoxaline

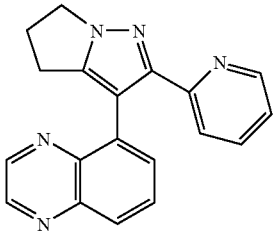

A. Preparation of Trifluoro-methanesulfonic Acid Quinoxalin-5-yl Ester

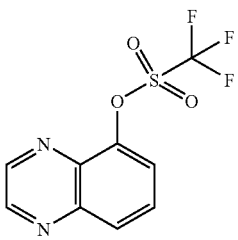

Add trifluoromethanesulfonic anhydride (0.66 mL, 3.94 mmol) to a solution of quinoxalin-5-ol (Yamamoto, T. et al., J. Am. Chem. Soc. 1996, 118, 3930-3936; 500 mg, 3.42 mmol) in pyridine (6.8 mL) at 0° C. Allow the reaction to warm slowly to room temperature over 18 h. Add saturated aqueous sodium bicarbonate solution (100 mL) and extract the mixture with methylene chloride (3×100 mL). Dry the combined organic solutions with sodium sulfate, concentrate in vacuo, and purify by flash column chromatography to provide the subtitled compound (810 mg, 85%) as an off-white solid. MS ESI+ m/e 279 (M+1). $^1$H NMR (CDCl$_3$): δ 8.85 (m, 2H), 8.18 (m, 1H), 7.84 (m, 1H), 7.63 (m, 1H). TLC (SiO$_2$): R$_f$ 0.2 (3:1 hexanes/ethyl acetate).

B. Preparation of 5-[2-(Pyridin-2-yl)-5,6-dihydro-4H-pyrrolo[1,2-b]pyrazol-3-yl]-quinoxaline Add THF (2.2 mL) to trifluoro-methanesulfonic acid quinoxalin-5-yl ester (292 mg, 1.05 mmol) and purge the solution with nitrogen for 10 min. Add tris(dibenzylideneacetone)dipalladium(0) (80 mg, 0.087 mmol) and bis(1,2-bis(diphenylphosphino)ethane)palladium(0) (78 mg, 0.087 mmol), purge the reaction with nitrogen for 2 min, and stir the reaction at room temperture for 20 min. Add 2-(pyridin-2-yl)-5,6-dihydro-4H-pyrrolo[1,2-b]pyrazole-3-boronic acid (Preparation 5; 200 mg, 0.87 mmol) in 1:1 DMF/THF (2 mL) and stir for 10 min. Add 2.0M aqueous potassium carbonate (1.04 mL, 2.1 mmol) and heat the reaction to 65° C. Add additional tris(dibenzylideneacetone)dipalladium(0) (80 mg, 0.087 mmol) after 1 h and 3 h. Stir the reaction at 65° C. for 18 h, filter through Celite® with methanol/chloroform, and concentrate in vacuo. Purify by flash column chromatography followed by reverse-phase preparative HPLC. Concentrate the pure fractions from the preparative HPLC in vacuo, take up in methanol, treat with MP-carbonate beads, filter, and concentrate in vacuo to provide the title compound (11 mg, 7%) as a clear, colorless oil. MS APCI+ m/e 314 (M+1). $^1$H NMR (DMSO-d$_6$) δ 8.78 (m, 1H), 8.68 (m, 1H), 8.54 (m, 1H), 8.08 (m, 1H), 7.72 (m, 3H), 7.53 (m, 1H), 7.22 (m, 1H), 4.37 (m, 2H), 2.95 (m, 2H), 2.64 (m, 2H). HPLC: 98.6%, R$_t$=13.5 min. TLC (SiO$_2$): R$_f$ 0.2 (1:3 [80:18:2 chloroform/methanol/concentrated aqueous ammonium hydroxide]/dichloromethane).

EXAMPLE 8

Preparation of 2-[2-(Pyridin-2-yl)-5,6-dihydro-4H-pyrrolo[1,2-b]pyrazol-3-yl]-1H-imidazo[4,5-b]pyridine

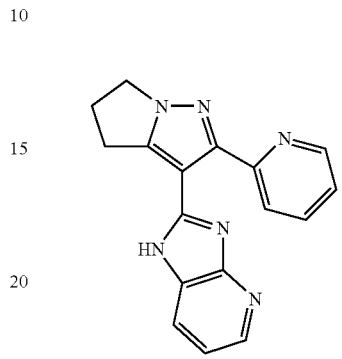

Add 2,3-diaminopyridine (Fluka; 120 mg, 1.09 mmol) and phosphorous oxychloride (4.4 mL) to 2-(pyridin-2-yl)-5,6-dihydro-4H-pyrrolo[1,2-b]pyrazole-3-carboxylic acid (Preparation 3; 251 mg, 1.09 mmol) and heat the reaction at 106° C. for 3 h. Cool the reaction to 0° C. and add 1N aqueous hydrochloric acid (10 mL) slowly and stir for 10 min. Neutralize the mixture with saturated aqueous sodium bicarbonate and extract with chloroform. Wash the combined organic layers with brine, dry with sodium sulfate, concentrate in vacuo, purify by flash column chromatography, and triturate with hexanes to provide the title compound (159 mg, 48%) as a tan solid. Mp 170-172° C. MS ESI+ m/e 303 (M+1). $^1$H NMR (CDCl$_3$) δ 8.80 (br, 1H), 8.34 (m, 2H), 7.88 (m, 2H), 7.36 (m, 1H), 7.11 (m, 1H), 4.29 (m, 2H), 3.54 (m, 2H), 2.71 (m, 2H). HPLC: 96.3%, R$_t$=13.59 min. TLC (SiO$_2$): R$_f$ 0.3 (1:3 [80:18:2 chloroform/methanol/concentrated aqueous ammonium hydroxide]/dichloromethane).

EXAMPLE 9

Preparation of 2-[2-(Pyridin-2-yl)-5,6-dihydro-4H-pyrrolo[1,2-b]pyrazol-3-yl]-1H-imidazo[4,5-c]pyridine

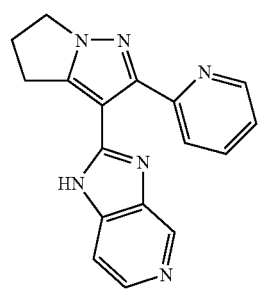

In a similar fashion to Example 8, react 3,4-diaminopyridine (commercially available e.g. Fluka; 120 mg, 1.1 mmol) and phosphorous oxychloride (4.4 mL) with 2-(pyridin-2-yl)-5,6-dihydro-4H-pyrrolo[1,2-b]pyrazole-3-carboxylic acid (Preparation 3; 250 mg, 1.1 mmol) to provide the title compound (30 mg, 10%) as a tan solid. Mp 201-203° C. MS ESI+ m/e 303 (M+1). $^1$H NMR (DMSO-d$_6$) δ 9.02 (m, 1H), 8.75 (m, 1H), 8.31 (m, 2H), 7.90 (m, 1H), 7.65 (m, 1H), 7.41 (m, 2H), 4.29 (m, 2H), 3.51 (m, 2H), 2.77 (m, 2H). HPLC: 94.6%, R$_t$=12.6 min. TLC (SiO$_2$): R$_f$ 0.3 (1:1 [80:18:2 chloroform/methanol/concentrated aqueous ammonium hydroxide]/dichloromethane).

EXAMPLE 10

Preparation of 2-[2-(Pyridin-2-yl)-5,6-dihydro-4H-pyrrolo[1,2-b]pyrazol-3-yl]-1H-benzoimidazole

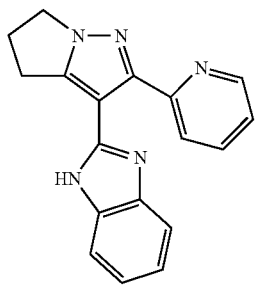

In a similar fashion to Example 8, react 1,2-phenylenediamine (Fluka; 120 mg, 1.1 mmol) and phosphorous oxychloride (4.4 mL) with 2-pyridin-2-yl)-5,6-dihydro-4H-pyrrolo[1,2-b]pyrazole-3-carboxylic acid (Preparation 3, 250 mg, 1.1 mmol) to provide the title compound (68 mg, 21%) as a brown solid. Mp 172-175° C. MS ESI+ m/e 302 (M+1). $^1$H NMR (CDCl$_3$) δ 8.78 (m, 1H), 8.30 (m, 1H), 7.86 (m, 1H), 7.71 (m, 1H), 7.55 (m, 1H), 7.33 (m, 1H), 7.15 (m, 2H), 4.14 (m, 2H), 3.49 (m, 2H), 2.71 (m, 2H). HPLC: 98.6%, R$_t$=16.89 min. TLC (SiO$_2$): R$_f$ 0.4 (1:1 [80:18:2 chloroform/methanol/concentrated aqueous ammonium hydroxide]/dichloromethane).

EXAMPLE 11

Preparation of 2-[2-(Pyridin-2-yl)-5,6-dihydro-4H-pyrrolo[1,2-b]pyrazol-3-yl]-oxazolo[4,5-b]pyridine

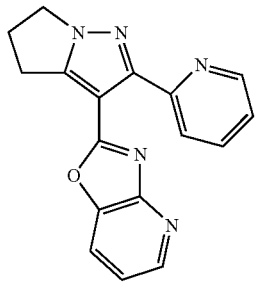

In a similar fashion to Example 8, react 2-amino-3-hydroxypyridine (Fluka; 144 mg, 1.3 mmol) and phosphorous oxychloride (4.4 mL) with 2-(pyridin-2-yl)-5,6-dihydro-4H-pyrrolo[1,2-b]pyrazole-3-carboxylic acid (Preparation 3; 250 mg, 1.1 mmol) to provide the title compound (74 mg, 22%) as a tan solid. Mp 182-184° C. MS ESI+ m/e 304 (M+1). $^1$H NMR (CDCl$_3$) δ 8.75 (m, 1H), 8.52 (m, 1H), 8.12 (m, 1H), 7.84 (m, 1H), 7.69 (m, 1H), 7.32 (m, 1H), 7.15 (m, 1H), 4.31 (m, 2H), 7.37 (m, 2H), 2.75 (m, 2H). HPLC: 98.3%, R$_t$=13.95 min. TLC (SiO$_2$): R$_f$ 0.4 (1:3 [80:18:2 chloroform/methanol/concentrated aqueous ammonium hydroxide]/dichloromethane).

EXAMPLE 12

Preparation of 2-Dimethylamino-N-[6-[2-(pyridin-2-yl)-5,6-dihydro-4H-pyrrolo[1,2-b]pyrazol-3-yl]-[1,8]naphthyridin-2-yl]-acetamide

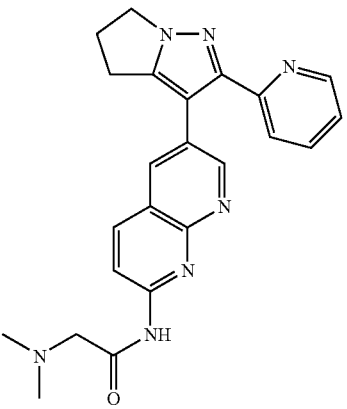

A. Preparation of N-(6-Bromo-[1,8]naphthyridin-2-yl)-2-dimethylamino-acetamide

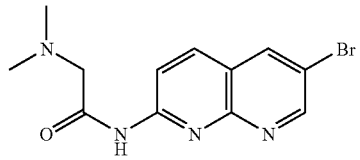

Add N,N-dimethylglycine (0.28 g, 2.68 mmol), 1-ethyl-3-(3-dimethylaminopropyl)-carbodiimide (0.47 g, 2.45 mmol), 1-hydroxybenzotriazole (0.33 g, 2.45 mmol), and methylene chloride (111 mL) to 6-bromo-[1,8]naphthyridin-2-ylamine (Reichardt, C. et al, *Tetrahedron Lett.* 1977, 2087; 0.50 g, 2.23 mmol). Stir the reaction at room temperature for 19 h, concentrate in vacuo and purify by flash column chromatography to provide the subtitled compound (0.41 g, 60%) as an orange solid. MS ESI+ m/e 309/311 (M+1). $^1$H NMR (DMSO-d$_6$) δ 10.52 (m, 1H), 8.96 (m, 1H), 8.71 (m, 1H), 8.35 (m, 2H), 3.15 (s, 2H), 2.25 (s, 6H). TLC (SiO$_2$): R$_f$ 0.3 (1:4 [80:18:2 chloroform/methanol/concentrated aqueous ammonium hydroxide]/dichloromethane).

B. Preparation of 2-Dimethylamino-N-16-[2-(pyridin-2-yl)-5,6-dihydro-4H-pyrrolo[1,2-b]pyrazol-3-yl]-[1,8]naphthyridin-2-yl]-acetamide Add N-(6-bromo-[1,8]naphthyridin-2-yl)-2-dimethylamino-acetamide (148 mg, 0.48 mmol), 2-(pyridin-2-yl)-5,6-dihydro-4H-pyrrolo[1,2-b]pyrazole-3-boronic acid (Preparation 5; 100 mg, 0.44 mmol), potassium fluoride (84 mg, 1.45 mmol), and THF (1.5 mL) to a flask under nitrogen. Purge the system with nitrogen for 10 min and add tris(dibenzylideneacetone)dipalladium(0) (40 mg, 0.044 mmol) and tri-tert-butylphosphonium tetrafluoroborate (Strem; 25 mg, 0.088 mmol). Purge the system with nitrogen for 2 min then stir for 16 h at room temperature. Add additional tris(dibenzylideneacetone)dipalladium(0) (50 mg, 0.054 mmol) and tri-tert-butylphosphonium tetrafluoroborate (40 mg, 0.138 mmol) and heat the reaction to 65° C. for 9 h. Filter the reaction through Celite®, rinse with chloroform/methanol, and concentrate in vacuo. Purify by flash column chromatography followed by reverse-phase preparative HPLC. Collect the pure fractions from the HPLC, concentrate in vacuo, take up the residue in methanol, and treat with MP-carbonate beads. Filter, concentrate in vacuo, and triturate with hexanes to provide the title compound (10 mg, 5%) as a tan solid. MS ESI+ m/e 414 (M+1). $^1$H NMR (CDCl$_3$) δ 10.21 (m, 1H), 8.93 (m, 1H), 8.48 (m, 2H), 8.09 (m, 2H), 7.68 (m, 2H), 7.20 (m, 1H), 4.27 (m, 2H), 3.17 (m, 4H), 2.72 (m, 2H), 2.41 (s, 6H). HPLC: 95.1%, R$_t$=11.21 min. TLC (SiO$_2$): R$_f$0.3 (1:1 [80:18:2 chloroform/methanol/concentrated aqueous ammonium hydroxide]/dichloromethane)

EXAMPLE 13

Preparation of 4-[2-(Pyridin-2-yl)-5,6-dihydro-4H-pyrrolo[1,2-b]pyrazol-3-yl]-[1,8]naphthyridine

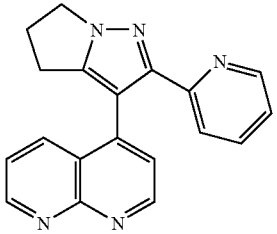

Add THF (1 mL) to 4-bromo-[1,8]naphthyridine (Barlin, G. B. and Tan, W-L. *Australian J. Chem.* 1984, 37, 1065-1073; 66 mg, 0.31 mmol) and purge the solution with nitrogen for 10 min. Add tris(dibenzylideneacetone)dipalladium(0) (24 mg, 0.026 mmol) and bis(1,2-bis(diphenylphosphino) ethane) palladium(0) (24 mg, 0.026 mmol), purge the reaction mixture with nitrogen for 2 min, and stir the reaction at room temperature for 20 min. Add 2-(pyridin-2-yl)-5,6-dihydro-4H-pyrrolo[1,2-b]pyrazole-3-boronic acid (Preparation 5, 60 mg, 0.26 mmol) in 1:1 DMF/THF (1 mL) and stir for 10 min. Add 2.0 M aqueous potassium carbonate (0.32 mL, 0.63 mmol) and heat the reaction to 40° C. Add additional tris (dibenzylideneacetone)dipalladium(0) (24 mg, 0.026 mmol) after 1 h and 3.5 h. Stir the reaction at 40 DC for 24 h and concentrate in vacuo. Load the crude reaction mixture onto SCX resin with methanol, wash the resin with methanol (100 mL), and elute with methanolic ammonia solution (2M, 100 mL). Concentrate the ammonia fraction in vacuo, purify by flash column chromatography and triturate with hexanes to provide the title compound (28.7 mg, 35%) as a tan solid. MS ESI+ m/e 314 (M+1). $^1$H NMR (CDCl$_3$) δ 9.11 (m, 1H), 9.07 (m, 1H), 8.25 (m, 1H), 8.10 (m, 1H), 7.35-7.50 (m, 3H), 7.04 (m, 2H), 4.38 (m, 2H), 2.88 (m, 2H), 2.70 (m, 2H). HPLC: 94.8%, R$_t$=6.75 min. TLC (SiO$_2$): R$_f$0.3 (1:1 [80:18:2 chloroform/methanol/concentrated aqueous ammonium hydroxide]/dichloromethane).

EXAMPLE 14

Preparation of 2-(Pyridin-2-yl)-3-(imidazo[1,2-a] pyridin-6-yl)-5,6-dihydro-4H-pyrrolo[1,2-b]pyrazole

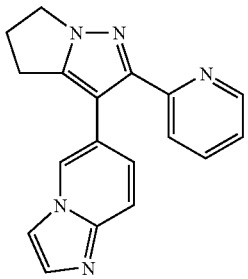

A. Preparation of 6-Bromo-imidazo[1,2-a]pyridine

Reflux a solution of 2-amino-5-bromo-pyridine (Maybridge; 1.0 g, 5.78 mmol), 50% aqueous chloroacetaldehyde (2 mL, 12.7 mmol) in acetonitrile (100 mL) for 14 h. Dilute the reaction with saturated aqueous sodium bicarbonate and extract into ethyl acetate. Flash chromatography using appropriate ethyl acetate/hexane mixtures gives 0.95 g (83%) of the subtitled compound as a tan solid. MS (electrospray, m/z) 196.7, 198.7 (M+1). $^1$H NMR (400 MHz, DMSO-d$_6$) δ 8.9 (d, J=1.5 Hz, 1H), 7.90 (s, 1H), 7.58 (d, J=1.5 Hz, 1H), 7.53 (d, J=9.2 Hz, 1H), 7.29 (dd, J=9.2, 2 Hz, 1H).

B. Preparation of 2-(Pyridin-2-yl)-3-(imidazo[1,2-a] pyridin-6-yl)-5,6-dihydro-4H-pyrrolo[1,2-b]pyrazole Add tetrakis(triphenylphosphine)palladium(0) (0.025 g, 0.022 mmol) to a microwave tube containing a solution of 6-bromo-imidazo[1,2-a]pyridine (0.086 g, 0.44 mmol), 2-pyridin-2-yl)-5,6-dihydro-4H-pyrrolo[1,2-b]pyrazole-3-boronic acid (Preparation 5; 0.1 g, 0.436 mmol), and 2M aqueous potassium carbonate (0.5 mL, 1 mmol) in dimethylsulfoxide (1.5 mL). Irradiate the reaction in a microwave reactor set at 111° C., 50 W., 10 min with internal cooling. Normal phase chromatography using ethyl acetate/methanol mixtures followed by reversed phase preparative chromatography gives the 0.05 g (38%) of the title compound as a white solid. MS (electrospray, m/z) 301.9 (M+1). $^1$H NMR (400 MHz, DMSO-d) δ 8.57 (s, 1H), 8.4 (d, J=4.8 Hz, 1H), 7.87 (s, 1H), 7.78 (m, 2H), 7.52 (s, 1H), 7.42 (d, J=9.2 Hz, 1H), 7.26 (m, 1H), 7.05 (dd, J=9.2, 2 Hz, 1H), 4.2 (t, J=6.6 Hz, 2H), 2.99 (t, J=6.6 Hz, 2H), 2.59 (m, 1H).

EXAMPLE 14a

Alternative preparation of 2-(Pyridin-2-yl)-3-(imidazo[1,2-a]pyridin-6-yl)-5,6-dihydro-4H-pyrrolo[1,2-b]pyrazole

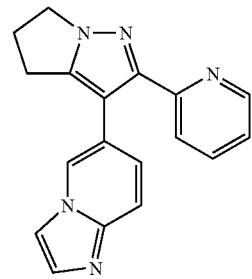

A. Preparation of 6-Iodo-imidazo[1,2-a]pyridine

Reflux a solution of 2-amino-5-iodo-pyridine (*Tetrahedron* 2002, 58, 2885-2890; 1.5 g, 6.82 mmol) and 50% aqueous chloroacetaldehyde (1.56 mL, 12.3 mmol) in acetonitrile (150 mL) for 14 h. Cool, concentrate, and dissolve the residue in 1:1 saturated aqueous sodium bicarbonate/dichloromethane. Extract the aqueous layer with dichloromethane, combine the organic layers, and concentrate. Flash chromatography using appropriate ethyl acetate/methanol mixtures gives 1.1 g (66%) of the subtitled compound as a light green solid. TOF MS ES+ exact mass calculated for C$_7$H$_{51}$N$_2$ (p+1): m/z=244.9576; Found: 244.9564. $^1$H NMR (400 MHz, DMSO-d$_6$) δ 8.9 (s, 1H), 7.86 (s, 1H), 7.52 (s, 1H), 7.40 (d, J=9 Hz, 1H), 7.36 (d, J=9.2, H).

B. Preparation of 2-(Pyridin-2-yl)-3-(imidazo[1,2-a]pyridin-6-yl)-5,6-dihydro-4H-pyrrolo[1,2-b]pyrazole Add tetrakis(triphenylphosphine)palladium(0) (0.58 g, 0.5 mmol) to a 2 L flask containing a solution of 6-iodo-imidazo[1,2-a]pyridine (6.16 g, 25.2 mmol), 2-(pyridin-2-yl)-5,6-dihydro-4H-pyrrolo[1,2-b]pyrazole-3-boronic acid (Preparation 5; 6.07 g, 26.5 mmol), and sodium bicarbonate (4.24 g, 50.5 mmol) in 2.5:1 acetonitrile:water (700 mL). Reflux the reaction mixture for 3 h, cool, concentrate to about one half of the volume, extract into dichloromethane (4×250 ml), and concentrate. Flash chromatography using a gradient from 100% hexanes to 100% ethyl acetate (10 min, 45 ml/min), followed by isocratic 100% ethyl acetate (2 L), removes most impurities. Elution with ethyl acetate/methanol mixtures followed by tituration in hot ethyl acetate affords the title compound as a white solid 5.46 g, (72%). MS ES+ m/e 301.9 (M+1). $^1$H-NMR (400 MHz, DMSO-$d_6$) δ 8.56 (s, 1H), 8.39 (d, J=3.2 Hz, 1H), 7.87 (s, 1H), 7.81-7.76 (m, 2H), 7.51 (d, J=1.2, 1H), 7.42 (d, J=9.2 Hz, 1H), 7.26 (m, 1H), 7.05 (dd, J=9.2, 2 Hz, 1H), 4.2 (t, J=6.6 Hz, 2H), 2.99 (t, J=6.6 Hz, 2H), 2.59 (m, 1H).

EXAMPLES 15-29

General Suzuki Coupling Method E

Combine either 3-bromo-2-(6-methyl-pyridin-2-yl)-5,6-dihydro-4H-pyrrolo[1,2-b]pyrazole (Preparation 1) or 3-bromo-2-(pyridin-2-yl)-5,6-dihydro-4H-pyrrolo[1,2-b]pyrazole (Preparation 4, 1.0 eq) with a substituted aryl- or heteroarylboronic acid (1.0 eq-3.0 eq) in the presence of a suitable palladium catalyst, preferably tris(dibenzylidineacetone)dipalladium(0) (0.03 eq-0.10 eq), a suitable ligand, preferably (biphenyl-2-yl)-di-tert-butyl-phosphane (0.06 eq-0.12 eq), and a suitable base, preferably cesium fluoride (2 eq-3 eq) in a 4:1 toluene/ethanol mixture in a 10 mL glass tube. A substituted aryl- or heteroarylhalide can be combined with the 3-boronic acid analog of the 3-bromo-dihydro-pyrrolo-pyrazole in the same manner. Seal the reaction vessel with a septum and place in the microwave cavity. Use microwave irradiation of 35-150 W to raise the temperature to 80-130° C. over 90-120 seconds. Hold at the desired temperature for 5-30 min. Cool the reaction vessel to room temperature before opening. Add the reaction mixture to SCX resin, elute with dichloromethane, methanol, and then 2.0M ammonia in methanol. Concentrate the methanolic ammonia fraction to dryness under reduced pressure. Chromatograph the residue on silica gel eluting with 20% ethyl acetate/80% hexanes, 40% ethyl acetate/60% hexanes, 60% ethyl acetate/40% hexanes, and 5% methanol/95% ethyl acetate to provide the desired product.

The following compounds were prepared utilizing the General Suzuki Coupling Methods.

| Example | Product | Starting Material A | Starting Material B | Physical Data | Comments |
|---|---|---|---|---|---|
| 15 | 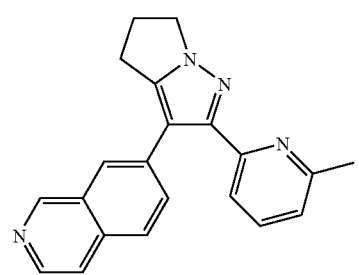<br>7-[2-(6-methyl-pyridin-2-yl)-5,6-dihydro-4H-pyrrolo[1,2-b]pyrazol-3-yl]-isoquinoline | 7-iodo-isoquinoline (Preparation 6) | 2-(6-methyl-pyridin-2-yl)-5,6-dihydro-4H-pyrrolo[1,2-b]pyrazole-3-boronic acid (Preparation 2) | MS (ES) m/e 327 (M+) | General Suzuki Coupling Method E |
| 16 | 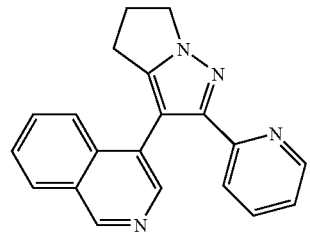<br>4-[2-(pyridin-2-yl)-5,6-dihydro-4H-pyrrolo[1,2-b]pyrazol-3-yl]-isoquinoline | 4-iodo-isoquinoline (Preparation 7) | 2-(pyridin-2-yl)-5,6-dihydro-4H-pyrrolo[1,2-b]pyrazole-3-boronic acid (Preparation 5) | MS (ES) m/e 313 (M+) | Example 15 (General Suzuki Coupling Method E) |

-continued

| Example | Product | Starting Material A | Starting Material B | Physical Data | Comments |
|---|---|---|---|---|---|
| 17 | 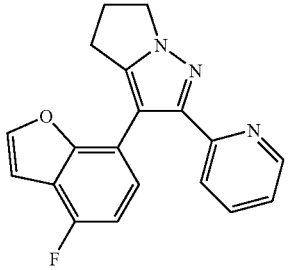<br>3-(4-fluoro-benzofuran-7-yl)-2-(pyridin-2-yl)-5,6-dihydro-4H-pyrrolo[1,2-b]pyrazole | 4-fluoro-7-iodo-benzofuran (Preparation 8) | 2-(pyridin-2-yl)-5,6-dihydro-4H-pyrrolo[1,2-b]pyrazole-3-boronic acid (Preparation 5) | MS (ES) m/e 320 (M$^+$) | Example 15 (General Suzuki Coupling Method E) |
| 18 | 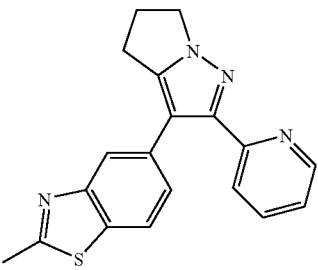<br>2-methyl-5-[2-(pyridin-2-yl)-5,6-dihydro-4H-pyrrolo[1,2-b]pyrazol-3-yl]-benzothiazole | 5-bromo-2-methyl benzothiazole (available from TCI) | 2-pyridin-2-yl-5,6-dihydro-4H-pyrrolo[1,2-b]pyrazole-3-boronic acid (Preparation 5) | MS (ES) m/e 333 (M$^+$) | Example 15 (General Suzuki Coupling Method E) |
| 19 | 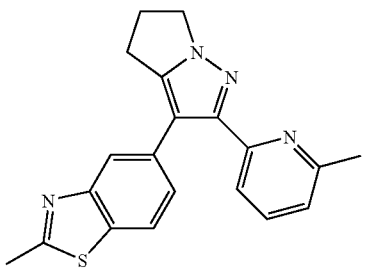<br>2-methyl-5-[2-(6-methyl-pyridin-2-yl)-5,6-dihydro-4H-pyrrolo[1,2-b]pyrazol-3-yl]-benzothiazole | 5-bromo-2-methyl-benzothiazole (available from TCI) | 2-(6-methyl-pyridin-2-yl)-5,6-dihydro-4H-pyrrolo[1,2-b]pyrazole-3-boronic acid (Preparation 2) | MS (ES) m/e 347 (M$^+$) | Example 15 (General Suzuki Coupling Method E) |

| Example | Product | Starting Material A | Starting Material B | Physical Data | Comments |
|---|---|---|---|---|---|
| 20 | 3-(4-fluoro-benzofuran-7-yl)-2-(6-methyl-pyridin-2-yl)-5,6-dihydro-4H-pyrrolo[1,2-b]pyrazole | 4-fluoro-7-iodo-benzofuran (Preparation 8) | 2-(6-methyl-pyridin-2-yl)-5,6-dihydro-4H-pyrrolo[1,2-b]pyrazole-3-boronic acid (Preparation 2) | MS (ES) m/e 334 (M+) | Example 15 (General Suzuki Coupling Method E) |
| 21 | 7-[2-(pyridin-2-yl)-5,6-dihydro-4H-pyrrolo[1,2-b]pyrazol-3-yl]-isoquinoline | 7-iodo-isoquinoline (Preparation 6) | 2-(pyridin-2-yl)-5,6-dihydro-4H-pyrrolo[1,2-b]pyrazole-3-boronic acid (Preparation 5) | MS (ES) m/e 313 (M+) | Example 15 (General Suzuki Coupling Method E) |
| 22 | 1-methyl-5-[2-(6-methyl-pyridin-2-yl)-5,6-dihydro-4H-pyrrolo[1,2-b]pyrazol-3-yl]-1H-indole | N-methylindole-5-boronic acid (available from Frontier) | 3-bromo-2-(6-methyl-pyridin-2-yl)-5,6-dihydro-4H-pyrrolo[1,2-b]pyrazole (Preparation 1) | (89 mg, 68%). ES+ m/e 330 (M + 1) | Example 15 (General Suzuk Coupling Method E) |

-continued

| Example | Product | Starting Material A | Starting Material B | Physical Data | Comments |
|---|---|---|---|---|---|
| 23 | 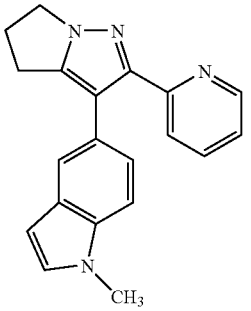<br>1-methyl-5-[2-(pyridin-2-yl)-5,6-dihydro-4H-pyrrolo[1,2-b]pyrazol-3-yl]-1H indole | N-methylindole-5-boronic acid (available from Frontier | 3-bromo-2-pyridin-2-yl-5,6-dihydro-4H-pyrrolo[1,2-b]pyrazole (Preparation 4) | 315.2 (M + 1) | Example 15 (General Suzuki Coupling Method E) |
| 24 | 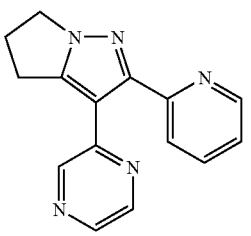<br>3-(pyrazin-2-yl)-2-(pyridin-2-yl)-5,6-dihydro-4H-pyrrolo[1,2-b]pyrazole | 2-Iodo-pyrazine (available from Frontier) | 2-(pyridin-2-yl)-5,6-dihydro-4H-pyrrolo[1,2-b]pyrazole-3-boronic acid (Preparation 5) | 264.2 (M + 1) | Example 15 (General Suzuki Coupling Method E) |
| 25 | 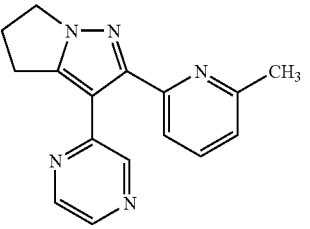<br>2-(6-methyl-pyridin-2-yl)-3-(pyrazin-2-yl)-5,6-dihydro-4H-pyrrolo[1,2-b]pyrazole | 2-iodo-pyrazine (available from Frontier) | 2-(6-methyl-pyridin-2-yl)-5,6-dihydro-4H-pyrrolo[1,2-b]pyrazole-3-boronic acid (Preparation 2) | 278.1 (M + 1) | Example 15 (General Suzuki Coupling Method E) |

-continued

| Example | Product | Starting Material A | Starting Material B | Physical Data | Comments |
|---|---|---|---|---|---|
| 26 | 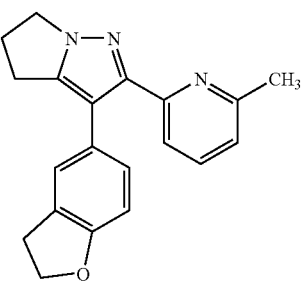<br>3-(2,3-dihydro-benzofuran-5-yl)-2-(6-methyl-pyridin-2-yl)-5,6-dihydro-4H-pyrrolo[1,2-b]pyrazole | 5-iodo-2,3-dihydro-benzofuran (available from Frontier) | 2-(6-methyl-pyridin-2-yl)-5,6-dihydro-4H-pyrrolo[1,2-b]pyrazole-3-boronic acid (Preparation 2) | 313.3 (M + 1) | Example 15 (General Suzuki Coupling Method E) |
| 27 | 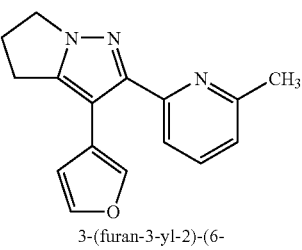<br>3-(furan-3-yl-2)-(6-methyl-pyridin-2-yl)-5,6-dihydro-4H-pyrrolo[1,2-b]pyrazole | 2-furan-3-yl-4,4,5,5-tetramethyl-[1,3,2]dioxaborolane (available from Lancaster) | 3-bromo-2-(6-methyl-pyridin-2-yl)-5,6-dihydro-4H-pyrrolo[1,2-b]pyrazole (Preparation 1) | 266 (M + 1) | Example 15 (General Suzuki Coupling Method E) |
| 28 | 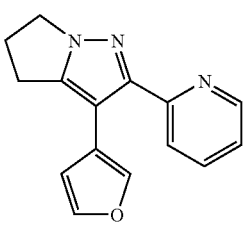<br>3-(furan-3-yl)-2-(pyridin-2-yl)-5,6-dihydro-4H-pyrrolo[1,2-b]pyrazole | 2-furan-3-yl-4,4,5,5-tetramethyl-[1,3,2]dioxaborolane (available from Lancaster) | 3-bromo-2-(pyridin-2-yl)-5,6-dihydro-4H-pyrrolo[1,2-b]pyrazole (Preparation 4) | 252.2 (M + 1) | Example 15 (General Suzuki Coupling Method E) |
| 29 | 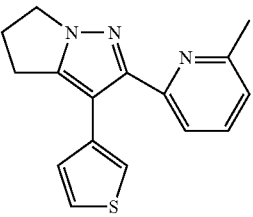<br>2-(6-methyl-pyridin-2-yl)-3-(thiophen-3-yl)-5,6-dihydro-4H-pyrrolo[1,2-b]pyrazole | 3-thiophene boronic acid (available from Maybridge) | 3-bromo-2-(6-methyl-pyridin-2-yl)-5,6-dihydro-4H-pyrrolo[1,2-b]pyrazole (Preparation 1) | 282.1 (M + 1) | Example 15 (General Suzuki Coupling Method E) |

EXAMPLE 30

Preparation of 3-(Benzofuran-5-yl)-2-(6-methyl-pyridin-2-yl)-5,6-dihydro-4H-pyrrolo[1,2-b]pyrazole

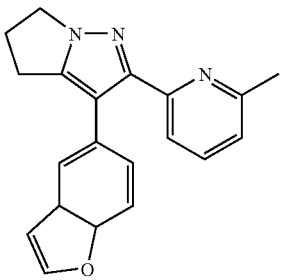

Dissolve 3-(2,3-dihydro-benzofuran-5-yl)-2-(6-methyl-pyridin-2-yl)-5,6-dihydro-4H-pyrrolo[1,2-b]pyrazole (Example 26; 10 mg, 0.03 mmol) and 2,3-dichloro-5,6-dicyanobenzoquinone (14 mg, 0.06 mmol) in anhydrous toluene (4 mL). Heat the mixture for 6 hr at 110° C. Evaporate the solvent and purify the crude product by flash chromatography to give target compound as a pale yellow solid (9 mg, 91%). MS m/e (315.2, M+1).

EXAMPLE 31

Preparation of 6-[2-(Pyridin-2-yl)-5,6-dihydro-4H-pyrrolo[1,2-b]pyrazol-3-yl]-pyrazolo[1,5-a]pyrimidine

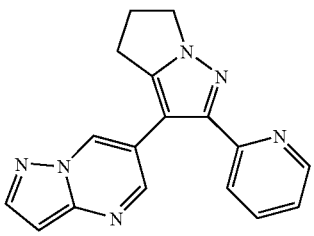

A. Preparation of 6-Bromo-pyrazolo[1,5-a]pyrimidine

Dissolve bromomalonaldehyde (Aldrich; 2.5 g, 16.5 mmol) and 3-aminopyrazole (Aldrich; 1.38 g, 16.5 mmol) in glacial acetic acid (25 mL) and reflux the resulting mixture under nitrogen for 2 h. Concentrate under reduced pressure. Dissolve the residue in absolute methanol (150 mL), vacuum filter through a pad diatomaceous earth and concentrate under reduced pressure. Chromatograph on flash silica using a gradient from neat hexane to 50% ethyl acetate/50% hexane to obtain 365 mgs (11%) of the subtitled compound as a light yellow solid. High Resolution Mass Spectrum: 197.9674 (M+1).

B. Preparation of 6-[2-(Pyridin-2-yl)-5,6-dihydro-4H-pyrrolo[1,2-b]pyrazol-3-yl]-pyrazolo[1,5-a]pyrimidine To a microwave tube, add 6-bromo-pyrazolo[1,5-a]pyrimidine (0.175 g, 0.884 mmol), 2-(pyridin-2-yl)-5,6-dihydro-4H-pyrrolo[1,2-b]pyrazole-3-boronic acid (0.25 g, 1.09 mmol), tetrakis(triphenylphosphine)palladium(0) (31 mg, 0.027 mmol), 2M aqueous potassium carbonate (0.5 mL, 1.0 mmol) and dimethylsulfoxide (1.5 mL). Irradiate the reaction in a microwave reactor set at 110° C., 50 Watts, 10 min with external cooling. Dilute the reaction mixture with diethyl ether (250 mL) and extract the product into 0.1M aqueous hydrochloric acid (450 mL). Make the aqueous solution basic by adding 5M aqueous sodium hydroxide (25 mL) and extract with dichloromethane (300 mL). Filter the organic layer and concentrate under reduced pressure. Recrystallize the resulting solid from ethyl acetate, filter, rinse with ethyl acetate, and dry at 100° C. under vacuum to obtain 70 mg (26%) of the title compound as a tan solid. MS (electrospray, m/z) 302.9 (M+1).

EXAMPLE 32

Preparation of 3-(3,4-Dihydro-2H-benzo[b][1,4]dioxepin-7-yl)-2-(pyridin-2-yl)-5,6-dihydro-4H-pyrrolo[1,2-b]pyrazole

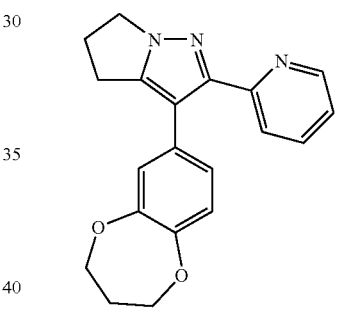

Add bis(1,2-bis(diphenylphosphino)ethane)palladium(0) (Pd(DIPHOS)$_2$; 0.086 g, 0.095 mmol) and tris(dibenzylidene-acetone)dipalladium(0) (Pd$_2$(dba)$_3$); 0.088 g, 0.095 mmol) to a degassed solution of 3-bromo-2-(pyridin-2-yl)-5,6-dihydro-4H-pyrrolo[1,2-b]pyrazole (Preparation 4, 0.25 g, 0.95 mmol) in THF (2.5 mL). Purge the reaction mixture with nitrogen for 2 min and stir for 20 min at room temperature. Add 3,4-dihydro-2H-benzo[b][1,4]dioxepin-7-ylboronic acid (158 mg, 0.95 mmol) in DMF (1 mL). After stirring the reaction mixture for 10 min, add 2M aqueous potassium carbonate solution (1.2 mL). Heat the solution at 65° C. for 1 h. Add Pd$_2$(dba)$_3$ (0.088 g, 0.095 mmol) twice after 1 h and again after 2 h. Continue stirring the reaction mixture for 15 h at 65° C. Cool the mixture to room temperature, filter through a Celite® pad, and wash the celite pad with dichloromethane (50 mL) and methanol (50 mL). Evaporate the filtrate. Purification of the residue by flash chromatography (SiO$_2$, 1:3 [88:8:2 chloroform/methanol/concentrated aqueous ammonium hydroxide]/dichloromethane) gives the title compound (69 mg, 22%) as a brown oil.

MS APC+ m/e 334 (M+1). $^1$H NMR (CDCl$_3$) δ 9.09-8.82 (m, 1H), 8.23-8.02 (m, 1H), 7.78-7.54 (m, 2H), 7.07-6.94 (m, 1H), 6.87-6.69 (m, 2H), 4.43-4.12 (m, 6H), 3.06-2.84 (m, 2H), 2.78-2.63 (m, 2H), 2.30-2.13 (m, 2H). HPLC: >97%, R$_t$=16 min.

| Example | Product | Starting Material A | Starting Material B | Physical Data | Comments |
|---|---|---|---|---|---|
| 33 | 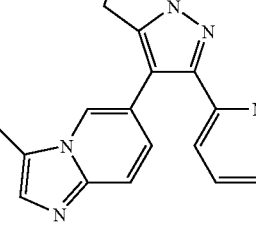<br>3-morpholin-4-ylmethyl-6-[2-(pyridin-2-yl)-5,6-dihydro-4H-pyrrolo[1,2-b]pyrazol-3-yl]-imidazo[1,2-a]pyridine | 6-bromo-3-morpholin-4-ylmethyl-imidazo[1,2-a]pyridine (Preparation 9) | 2-(pyridin-2-yl)-5,6-dihydro-4H-pyrrolo[1,2-b]pyrazole-3-boronic acid (Preparation 5) | MS ES+ m/e 401.1 (M + 1) | Example 32 |
| 34 | 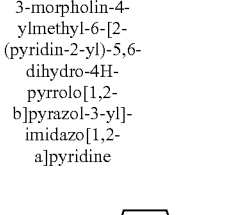<br>1-morpholin-4-yl-2-[6-(2-pyridin-2-yl-5,6-dihydro-4H-pyrrolo[1,2-b]pyrazol-3-yl)-imidazo[1,2-a]pyridin-3-yl]-ethanone | 2-(6-bromo-imidazo[1,2-a]pyridin-3-yl)-1-morpholin-4-yl-ehtanone (Preparation 10) | 2-(pyridin-2-yl)-5,6-dihydro-4H-pyrrolo[1,2-b]pyrazole-3-boronic acid (Preparation 5) | MS ES+ m/e 429.2 (M + 1) | Example 32 |
| 35 | 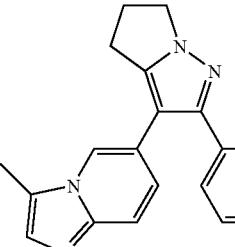<br>[2-(pyridin-2-yl)-5,6-dihydro-4H-pyrrolo[1,2-b]pyrazol-3-yl]-imidazo[1,2-a]pyridine-3-carboxylic acid ethyl ester | 6-bromo-imidazo[1,2-a]pyridine-3-carboxylic acid ethyl ester. PCT Int. Appl. (2002), WO 0288107 A1 (Preparation 14) | 2-(pyridin-2-yl)-5,6-dihydro-4H-pyrrolo[1,2-b]pyrazole-3-boronic acid (Preparation 5) | MS ES+ m/e 373.8 (M + 1) | Example 32 |

-continued

| Example | Product | Starting Material A | Starting Material B | Physical Data | Comments |
|---|---|---|---|---|---|
| 36 | 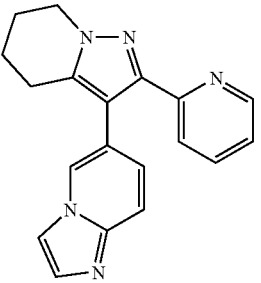<br>6-[2-(pyridin-2-yl)-4,5,6,7-tetrahydro-pyrazolo[1,5-a]pyridin-3-yl]-imidazo[1,2-a]pyridine | 6-iodo-imidazo[1,2-a]pyridine (See Example 14 a, part A) | (Preparation 5a) | MS ES+ m/e 315.8 (M + 1) | Example 32 |
| 37 | 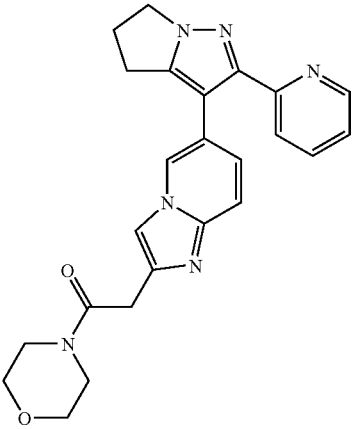<br>1-morpholin-4-yl-2-[6-(2-pyridin-2-yl)-5,6-dihydro-4H-pyrrolo[1,2-b]pyrazol-3-yl)-imidazo[1,2-a]pyridin-2-yl]-ethanone | 2-(6-bromo-imidazo[1,2-a]pyridin-2-yl)-1-morpholin-4-yl-ethanone (See preparation 11) | 2-(pyridin-2-yl)-5,6-dihydro-4H-pyrrolo[1,2-b]pyrazole-3-boronic acid (Preparation 5a). | ES MS (M + 1): 277.9 | Example 32 |
| 38 | 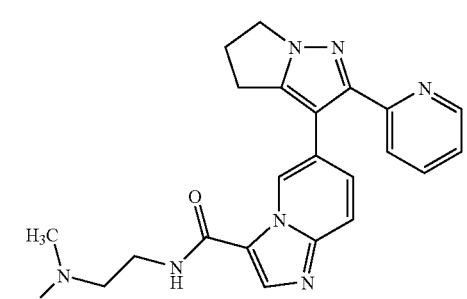<br>6-[2-(pyridin-2-yl)-5,6-dihydro-4H-pyrrolo[1,2-b]pyrazol-3-yl]-imidazo[1,2-a]pyridine-3-carboxylic acid (2-dimethylamino-ethyl)-amide | 6-bromo-imidazo[1,2-a]pyridine-3-carboxylic acid (2-dimethylamino-ethyl)-amide (Preparation 12) | 2-(pyridin-2-yl)-5,6-dihydro-4H-pyrrolo[1,2-b]pyrazole-3-boronic acid (Preparation 5) | ES MS (M + 1): 416.0 | Example 32 |

-continued

| Example | Product | Starting Material A | Starting Material B | Physical Data | Comments |
|---|---|---|---|---|---|
| 39 | 6-[2-(6-methyl-pyridin-2-yl)-5,6-dihydro-4H-pyrrolo[1,2-b]pyrazol-3-yl]-imidazo[1,2-a]pyridine-2-carboxylic acid ethyl ester | 6-iodo-imidazo[1,2-a]pyridine-2-carboxylic acid ethyl ester (Preparation 13) | 3-boronic acid-2-(6-methyl-pyridin-2-yl)-5,6-dihydro-4H-pyrrolo[1,2-b]pyrazole (Preparation 18) | ES MS (M + 1): 389.9 | Example 15 (General Suzuki Coupling Method E) |
| 40 | 6-[2-(6-methyl-pyridin-2-yl)-5,6-dihydro-4H-pyrrolo[1,2-b]pyrazol-3-yl]-imidazo[1,2-a]pyridine-2-carboxylic acid amide | Product of Example 39 | ammonia | ES MS (M + 1): 358.9 | Example 44 |
| 41 | 8-fluoro-6-[2-(pyridin-2-yl)-5,6-dihydro-4H-pyrrolo[1,2-b]pyrazol-3-yl]-imidazo[1,2-a]pyridine | 6-bromo-8-fluoro-imidazo[1,2-a]pyridine (Preparation 15) | 2-pyridin-2-yl-5,6-dihydro-4H-pyrrolo[1,2-b]pyrazole-3-boronic acid (Preparation 5) | ES MS (M + 1): 319.9 | Preparation 32 (General Suzuki Coupling Method C) |

-continued

| Example | Product | Starting Material A | Starting Material B | Physical Data | Comments |
|---|---|---|---|---|---|
| 42 | 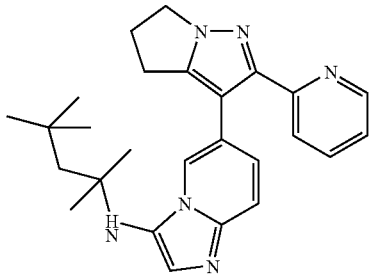<br>[6-[2-(pyridin-2-yl)-5,6-dihydro-4H-pyrrolo[1,2-b]pyrazol-3-yl]-imidazo[1,2-a]pyridin-3-yl]-(1,1,3,3-tetramethyl-butyl)-amine | (6-iodo-imidazo[1,2-a]pyridin-3-yl)-(1,1,3,3-tetramethyl-butyl)-amine (Preparation 16) | 2-(pyridin-2-yl)-5,6-dihydro-4H-pyrrolo[1,2-b]pyrazole-3-boronic acid (Preparation 5) | ES MS (M + 1): 429.0 | Example 15 (General Suzuki Coupling Method E) |
| 43 | 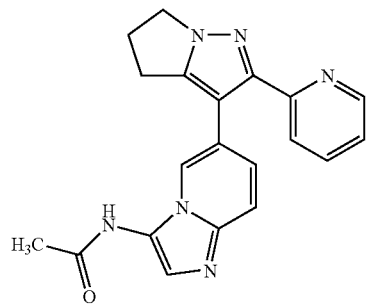<br>N-[6-[2-(pyridin-2-yl)-5,6-dihydro-4H-pyrrolo[1,2-b]pyrazol-3-yl]-imidazo[1,2-a]pyridin-3-yl]-acetamide | N-acetyl-N-(6-bromo-imidazo[1,2-a]pyridin-3-yl)-acetamide (Preparation 17) | 2-(pyridin-2-yl)-5,6-dihydro-4H-pyrrolo[1,2-b]pyrazole-3-boronic acid (Preparation 5) | ES MS (M + 1): 358.9 | Preparation 32 (General Suzuki Coupling Method C) |

EXAMPLE 44

Preparation of 6-(2-Pyridin-2-yl-5,6-dihydro-4H-pyrrolo[1,2-b]pyrazol-3-yl)-imidazo[1,2-a]pyridine-3-carboxylic acid amide

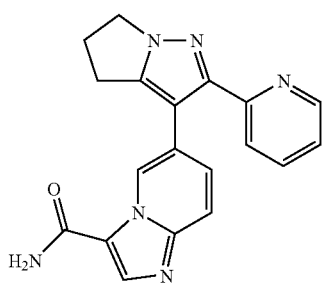

Add 7N ammonia in methanol (10 mL) to a sealed tube containing 6-[2-(pyridin-2-yl)-5,6-dihydro-4H-pyrrolo[1,2-b]pyrazol-3-yl]-imidazo[1,2-a]pyridine-3-carboxylic acid ethyl ester (Example 35; 0.105 g, 0.28 mmol). Heat at 110° C. for 48 h. Flash chromatograph using dichloromethane/methanol mixtures to give the title compound (0.08 g, 82%) as a white solid. MS ES+ m/e 344.9 (M+1). $^1$H NMR (400 MHz, DMSO-d$_6$) δ 9.57 (s, 1H), 8.4-8.37 (m, 1H), 8.28 (s, 1H), 7.82-7.77 (m, 3H), 7.59 (d, J=9 Hz, 1H), 7.4 (dd, J=9.0, 2.0 Hz, 1H), 7.25 (m, 1H), 4.21 (t, J=7 Hz, 2H), 2.99 (t, J=7, 2H), 2.62 (quintet, 2H, 8 Hz).

EXAMPLE 45

Preparation of 6-[2-(6-Methyl-pyridin-2-yl)-5,6-dihydro-4H-pyrrolo[1,2-b]pyrazol-3-yl]-imidazo[1,2-a]pyridine-2-carboxylic Acid (2-Dimethylamino-ethyl)-amide

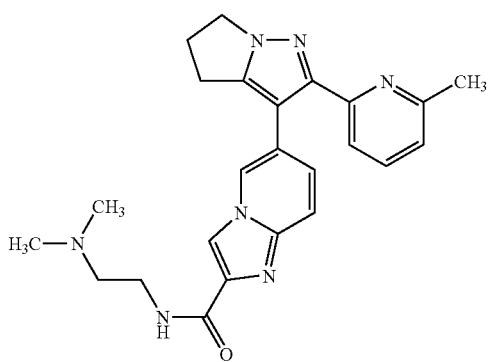

Add 2M trimethylaluminum in toluene (0.38 mL, 0.38 mmol) to a solution of N,N-dimethylethylenediamine (0.034 g, 0.38 mmol) in dichloromethane (20 mL). Stir for 20 min and transfer via cannula to a solution of 6-[2-(6-methyl-pyridin-2-yl)-5,6-dihydro-4H-pyrrolo[1,2-b]pyrazol-3-yl]-imidazo[1,2-a]pyridine-2-carboxylic acid ethyl ester (0.1 g, 0.26 mmol) in dichloromethane (20 mL). Heat at 45° C. and stir for 1.5 h. Add saturated aqueous sodium bicarbonate and extract into dichloromethane. Reversed phase chromatography gives the titled compound (0.067 g, 60%) as a white solid. MS ES+ m/e 430.0 (M+1).

EXAMPLE 46

Preparation of 6-[2-(6-Methyl-pyridin-2-yl)-5,6-dihydro-4H-pyrrolo[1,2-b]pyrazol-3-yl]-imidazo[1,2-a]pyridine-3-carboxylic Acid Amide

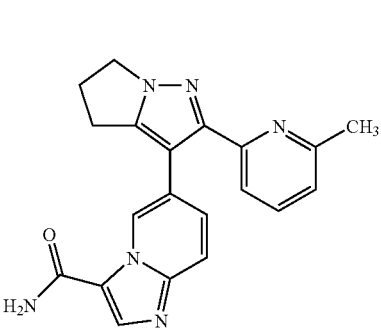

A. Preparation of 6-[2-(6-Methyl-pyridin-2-yl)-5,6-dihydro-4H-pyrrolo[1,2-b]pyrazol-3-yl]-imidazo[1,2-a]pyridine-3-carboxylic Acid Ethyl Ester Add tetrakis(triphenylphosphine)palladium(0) (0.53 g, 0.46 mmol) to a 2 L flask containing a solution of 6-iodo-imidazo[1,2-a]pyridine-3-carboxylic acid ethyl ester (Preparation 14; 7.28 g, 23.0 mmol), and sodium bicarbonate (3.87 g, 46.1 mmol) in acetonitrile (350 mL) and water (250 mL). Reflux the reaction mixture for 3 h. Cool, concentrate to about ⅔ the volume, extract into dichloromethane (4×250 mL), and concentrate. Flash chromatography using a gradient from 100% hexanes to 100% ethyl acetate (10 min, 45 ml/min), followed by isocratic 9:1 ethyl acetate/methanol gives the subtitled compound (6.06 g, 67%) as a white solid. TOF MS ES+ exact mass calculated for $C_{10}H_{91}N_2O_2$ (p+1): m/z=387.1773; Found: 388.1792.

B. Preparation of 6-[2-(6-Methyl-pyridin-2-yl)-5,6-dihydro-4H-pyrrolo[1,2-b]pyrazol-3-yl]-imidazo[1,2-a]pyridine-3-carboxylic Acid Amide Add formamide (36 mL) to a suspension of sodium hydride (2.04 g, 60% dispersion in mineral oil, 51.1 mmol) and 6-[2-(6-methyl-pyridin-2-yl)-5,6-dihydro-4H-pyrrolo[1,2-b]pyrazol-3-yl]-imidazo[1,2-a]pyridine-3-carboxylic acid ethyl ester (3.6 g, 9.29 mmol) in DMF (15 mL) over 10 min. Heat at 155° C. for 40 min, cool, dilute with ethyl acetate, and carefully dilute with saturated aqueous sodium bicarbonate. Filter any un-dissolved solid and wash with ethyl acetate. Concentrate the remaining organic layer and adsorb onto a 1:1 mixture of SiO$_2$ and Celite®. Flash chromatography using ethyl acetate methanol mixtures followed by trituration of the combined lots in diethyl ether gives the titled compound (3.32 g, 99%) as a white solid. TOF MS ES+ exact mass calculated for $C_{10}H_9IN_2O_2$ (p+1): m/z=359.1620 Found: 359.1617.

EXAMPLE 47

Preparation of 7-[2-(Pyridin-2-yl)-5,6-dihydro-4H-pyrrolo[1,2-b]pyrazol-3-yl]-imidazo[1,2-a]pyridine

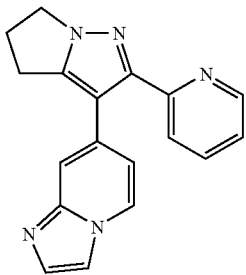

Combine 7-chloro-imidazo[1,2-a]pyridine (PCT Appl. WO 01/38326 A2; 134 mg, 0.88 mmol) with 2-(pyridin-2-yl)-5,6-dihydro-4H-pyrrolo[1,2-b]pyrazole-3-boronic acid (Preparation 5; 369 mg, 0.97 mmol) in the presence of tetrakis (triphenylphosphine)palladium(0) (30 mg, 0.03 mmol) and 2M aqueous sodium bicarbonate (1.0 mL) in benzene (2.1 mL) and ethanol (0.3 mL). Heat the mixture for 67 h at 100° C. Dilute the reaction with methylene chloride (10 mL) and water (10 mL). Separate the layers and extract the aqueous layer with methylene chloride (2×10 mL). Combine the organic layers and dry over sodium sulfate. Filter the solution and evaporate the solvent. Purify the crude product by flash chromatography using the appropriate ammonia in methanol/methylene chloride mixture to give the title compound as a tan solid (41 mg, 15%). MS m/e (302.0, M+1). $^1$H NMR (CDCl$_3$) δ 8.57 (m, 1H), 7.96 (dd, J=1, 7 Hz, 1H), 7.6 (m, 5H), 7.19 (m, 1H), 6.69 (dd, J=1, 7 Hz, 1H), 4.27 (t, J=8 Hz, 2H), 3.08(t, J=7 Hz, 2H), 2.71 (q, J=7 Hz, 2H).

EXAMPLES 48-56

General Suzuki Coupling Method F

Combine the heteroarylboronic acid (1.0 eq) with the heteroaryl halide (1.2 eq) in the presence of [1,1'-bis(diphenylphosphino)ferrocene)dichloropalladium(II) complex with dichloromethane (1:1) (3-5 mol %), a suitable ligand, preferably biphenyl-2-yl-di-tert-butylphosphane (6-10 mol %), and a suitable base, preferably sodium carbonate (2-3 eq) 4:1 dioxane/ethanol or 1:1 DMSO/water in a 10 mL glass tube. Seal the reaction vessel with a septum and place in a microwave reactor. Using microwave radiation raise the temperature to between 80 and 130° C. over 10 to 30 min. Dilute the reaction mixture with 1:1 chloroform/isopropyl alcohol and wash the resulting solution with saturated sodium chloride solution. Dry the organic phase over sodium sulfate, filter, and evaporate. Purify the residue via flash chromatography using gradients of dichloromethane to 9% methanol/91% dichloromethane or dichloromethane to 20% tetrahydrofuran/80% dichloromethane to 9% methanol/91% dichloromethane to provide the desired products.

The following compounds were prepared utilizing the General Suzuki Coupling Methods.

| Example | Product | Starting Material A | Starting Material B | Physical Data | Comments |
|---|---|---|---|---|---|
| 48 | 3-(4-chloro-phenyl)-6-[2-(6-methyl-pyridin-2-yl)-5,6-dihydro-4H-pyrrolo[1,2-b]pyrazol-3-yl]-imidazo[1,2-a]pyridine | Preparation 18 | 3-(4-chloro-phenyl)-6-iodo-imidazo[1,2-a]pyridine (available from Bionet) | MS (ES) m/e 426.2 (M + 1) | General Suzuki Coupling Method F |

-continued

| Example | Product | Starting Material A | Starting Material B | Physical Data | Comments |
|---|---|---|---|---|---|
| 49 | 5-[2-(6-methyl-pyridin-2-yl)-5,6-dihydro-4H-pyrrolo[1,2-b]pyrazol-3-yl]-1H-benzoimidazole | Preparation 18 | 5- and 6-iodo-benzoimidazole-1-carboxylic acid tert-butyl ester (Preparations 24/25) | MS (ES) m/e 316.2 (M + 1) | Example 48 (General Suzuki Coupling Method F) |
| 50 | 1-methyl-6-[2-(6-methyl-pyridin-2-yl)-5,6-dihydro-4H-pyrrolo[1,2-b]pyrazol-3-yl]-1H-benzoimidazole | Preparation 18 | 6-iodo-1-methyl-1H-benzoimidazole (Preparation 22) | MS (ES) m/e 330.2 (M + 1) | Example 48 (General Suzuki Coupling Method F) |
| 51 | 1-methyl-6-[2-(pyridin-2-yl)-5,6-dihydro-4H-pyrrolo[1,2-b]pyrazol-3-yl]-1H-benzoimidazole | Preparation 20 | 6-iodo-1-methyl-1H-benzoimidazole (Preparation 22) | MS (ES) m/e 316.2 (M + 1) | Example 48 (General Suzuki Coupling Method F) |

-continued

| Example | Product | Starting Material A | Starting Material B | Physical Data | Comments |
|---|---|---|---|---|---|
| 52 | 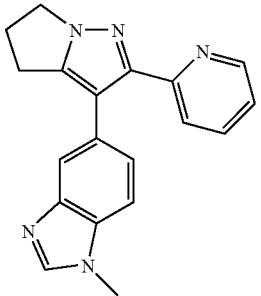<br>1-methyl-5-[2-(pyridin-2-yl)-5,6-dihydro-4H-pyrrolo[1,2-b]pyrazol-3-yl]-1H-benzoimidazole | Preparation 20 | 5-iodo-1-methyl-1H-benzoimidazole (Preparation 22) | MS (ES) m/e 316.2 (M + 1) | Example 48 (General Suzuki Coupling Method F) |
| 53 | 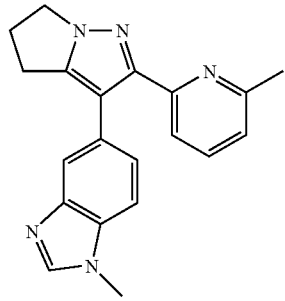<br>1-methyl-5-[2-(6-methyl-pyridin-2-yl)-5,6-dihydro-4H-pyrrolo[1,2-b]pyrazol-3-yl]-1H-benzoimidazole | Preparation 18 | 5-iodo-1-methyl-1H-benzoimidazole (Preparation 22) | MS (ES) m/e 330.2 (M + 1) | Example 48 (General Suzuki Coupling Method F) |

-continued

| Example | Product | Starting Material A | Starting Material B | Physical Data | Comments |
|---|---|---|---|---|---|
| 54 | 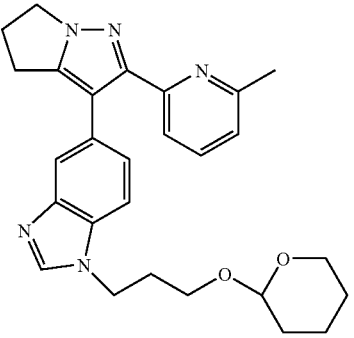 and 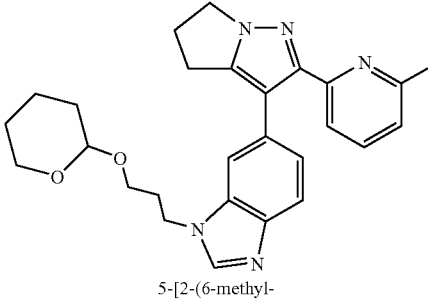<br>5-[2-(6-methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole and 6-[2-(6-methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole | Preparation 18 | 5-iodo-1-[3-(tetrahydro-pyran-2-yloxy)-propyl]-1H-benzoimidazole and 6-iodo-1-[3-(tetrahydro-pyran-2-yloxy)-propyl]-1H-benzoimidazole (Preparation 23) | MS (ES) m/e 458.3 (M + 1) for each isomer | Example 48 (General Suzuki Coupling Method F) |

-continued

| Example | Product | Starting Material A | Starting Material B | Physical Data | Comments |
|---|---|---|---|---|---|
| 55 | 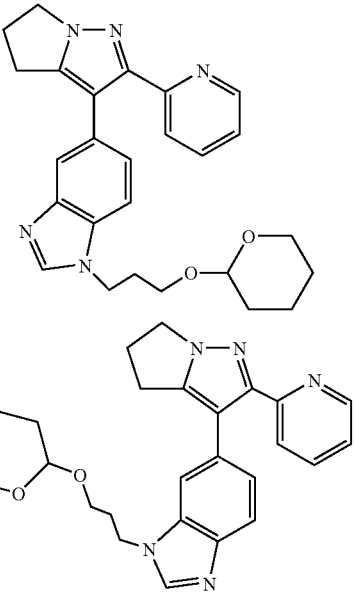<br>5-[2-(pyridin-2-yl)-5,6-dihydro-4H-pyrrolo[1,2-b]pyrazol-3-yl]-1-[3-(tetrahydro-pyran-2-yloxy)-propyl]-1H-benzoimidazole and 6-[2-(pyridin-2-yl)-5,6-dihydro-4H-pyrrolo[1,2-b]pyrazol-3-yl]-1-[3-(tetrahydro-pyran-2-yloxy)-propyl]-1H-benzoimidazole | Preparation 20 | 5-iodo-1-[3-(tetrahydro-pyran-2-yloxy)-propyl]-1H-benzoimidazole and 6-iodo-1-[3-(tetrahydro-pyran-2-yloxy)-propyl]-1H-benzoimidazole (Preparation 23) | MS (ES) m/e 444.3 (M + 1) for each isomer | Preparation 33 (General Suzuki Coupling Method D used replacing acetonitrile with DMSO) |
| 55a | 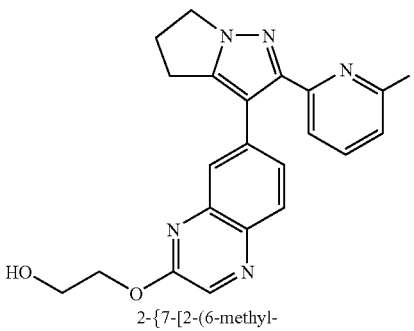<br>2-{7-[2-(6-methyl-pyridin-2-yl)-5,6-dihydro-4H-pyrrolo[1,2-b]pyrazol-3-yl]-pyrido[2,3-b]pyrazin-2-yloxy}-ethanol | Preparation 18 | 2-(7-bromoquinoxalin-2-yloxy)ethanol (Preparation 27) | MS (ES) m/e 388.2 (M + 1) | Example 48 (General Suzuki Coupling Method F) |

-continued

| Example | Product | Starting Material A | Starting Material B | Physical Data | Comments |
|---|---|---|---|---|---|
| 55b | 7-[2-(6-methyl-pyridin-2-yl)-5,6-dihydro-4H-pyrrolo[1,2-b]pyrazol-3-yl]-1H-quinoxalin-2-one | Preparation 18 | 2-(7-bromoquinoxalin-2-yloxy)ethanol (Preparation 27) | MS (ES) m/e 344.1 (M + 1) | Example 48 (General Suzuki Coupling Method F) |
| 55c | 3-[2-(6-methyl-pyridin-2-yl)-5,6-dihydro-4H-pyrrolo[1,2-b]pyrazol-3-yl][1,5]naphthyridine | Preparation 18 | 2,3-dibromo-[1,5]naphthyridine (available from Bionet) | MS (ES) m/e 344.1 (M + 1) | Example 48 (General Suzuki Coupling Method F) |

EXAMPLE 56

Preparation of 3-[6-[2-(6-Methyl-pyridin-2-yl)-5,6-dihydro-4H-pyrrolo[1,2-b]pyrazol-3-yl]-benzoimidazol-1-yl]-propan-1-ol

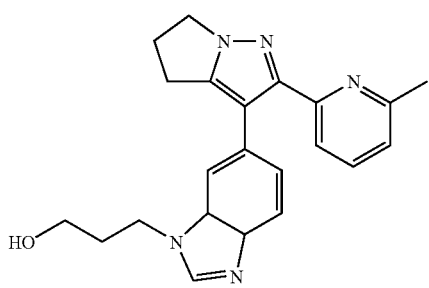

Heat a solution of (6-[2-(6-methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole (Example 54; 368 mg mg, 0.8 mmol) in 4:2:1 acetic acid/tetrahydrofuran/water (20 mL) to 80° C. for 18 h. Remove the solvent in vacuo and dissolve the residue in excess 3:1 chloroform/isopropyl alcohol. Wash the organic layer with saturated sodium bicarbonate, dry over sodium sulfate, filter, and concentrate in vacuo. Purify the residue by column chromatography on silica gel eluting with dichloromethane to 10% methanol/90% dichloromethane to give the desired product as a white solid (225 mg, 75%). MS ES+ m/e 374.3 (M+1).

| Example | Product | Starting Material A | Starting Material B | Physical Data | Comments |
|---|---|---|---|---|---|
| 57 | 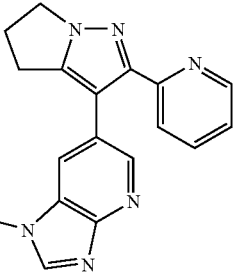<br>3-[6-[2-(pyridin-2-yl)-5,6-dihydro-4H-pyrrolo[1,2-b]pyrazol-3-yl]-benzoimidazol-1-yl]-propan-1-ol | Example 55 | Acetic acid/THF/water | MS (ES) m/e 360.1 (M + 1) | |

EXAMPLE 57a

Preparation of Methanesulfonic Acid 3-[6-[2-(6-Methyl-pyridin-2-yl)-5,6-dihydro-4H-pyrrolo[1,2-b]pyrazol-3-yl]-benzoimidazol-1-yl]-propyl Ester Stir a solution of 3-[6-[2-(6-methyl-pyridin-2-yl)-5,6-dihydro-4H-pyrrolo[1,2-b]pyrazol-3-yl]-benzoimidazol-1-yl]-propan-1-ol (Example 56; 257 mg, 0.67 mmol) and methanesulfonyl chloride (200 µl, 2.06 mmol) in dry pyridine (5 mL) for 2 h. Remove the pyridine in vacuo and dissolve the residue in excess chloroform. Wash the organic layer with saturated sodium bicarbonate and dry over sodium sulfate. Filter and concentrate in vacuo to give the product as a white foam (175 mg, 55%). MS ES+ m/e 452.2 (M+1).

| Example | Product | Starting Material A | Starting Material B | Physical Data | Comments |
|---|---|---|---|---|---|
| 57b | 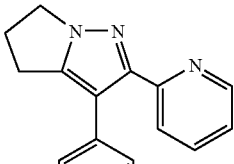<br>methanesulfonic acid 3-[6-[2-(pyridin-2-yl)-5,6-dihydro-4H-pyrrolo[1,2-b]pyrazol-3-yl]-benzoimidazol-1-yl]-propyl ester | Example 37 | methanesulfonyl chloride/pyridine | MS (ES) m/e 438.2 (M + 1) | |

EXAMPLE 58

Preparation of Dimethyl-[3-[6-[2-(6-methyl-pyridin-2-yl)-5,6-dihydro-4H-pyrrolo[1,2-b]pyrazol-3-yl]-1H-benzoimidazol-1-yl]propyl] amine

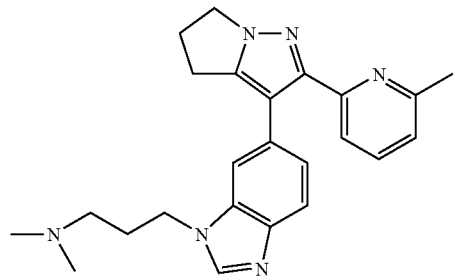

Combine methanesulfonic acid methanesulfonic acid 3-[6-[2-(6-methyl-pyridin-2-yl)-5,6-dihydro-4H-pyrrolo[1,2-b]pyrazol-3-yl]-benzoimidazol-1-yl]-propyl ester (Example 57a; 22 mg, 0.048 mmol) with 2M dimethylamine in THF (2 mL). Heat the mixture at 80° C. for 30 min. Cool, evaporate the excess amine, and purify the crude product with FCC to give the title compound (18.5 mg, 95%). MS m/e 401.3 (M+1).

| Example | Product | Starting Material A | Starting Material B | Physical Data | Comments |
|---|---|---|---|---|---|
| 59 | 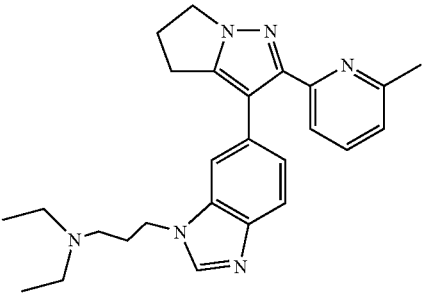<br>diethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine | Example 57a | diethylamine (available from Aldrich) | MS (ES) m/e 429.3 (M + 1) | |
| 60 | 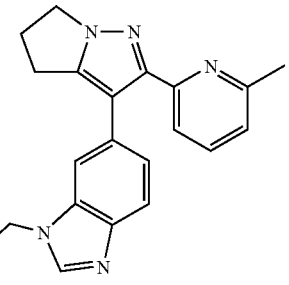<br>6-[2-(6-methyl-pyridin-2-yl)-5,6-dihydro-4H-pyrrolo[1,2-b]pyrazol-3-yl]-1-(3-morpholin-4-yl-propyl)-1H-benzoimidazole | Example 57a | morpholine (available from Aldrich) | MS (ES) m/e 443.3 (M + 1) | |
| 61 | 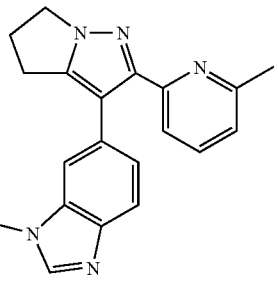<br>6-[2-(6-methyl-pyridin-2-yl)-5,6-dihydro-4H-pyrrolo[1,2-b]pyrazol-3-yl]-1-(3-pyrrolidin-1-yl-propyl)-1H-benzoimidazole | Example 57a | pyrrolidine (available from Aldrich) | MS (ES) m/e 427.3 (M + 1) | |

-continued

| Example | Product | Starting Material A | Starting Material B | Physical Data | Comments |
|---|---|---|---|---|---|
| 62 | 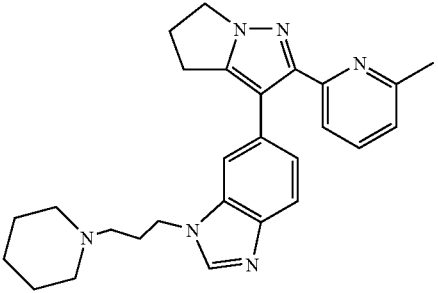<br>6-[2-(6-methyl-pyridin-2-yl)-5,6-dihydro-4H-pyrrolo[1,2-b]pyrazol-3-yl]-1-(3-piperidin-1-yl-propyl)-1H-benzoimidazole | Example 57a | piperidine (available from Aldrich) | MS (ES) m/e 441.4 (M + 1) | |

The following compounds were prepared using one of the General Suzuki Coupling Methods.

| Example | Product | Starting Material A | Starting Material B | Physical Data | Comments |
|---|---|---|---|---|---|
| 63 | 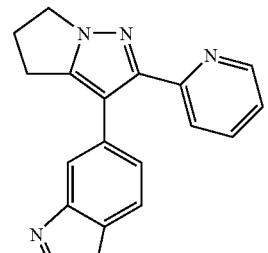<br>5-[2-(pyridin-2-yl)-5,6-dihydro-4H-pyrrolo[1,2-b]pyrazol-3-yl]-1H-benzoimidazole | 5- and 6-iodo-benzoimidazole-1-carboxylic acid tert-butyl ester (Preparations 24/25) | Preparation 5 | Mp 121-123° C. MS (ESI) m/e 302 (M + 1). $^1$H NMR (DMSO-$d_6$) δ 12.34 (br s, 0.5 H), 12.26 (br s, 0.5 H), 8.42 (br s, 1H), 8.13 d, J = 5 Hz, 1H), 7.77 (t, J = 8 Hz, 1H), 7.60 (d, J = 8 Hz, 1H), 7.52 (d, J = 9 Hz, 1H), 7.38 (s, 1H), 2.26 (dd, J = 7, 5 Hz, 1H), 7.07 (t, J = 6 Hz, 1H), 4.19 (t, J = 7 Hz, 2H), 3.00 (dd, J = 8, 7 Hz, 2H), 2.66-2.56 (m, 2H). HPLC: >99%, $R_t$ = 10.3 min. TLC (SiO$_2$): $R_f$ 0.4 (1:1 methylene chloride/[80:18:2 chloroform/methanol/concentrated aqueous ammonium hydroxide]) | Preparation 33 (General Suzuki Coupling Method D) |

-continued

| Example | Product | Starting Material A | Starting Material B | Physical Data | Comments |
|---|---|---|---|---|---|
| 64 | 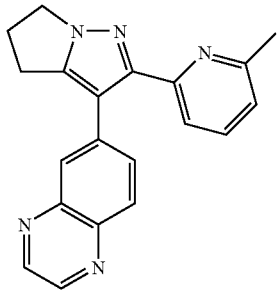<br>6-[2-(6-methyl-pyridin-2-yl)-5,6-dihydro-4H-pyrrolo[1,2-b]pyrazol-3-yl]-quinoxaline | 6-bromo-quinoxoline (Landquist, J. Chem. Soc., 1953, 2816-2819) | Preparation 2 | Mp 137-139° C. MS (ESI) m/e 328 (M + 1). $^1$H NMR (300 MHz, CDCl$_3$) δ 8.78 (dd, J = 6, 2 Hz, 2H), 8.03 (d, J = 2 Hz, 1H), 7.96 (d, J = 9 Hz, 1H), 7.70 (dd, J = 9, 2 Hz, 1H), 7.51 (t, J = 8 Hz, 1H), 7.32 (d, J = 8 Hz, 1H), 7.08 (d, J = 8 Hz, 1H), 4.31 (t, J = 7 Hz, 2H), 3.13 (dd, J = 8, 7 Hz, 2H), 2.77-2.67 (m, 2H), 2.52 (s, 3H). HPLC: >99%, R$_t$ = 13.7 min. TLC (SiO$_2$): R$_f$ 0.5 (1:1 methylene chloride/[80:18:2 chloroform/methanol/concentrated aqueous ammonium hydroxide]) | Preparation 30 (General Suzuki Coupling Method A) |
| 65 | 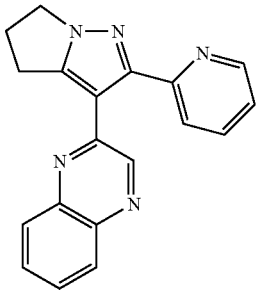<br>2-[2-(pyridin-2-yl)-5,6-dihydro-4H-pyrrolo[1,2-b]pyrazol-3-yl]-quinoxaline | 2-bromo-quinoxoline (Kato, Y. et al. Tetrahedron Lett. 2001, 42, 4849-4851) | Preparation 5 | Mp 162-164° C. MS (ESI) m/e 314 (M + 1). $^1$H NMR (CDCl$_3$) δ 8.96 (s, 1H), 8.53 (d, J = 5 Hz, 1H), 8.01 (t, J = 7 Hz, 2H), 7.86 (d, J = 8 Hz, 1H), 7.76-7.69 (m, 3H), 7.25 (m, 1H), 4.30 (t, J = 7 Hz, 2H), 3.29 (dd, J = 8, 7 Hz, 2H), 2.27 (t, J = 8, 7 Hz, 2H). HPLC: 97.7%, R$_t$ = 15.4 min. TLC (SiO$_2$): R$_f$ 0.4 (2:1 methylene chloride/[80:18:2 chloroform/methanol/concentrated aqueous ammonium hydroxide]) | Preparation 30 (General Suzuki Coupling Method A) |
| 66 | 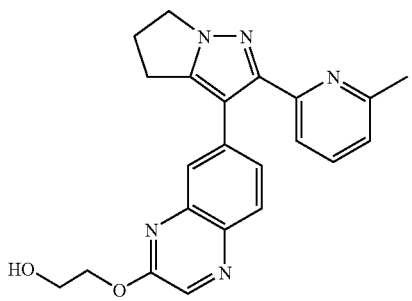<br>2-[7-[2-(6-methyl-pyridin-2-yl)-5,6-dihydro-4H-pyrrolo[1,2-b]pyrazol-3-yl]-quinoxalin-2-yloxy]-ethanol | Preparation 27 | Preparation 2 | MS ES$^+$ m/e 388.2 (M + 1) | Example 48 (General Suzuki Coupling Method F) |

| Example | Product | Starting Material A | Starting Material B | Physical Data | Comments |
|---|---|---|---|---|---|
| 66a | 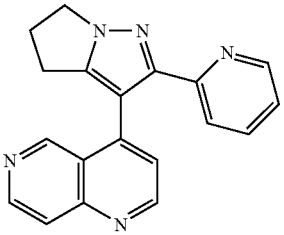<br>4-[2-(pyridin-2-yl)-5,6-dihydro-4H-pyrrolo[1,2-b]pyrazol-3-yl]-[1,6]naphthyridine | Preparation 20 | 4-bromo-1,6-naphthiridine (Paudler, W. W.; Kress, T. J. J. Het. Chem. 1965, 2, 393-397) | MS (APCI) m/e = 314 (M + 1)<br>$^1$H NMR (CDCl$_3$) δ 9.17 (d, J = 1Hz, 1H), 9.02 (d, J = 5 Hz, 1H), 8.68 (d, J = 6 Hz, 1H), 8.21 (ddd, J = 5, 2, 1 Hz, 1H), 7.92 (dd, J = 6, 1 Hz, 1H), 7.64-7.54 (m, 2H), 7.39 (d, J = 5 Hz, 1H), 7.07 (ddd, J = 6, 4, 1 Hz, 1H), 4.37 (t, J = 7 Hz, 2H), 2.91 (dd, J = 8, 6 Hz, 2H), 2.78-2.68 (m, 2H).<br>HPLC: 96.2%, R$_t$ = 12.3 min. | Preparation 33 (General Suzuki Coupling Method D) |

EXAMPLE 67

Preparation of 6-[2-(6-Methyl-pyridin-2-yl)-5,6-dihydro-4H-pyrrolo[1,2-b]pyrazol-3-yl]-isoquinoline

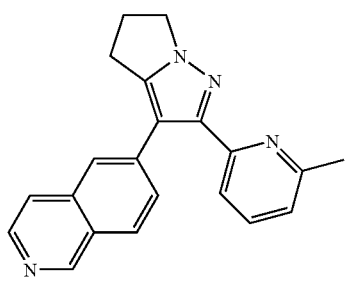

A. Preparation of 6-Iodoisoquinoline

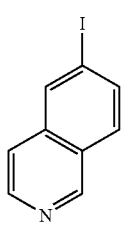

Heat a mixture of 6-bromoisoquinoline (Aldrich; 0.320 g, 1.54 mmol), copper (I) iodide (0.155 g, 0.815 mmol), and potassium iodide (1.27 g, 7.96 mmol) in N,N-dimethylformamide (5.0 mL) to 130° C. at 3 h under microwave irradiation. Pour the cooled reaction mixture into 4:1 dichloromethane/diethyl ether (100 mL) and filter. Wash the filtrate with 5% aqueous sodium bisulfite solution (2×50 mL). Dry the organic layer over sodium chloride, decant the organic layer, and remove the solvents under reduced pressure. Dry the residue under vacuum for 18 h to give 0.4 g (100%) of the title compound as a dark red-brown solid. This material is carried on directly to the next step without further purification. MS (electrospray, m/z) 256.1 (M+1).

B. Preparation of 6-[2-(6-Methyl-pyridin-2-yl)-5,6-dihydro-4H-pyrrolo[1,2-b]pyrazol-3-yl]-isoquinoline Dissolve 6-iodoisoquinoline (0.085 g, 0.333 mmol) and 2-(6-methyl-pyridin-2-yl)-5,6-dihydro-4H-pyrrolo[1,2-b]pyrazole-3-boronic acid (Preparation 2; 0.077 g, 0.317 mmol) in dioxane (2.5 mL). Add 5M aqueous potassium carbonate (0.667 mL, 3.33 mmol) followed by triphenylphosphine (5.2 g, 0.020 mmol) and tris(dibenzylidineacetone) dipalladium (18 mg, 0.020 mmol). Reflux the mixture for 2 h and cool to room temperature. Load the reaction mixture on to a cartridge containing SCX resin (5 g) and wash the resin sequentially with 1 volume dichloromethane, 1 volume methanol, and 1 volume methanol containing 2N ammonia. Remove the organic solvents under reduced pressure. Chromatograph on 15 g silica gel eluting with 5% methanol in ethyl acetate to provide 0.053 g (48%) of the title compound as a tan solid.

MS (electrospray, m/z) 327.4 (M+1).

EXAMPLES 68-70

The following compounds were prepared using one of the General Suzuki Coupling Methods.

| Example | Product | Starting Material A | Starting Material B | Physical Data | Comments |
|---|---|---|---|---|---|
| 68 | 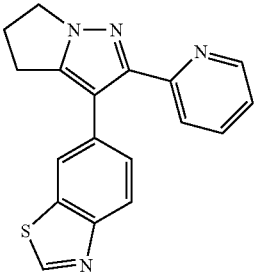<br>6-[2-(pyridin-2-yl)-5,6-dihydro-4H-pyrrolo[1,2-b]pyrazol-3-yl]-benzothiazole | Preparation 28 | Preparation 5 | MS (ESI) m/e 319 (M + 1). $^1$H NMR (CDCl$_3$) δ 8.95 (s, 1H), 8.62 (m, 1H), 8.10 (m, 1H), 7.94 (s, 1H), 7.62 (m, 1H), 7.56-7.45 (m, 2H), 7.20 (m, 1H), 4.32 (t, J = 8 Hz, 2H), 3.10 (t, J = 8 Hz, 2H), 2.82-2.70 (m, 2H). HPLC: 95.4%, R$_t$ = 10.32 min. TLC (SiO$_2$): R$_f$ 0.25 (1:1 [80:18:2 chloroform/methanol/concentratd aqueous ammonium hydroxide]/dichloro methane) | Preparation 33 (General Suzuki Coupling Method D) |
| 69 | 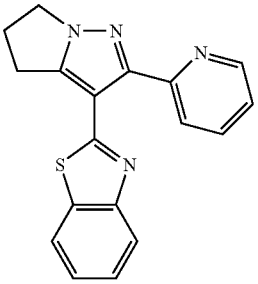<br>2-[2-(pyridin-2-yl)-5,6-dihydro-4H-pyrrolo[1,2-b]pyrazol-3-yl]-benzothiazole | 2-bromo-benzothiazole (available from Maybridge) | Preparation 5 | MS (ESI) m/e 319 (M + 1). $^1$H NMR (CD$_3$OD) δ 9.11 (d, J = 6 Hz, 1H), 8.82 (d, J = 8 Hz, 1H), 8.59 (td, J = 8, 1 Hz, 1H), 8.28 (d, J = 8 Hz, 1H), 8.09-8.01 (m, 2H), 7.67 (t, J = 8 Hz, 1H), 7.54 (t, J = 8 Hz, 1H), 4.42 (dd, J = 8, 7 Hz, 2H), 3.38-3.33 (m, 2H), 2.93-2.83 (m, 2H). HPLC: 99.5%, R$_t$ = 17.38 min. TLC (SiO$_2$): R$_f$ 0.25 (10% methanol/dichlorom ethane) | Preparation 32 (General Suzuki Coupling Method C) |
| 70 | 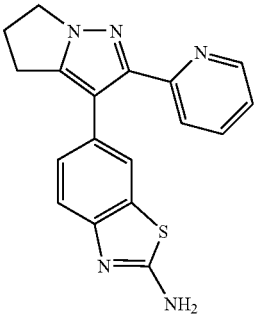<br>5-[2-(pyridin-2-yl)-5,6-dihydro-4H-pyrrolo[1,2-b]pyrazol-3-yl]-benzothiazol-2-ylamine | 5-bromo-benzothiazol-2-ylamine (available from Oakwood) | Preparation 5 | MS (ESI) m/e 334 (M + 1). $^1$H NMR (CDCl$_3$) δ 8.50 (ddd, J = 4, 2, 1 Hz, 1H), 7.80 (dd, J = 8, 2 Hz, 1H), 7.75 (d, J = 2 Hz, 1H), 7.62 (s, 1H), 7.36-7.32 (m, 1H), 7.28 (d, J = 8 Hz, 1H), 7.05 (dd, J = 8, 2 Hz, 1H), 4.24 (t, J = 7 Hz, 2H), 3.06 (t, J = 7 Hz, 2H), 2.76-2.66 (m, 2H). HPLC: 97.1%, R$_t$ = 11.5 min. TLC (SiO$_2$): R$_f$ 0.1 (10% methanol/dichlorom ethane) | Preparation 32 (General Suzuki Coupling Method C) |

EXAMPLE 71

Preparation of 4-[2-(Pyridin-2-yl)-5,6-dihydro-4H-pyrrolo[1,2-b]pyrazol-3-yl]-1H-indole

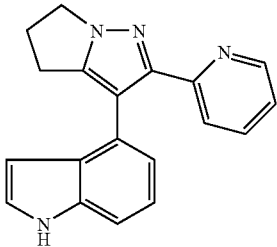

A. Preparation of 4-Bromo-indole-1-carboxylic Acid tert-Butyl Ester

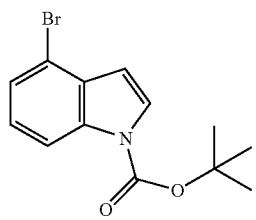

Add di-tert-butyl dicarbonate (1.4 g. 6.4 mmol) and sodium hydride (0.15 g, 60% dispersion in mineral oil, 3.8 mmol) to a solution of 4-bromoindole (0.4 mL, 3.2 mmol) in THF (11 mL) at 0° C. Stir the reaction for 22 h, quench with saturated aqueous ammonium chloride, and extract with methylene chloride. Dry the combined organic extracts with sodium sulfate, filter, and concentrate in vacuo. Purify by flash column chromatography, utilizing the appropriate mixture of hexanes and methylene chloride, to provide 0.85 g (90%) of the titled compound as a clear, colorless oil. $^1$H NMR (CDCl$_3$) δ 8.10 (d, J=8 Hz, 1H), 7.63 (d, J=4 Hz, 1H), 7.38 (d, J=8 Hz, 1H), 7.16 (t, J=8 Hz, 1H), 6.64 (d, J=4 Hz, 1H), 1.67 (s, 9H). TLC (SiO$_2$): R$_f$ 0.3 (9:1 hexanes/methylene chloride).

B. Preparation of 4-[2-(Pyridin-2-yl)-5,6-dihydro-4H-pyrrolo[1,2-b]pyrazol-3-yl]-indole-1-carboxylic Acid tert-Butyl Ester

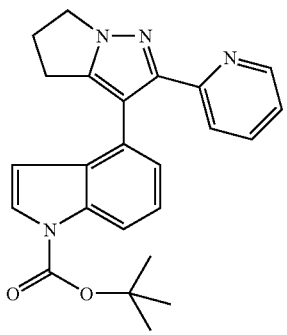

The titled intermediate was made via Preparation 33 (General Suzuki Coupling Method D) from 4-bromo-indole-1-carboxylic acid tert-butyl ester and 2-(pyridin-2-yl)-5,6-dihydro-4H-pyrrolo[1,2-b]pyrazole-3-boronic acid (Preparation 5). MS (ESI) m/e 401 (M+1). TLC (SiO$_2$): R$_f$ 0.5 (1:1 methylene chloride/[80:18:2 chloroform/methanol/concentrated aqueous ammonium hydroxide]).

C. Preparation of 4-[2-(Pyridin-2-yl)-5,6-dihydro-4H-pyrrolo[1,2-b]pyrazol-3-yl]-1H-indole Add trifluoroacetic acid (0.4 mL) to a solution of 4-[2-(pyridin-2-yl)-5,6-dihydro-4H-pyrrolo[1,2-b]pyrazol-3-yl]-indole-1-carboxylic acid tert-butyl ester (34 mg, 0.085 mmol) in methylene chloride (2 mL) at 0° C. Allow the reaction to warm to room temperature slowly over 19 h. Dilute the reaction with methylene chloride and methanol. Add concentrated aqueous ammonium hydroxide (2 mL) and concentrate in vacuo. Purify by flash column chromatography, using the appropriate mixture of methylene chloride, chloroform, methanol, and concentrated aqueous ammonium hydroxide, to provide 11 mg (8% yield over 2 steps) of the title compound as a white solid. MS (APCI) m/e 301 (M+1). $^1$H NMR (DMSO-d$_6$) δ 10.98 (s, 1H), 8.30 (d, J=4 Hz, 1H), 7.65 (td, J=8, 2 Hz, 1H), 7.46 (d, J=8 Hz, H), 7.26 (d, J=8 Hz, 1H), 7.17-7.13 (m, 2H), 7.00 (t, J=8 Hz, 1H), 6.81 (d, J=7 Hz, 1H), 4.21 (t, J=7 Hz, 2H), 2.85 (dd, J=8, 7 Hz, 2H), 2.64-2.55 (m, 2H). HPLC: >99%, R$_t$=15.1 min. TLC (SiO$_2$): R$_f$ 0.2 (1:1 methylene chloride/[80:18:2 chloroform/methanol/concentrated aqueous ammonium hydroxide]).

EXAMPLE 72

Preparation of 3-[2-(Pyridin-2-yl)-5,6-dihydro-4H-pyrrolo [1,2-b]pyrazol-3-yl]-1H-indole

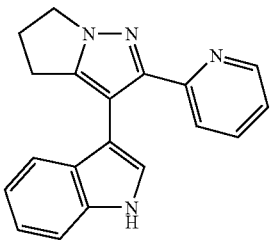

A. Preparation of 1-Benzenesulfonyl-3-(2-pyridin-2-yl-5,6-dihydro-4H-pyrrolo[1,2-b]pyrazol-3-yl)-1H-indole

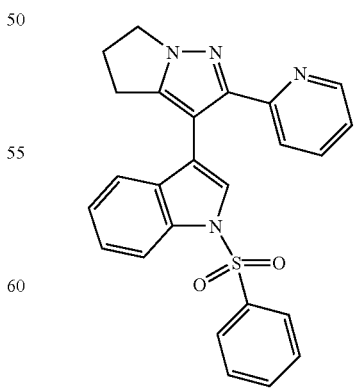

The titled intermediate was made via Preparation 33 (General Suzuki Coupling Method D) from 1-benzene-sulfonyl- 3-bromo-1H-indole (Maybridge) and 2-(pyridin-2-yl)-5,6-dihydro-4H-pyrrolo[1,2-b]pyrazole-3-boronic acid (Preparation 5). MS (ESI) m/e 441 (M+1). TLC (SiO$_2$): R$_f$ 0.5 (1:1 methylene chloride/[80:18:2 chloroform/methanol/concentrated aqueous ammonium hydroxide]).

B. Preparation of 3-[2-(Pyridin-2-yl)-5,6-dihydro-4H-pyrrolo [1,2-b]pyrazol-3-yl]-1H-indole Add potassium carbonate (75 mg, 0.55 mmol) to a solution of 1-benzenesulfonyl-3-[2-(pyridin-2-yl)-5,6-dihydro-4H-pyrrolo[1,2-b]pyrazol-3-yl]-1H-indole (120 mg, 0.27 mmol) in 3:1 methanol/water (1.2 mL). Reflux the reaction mixture for 16 h, cool to room temperature, and add toluene (50 mL). Concentrate in vacuo and purify by flash column chromatography, using the appropriate mixture of methylene chloride, chloroform, methanol, and concentrated aqueous ammonium hydroxide, to provide 6 mg (3% over 2 steps) of the title compound as a yellow solid.

MS (APCI) m/e 301 (M+1). $^1$H NMR (DMSO-d$_6$) δ 11.05 (s, 1H), 8.38 (br s, 1H), 7.70 (t, J=7 Hz, 1H), 7.57 (d, J=8 Hz, 1H), 7.36 (s, 1H), 7.35 (d, J=8 Hz, 1H), 7.21 (br s, 1H), 7.04-7.00 (m, 2H), 6.82 (dd, J=8, 7 Hz, 1H), 4.21 (t, J=7 Hz, 2H), 2.89 (t, J=7 Hz, 2H), 2.73-2.58 (m, 2H). HPLC: >99%, R$_t$=15.7 min. TLC (SiO$_2$): R$_f$ 0.4 (1:1 methylene chloride/[80:18:2 chloroform/methanol/concentrated aqueous ammonium hydroxide]).

EXAMPLES 73-77

The following compounds were prepared using one of the General Suzuki Coupling Methods.

| Example | Product | Starting Material A | Starting Material B | Physical Data | Comments |
|---|---|---|---|---|---|
| 73 | 3-(2,3-dihydro-benzofuran-5-yl)-2-(pyridin-2-yl)-5,6-dihydro-4H-pyrrolo[1,2-b]pyrazole | 5-iodo-2,3-dihydro-benzofuran (available from Frontier Scientific) | Preparation 5 | MS (ES) m/e 304 (M + 1) | Example 48 (General Suzuki Coupling Method F) |
| 74 | acetic acid 5-[2-(6-methyl-pyridin-2-yl)-5,6-dihydro-4H-pyrrolo[1,2-b]pyrazol-3-yl]-benzofuran-3-yl ester | acetic acid 5-iodo-benzofuran-3-yl ester, (Preparation 21a) | Preparation 2 | MS (ES) m/e 374 (M + 1) | Example 48 (General Suzuki Coupling Method F) |

| Example | Product | Starting Material A | Starting Material B | Physical Data | Comments |
|---|---|---|---|---|---|
| 75 | 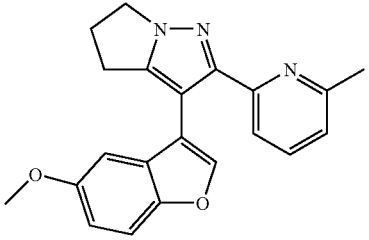<br>3-(5-methoxy-benzofuran-3-yl)-2-(6-methyl-pyridin-2-yl)-5,6-dihydro-4H-pyrrolo[1,2-b]pyrazole | 3-bromo-5-methoxy-benzofuran (Inoue, M. et al. J. Am. Chem. Soc. 2001, 123, 1878-1889) | Preparation 2 | MS (ES) m/e 346 (m + 1) | Example 48 (General Suzuki Coupling Method F) |
| 76 | 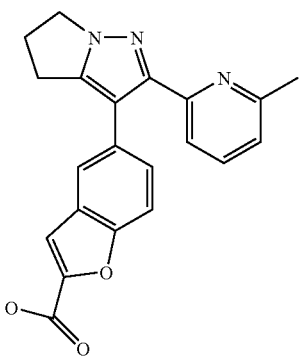<br>5-[2-(6-methyl-pyridin-2-yl)-5,6-dihydro-4H-pyrrolo[1,2-b]pyrazol-3-yl]-benzofuran-2-carboxylic acid | 5-bromo-benzofuran-2-carboxylic acid (available from Aldrich) | Preparation 2 | MS (ES) m/e 360 (M + 1) | Example 48 (General Suzuki Coupling Method F) |
| 77 | 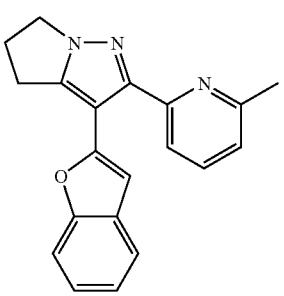<br>3-(benzofuran-2-yl)-2-(6-methyl-pyridin-2-yl)-5,6-dihydro-4H-5,6-dihydro-4H-pyrrolo[1,2-b]pyrazole | 3-bromo-2-(6-methyl-pyridin-2-yl)-5,6-dihydro-4H-pyrrolo[1,2-b]pyrazole (Preparation 1, Part D) | benzofuran-2-boronic acid (available from Lancaster) | MS (ES) m/e 316 (M + 1) | Example 48 (General Suzuki Coupling Method F) |

EXAMPLES 78-80

General Suzuki Coupling Method G

To a microwave tube add the substituted boronic acid (1.2 mmol), sodium bicarbonate (1.2 mmol), the heteroaryl halide (1.0 mmol), and tetrakis(triphenylphosphine)palladium(0) (0.02 mmol). Mix the materials thoroughly and add 50% aqueous DMSO (2 mL). Irradiate the reaction mixture in a microwave reactor set at 50 W, 90° C. for 10 min with external cooling. Dilute the reaction mixture with methanol (25 mL) and load the mixture onto a SCX column. Rinse the column with absolute methanol and elute with 2M ammonia in methanol. Combine fractions, condentrate under reduced pressure and chromatograph on silica gel using a gradient of neat ethyl acetate to 40% methanol/60% ethyl acetate. Further purify the isolated product via reverse-phase high-performance chromatography if needed.

The following compounds were prepared utilizing the General Suzuki Coupling Methods.

| Example | Product | Starting Material A | Starting Material B | Physical Data | Comments |
|---|---|---|---|---|---|
| 78 | 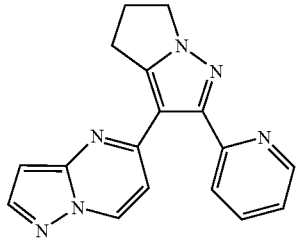<br>5-[2-(pyridin-2-yl)-5,6-dihydro-4H-pyrrolo[1,2-b]pyrazol-3-yl]-pyrazolo[1,5-a]pyrimidine | 5-iodo-pyrazolo[1,5-a]pyrimidine (Preparation 29) | Preparation 5 | TOF MS ES+ exact mass calculated for $C_{17}H_{15}N_6$ (p + H): m/z = 303.1358; Found: 303.1354, $^1$H NMR (400 MHz, DMSO-$d_6$) δ 8.83 (d, J=8 Hz, 1H), 8.51 (m, 1H), 8.10 (m, 1H), 7.87 (m, 1H), 7.78 (m, 1H), 7.36 (m, 1H), 6.89 (d, J=8 Hz, 1H), 6.52 (m, 1H), 4.20 (t, J=7 Hz, 2H), 3.13 (t, J=7 Hz, 2H), 2.62 (m, 2H). | (General Suzuki Coupling Method G) |
| 79 | 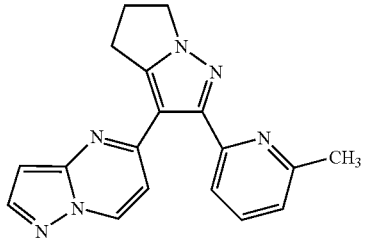<br>5-[2-(6-methyl-pyridin-2-yl)-5,6-dihydro-4H-pyrrolo[1,2-b]pyrazol-3-yl]-pyrazolo[1,5-a]pyrimidine | 5-iodo-pyrazolo[1,5-a]pyrimidine (Preparation 29) | Preparation 2 | TOF MS ES+ exact mass calculated for $C_{18}H_{17}N_6$ (p + H): m/z = 317.1515; Found: 317.1519. $^1$NMR (400 MHz, DMSO-$d_6$) δ 8.85 (d, J=8 Hz, 1H), 8.10 (m, 1H), 7.74 (m, 1H), 7.58 (d, J=8 Hz 1H), 7.22 (d, J=8 Hz, 1H), 7.01 (d, J=8 Hz, 1H), 6.53 (m, 1H), 4.19 (t, J=7 Hz, 2H), 3.13 (t, J=7 Hz, 2H), 2.61 (m, 2H), 2.38 (s, 3H). | Example 78 (General Suzuki Coupling Method G) |
| 80 | 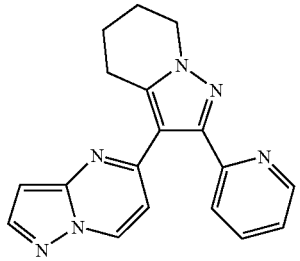<br>5-[2-(pyridin-2-yl)-4,5,6,7-tetrahydro-pyrazolo[1,5-a]pyridin-3-yl]-pyrazolo[1,5-a]pyrimidine | 5-iodo-pyrazolo[1,5-a]pyrimidine (Preparation 29) | 2-(pyridin-2-yl)-4,5,6,7-tetrahydro-pyrazolo[1,5-a]pyridine-3-boronic acid Preparation 5a | TOF MS ES+ exact mass calculated for $C_{18}H_{17}N_6$ (p + H): m/z = 317.1515; Found: 317.1517, $^1$H NMR (400 MHz, DMSO-$d_6$) δ 8.81 (d, J=8 Hz, 1H), 8.44 (m, 1H), 8.12 (m, 1H), 7.85 (m, 1H), 7.79 (m, 1H), 7.32 (m, 1H), 6.66 (d, J=8 Hz, 1H), 6.58 (m, 1H), 4.19 (t, J=6 Hz, 2H), 2.99 (t, J=6 Hz, 2H), 2.03 (m, 2H), 1.83 (m, 2H). | Example 78 (General Suzuki Coupling Method G) |

EXAMPLE 80a

Preparation of 8-(2-Pyridin-2-yl-5,6-dihydro-4H-pyrrolo[1,2-b]pyrazol-3-yl)-[1,6]naphthyridine

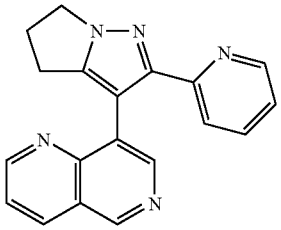

Add 8-bromo-[1,6]naphthyridine (Spec; 32 mg, 0.152 mmol), 2-(pyridin-2-yl)-5,6-dihydro-4H-pyrrolo[1,2-b]pyrazole-3-boronic acid (Preparation 5; 35 mg, 0.153 mmol), and potasium phosphate (97 mg, 0.458 mmol) to DMF (1 mL) and water (0.5 mL). De-gas the solution with argon and add tetrakis(triphenylphosphine)palladium(0) (88 mg, 0.076 mol). Heat the mixture at 60° C. for 18 h under an argon atmosphere. Cool the mixture to room temperature and dilute with water. Filter the mixture, and separate the filtrate. Extract the aqueous layer with dichloromethane. Dry the combined organic layers over sodium sulfate, filter, and concentrate. Purify the crude residue by column chromatography (12 g Redisep column, gradient dichloromethane through CMA over 40 min, 20 mL/min) to provide the title compound (31 mg, 64%) as an off white solid. Mp 180-184° C. MS (APCI) m/e=314 (M+1). $^1$H NMR (CDCl$_3$) δ 8.88 (dd, J=1.6, 4.2 Hz, 1H), 8.60 (d, J=4.7 Hz, 1H), 8.28 (d, J=8.5 Hz, 1H), 8.19 (d, J=8.9 Hz, 1H), 7.73-7.68 (m, 3H), 7.58 (dd, J=4.2, 8.5 Hz, 2H), 4.30 (t, J=7 Hz, 2H), 3.30 (t, J=7 Hz, 2H), 2.73 (p, J=7 Hz, 2H). HPLC: >99%, R$_t$=7.1 min.

EXAMPLE 81

Preparation of 3-[2-(Pyridin-2-yl)-5,6-dihydro-4H-pyrrolo[1,2-b]pyrazol-3-yl)-pyrazolo[1,5-a]pyrimidine

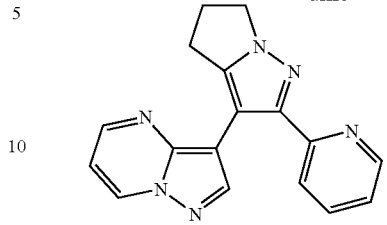

Weigh into a round bottom flask 3-bromopyrazolo[1,5-a]pyrimidine (Lynch et al. Can. J. Chem. 1975, 53, 119-122; 0.095 g, 0.48 mmol), 2-(pyridin-2-yl)-5,6-dihydro-4H-pyrrolo[1,2-b]pyrazole-3-boronic acid (Preparation 5; 0.10 g, 0.44 mmol), triphenylphosphine (Aldrich; 0.007 g, 0.027 mmol) and tris(dibenzylideneacetone)dipalladium(0) (Aldrich; 0.015 g, 0.016 mmol). Add p-dioxane (6 ml) and 2.0M aqueous potassium carbonate (2 mL). Stir and reflux under nitrogen for 6 h. Dilute with ethyl acetate, separate the organic layer, concentrate under reduced pressure, and chromatograph on flash silica using neat acetonitrile. Purify on a preparative reverse phase C-18 high-performance chromatography column using a gradient from 5% to 100% acetonitrile in 0.03% aqueous hydrochloric acid. Concentrate the pure fractions under reduced pressure, dissolve the residue in distilled water, and make basic by adding 1.0M aqueous sodium hydroxide. Extract with dichloromethane, dry the organic layer over anhydrous sodium sulfate, filter, and concentrate under reduced pressure to obtain 6 mg (4.5%) of the title compound as a yellow solid. TOF MS ES$^+$ exact mass calculated for $C_{17}H_{15}N_6$ (M+1): m/z=303.1358; Found: 303.1371. $^1$H NMR (400 MHz, CDCl$_3$) δ 8.66 (d, J=2 Hz, 1H), 8.64 (d, J=2 Hz, 1H), 8.41 (dd, J=4, 2 Hz, 1H), 8.31 (s, 1H), 7.70 (m, 2H), 7.21 (m, 1H), 6.79 (dd, J=7, 4 Hz, 1H), 4.30 (t, J=7 Hz, 2H), 3.10 (t, J=8 Hz, 2H), 2.68 (m, 2H).

EXAMPLE 82

The following compound was prepared using General Suzuki Coupling Method C (Preparation 32).

| Example | Product | Starting Material A | Starting Material B | Physical Data | Comments |
|---|---|---|---|---|---|
| 82 | 2-[2-(pyridin-2-yl)-5,6-dihydro-4H-pyrrolo[1,2-b]pyrazol-3-yl]-[1,5]naphthyridine | 2-bromo-1,5-naphthiridine (Czuba, Z. Recueil 1963, 82, 988-996). | Preparation 5 | Mp 189-191° C. MS (ESI) m/e 314 (M + 1). $^1$H NMR (CDCl$_3$) δ 8.89 (dd, J = 4, 1 Hz, 1H), 8.62 (br s, 1H), 8.28 (d, J = 8 Hz, 1H), 8.18 (d, J = 9 Hz, 1H), 7.75-7.56 (m, 4H), 7.25 (m, 1H), 4.29 (dd, J = 8, 7 Hz, 2H), 3.30 (dd, J = 8, 7 Hz, 2H), 2.78-2.71 (m, 2H). HPLC: 98.0%, R$_t$ = 14.4 min. TLC (SiO$_2$): R$_f$ 0.3 (2:1 methylene chloride/[80:18:2 chloroform/methanol/concentrated aqueous ammonium hydroxide]). | Preparation 32 (General Suzuki Coupling Method C) |

EXAMPLE 83

2-Chloro-7-[2-(6-methyl-pyridin-2-yl)-5,6-dihydro-4H-pyrrolo[1,2-b]pyrazol-3-yl]-quinoxaline

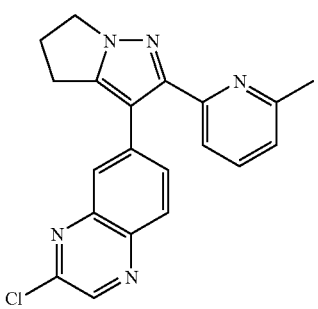

Dissolve 7-[2-(6-methylpyridin-2-yl)-5,6-dihydro-4H-pyrrolo[1,2-b]pyrazol-3-yl]-1H-quinoxalin-2-one (Example 55b; 200 mg, 0.6 mmol) in phosphorus oxychloride (20 mL). Reflux the solution for 30 min. Evaporate in vacuo. Dissolve the residue in 3:1 chloroform/isopropyl alcohol (100 mL) and wash the solution with 5% aqueous ammonia solution, brine and water. Dry the organic phase over sodium sulfate. Filter and evaporate the solvents in vacuo to give the target product as a yellow solid 180 mg (86%). MS (electrospray, m/z) 362.2 (M+1).

EXAMPLE 84

Dimethyl-(2-{7-[2-(6-methyl-pyridin-2-yl)-5,6-dihydro-4H-pyrrolo[1,2-b]pyrazol-3-yl]-quinoxalin-2-yloxy}-ethyl)-amine

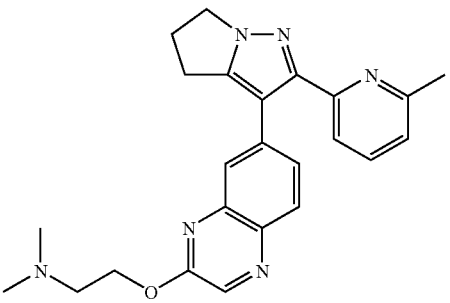

Combine of 2-dimethylaminoethanol (180 mg, 2 mmol) with of sodium hydride (48 mg, 2 mmol) in dry DMF (5 mL) at 0-5° C. Stir for 10 min, add 2-chloro-7-[2-(6-methyl-pyridin-2-yl)-5,6-dihydro-4H-pyrrolo[1,2-b]pyrazol-3-yl]-quinoxaline (Example 83; 60 mg, 0.17 mmol) in DMF (5 mL). Stir the reaction mixture for an additional 1 h. Dilute the mixture with dichloromethane. Wash the organic solution with brine, dry over sodium sulfate, filter and evaporate. Purify the crude product by column chromatography on silica gel to give target compound 35 mg (51%) as white solid. MS (electrospray, m/z) 414.2 (M+1). $^1$H NMR (CD$_2$Cl$_2$) δ 8.4 (s, 1H), 7.85 (d, 8.8 Hz, 1H), 7.81 (d, 1.6 Hz, 1H), 7.56 (t, 8.0 Hz, 1H), 7.51 (dd, 8.8 Hz, 1.6 Hz, 1H), 7.43 (d, 8.0 Hz, 1H), 7.09 (d, 8.0 Hz, 1H), 4.59 (t, 6 Hz, 2H), 4.27 (t, 7.2 Hz, 2H), 3.13 (t, 7.2 Hz, 2H), 2.80 (t, 6 Hz, 2H), 2.73 (m, 2H), 2.42 (s, 3H), 2.34 (s, 3H).

| Example | Product | Starting Material A | Starting Material B | Physical Data | Comments |
|---|---|---|---|---|---|
| 85 | dimethyl-(2-{7-[2-(6-methyl-pyridin-2-yl)-5,6-dihydro-4H-pyrrolo[1,2-b]pyrazol-3-yl]-quinoxalin-2-yloxy}-ethyl)-amine | 2-chloro-7-[2-(6-methyl-pyridin-2-yl)-5,6-dihydro-4H-pyrrolo[1,2-b]pyrazol-3-yl]-quinoxaline | 2-dimethylamino propanol | MS (electrospray, m/z) 429.2 (M + 1). | |

EXAMPLE 86

7-[2-(6-Methyl-pyridin-2-yl)-5,6-dihydro-4H-pyrrolo[1,2-b]pyrazol-3-yl]-quinoxaline-2-carboxylic acid amide

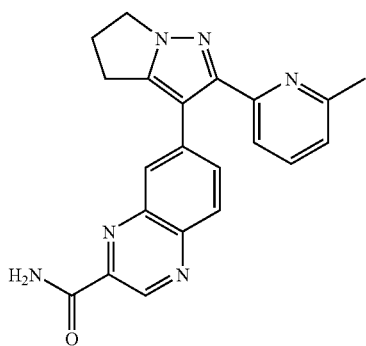

Reflux 7-[2-(6-methyl-pyridin-2-yl)-5,6-dihydro-4H-pyrrolo[1,2-b]pyrazol-3-yl]-1H-quinoxalin-2-one (Example 55b; 20 mg, 0.055 mmol,) in $POCl_3$ overnight. After removing $POCl_3$, treat the residue with $Zn(CN)_2$ (11.6 mg, 0.11 mmol) and $Pd(PPh_3)_4$ (3 mg, 0.003 mmol) in DMF (1 mL) at 100° C. for 20 min in microwave. Cool the solution to room temperature, dilute with chloroform/isopropyl alcohol and wash with brine. Dry the solution over sodium sulfate, filter, and evaporate the solvents to give a viscous mixture. Purify the crude product by column chromatography eluting with a gradient from dichloromethane to 10% methanol in dichloromethane to give the desired compound 12 mg (59%). MS (electrospray, m/z) 371.2 (M+1).

The compounds disclosed herein were tested by the following protocols for TGF-β inhibition, as described below in the protocol description.

TGF-β Receptor I Purification and In Vitro Kinase Reactions

For TGF-β Type I (RIT204D) Receptors

The 6x-HIS tagged cytoplasmic kinase domain of each receptor was expressed and purified from Sf9 insect cell lysates as briefly described below: Cell pellets after 48-72 h of infection were lysed in lysis buffer (LB: 50 mM Tris pH 7.5, 150 mM NaCl, 50 mM NaF, 0.5% NP40 with freshly added 20 mM β-mercaptoethanol, 10 mM imidazole, 1 mM PMSF, 1×EDTA-free Complete Protease Inhibitor (Boehringer Mannheim). Cell lysates were clarified by centrifugation and 0.45 uM filtered prior to purification by Ni/NTA affinity chromatography (Qiagen).

Chromatography Protocol

Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1×KB (50 mM Tris pH 7.5, 150 mM NaCl, 4 mM $MgCl_2$, 1 mM NaF, 2 mM β-mercaptoethanol), elute with a linear gradient of 1× KB containing 200 mM Imidazole. Both enzymes were approximately 90% pure and had autophosphorylation activity. Reactions: 170-200 nM enzyme in 1×KB, compound dilution series in 1×KB/16% DMSO (20 μM to 1 nM final concentration with 4% DMSO final concentration), reactions started by adding ATP mix (4 uM ATP/1 uCi $^{33}P$-γ-ATP final concentrations) in 1×KB.

Reactions were incubated at 30° C. for 1 h. Reactions were stopped and quantitated using standard TCA/BSA precipitation onto Millipore FB glass fiber filter plates and by liquid scintillation counting on a MicroBeta JET.

Representative compounds of the current invention which inhibit the TGF-β Type I (RIT204D) receptor kinase domain with $IC_{50}$ values <20 μM are listed in Table I.

TABLE I

| COMPOUND NAME |
|---|
| a. 3-(2-Phenyl-oxazol-5-yl)-2-(pyridin-2-yl)-5,6-dihydro-4H-pyrrolo[1,2-b]pyrazole |
| b. 4-[2-(Pyridin-2-yl)-5,6-dihydro-4H-pyrrolo[1,2-b]pyrazol-3-yl]-benzo[2,1,3]thiadiazole |
| c. 5-[2-(Pyridin-2-yl)-5,6-dihydro-4H-pyrrolo[1,2-b]pyrazol-3-yl]benzo[2,1,3]thiadiazole |
| d. 6-[2-(Pyridin-2-yl)-5,6-dihydro-4H-pyrrolo[1,2-b]pyrazol-3-yl]-quinoxaline |
| e. 2-[2-(Pyridin-2-yl)-5,6-dihydro-4H-pyrrolo[1,2-b]pyrazol-3-yl]-1H-imidazo[4,5-c]pyridine |
| f. 2-(Pyridin-2-yl)-3-(imidazo[1,2-a]pyridin-6-yl)-5,6-dihydro-4H-pyrrolo[1,2-b]pyrazole |
| g. 7-[2-(6-Methyl-pyridin-2-yl)-5,6-dihydro-4H-pyrrolo[1,2-b]pyrazol-3-yl]-isoquinoline |
| h. 3-(4-Fluoro-benzofuran-7-yl)-2-(pyridin-2-yl)-5,6-dihydro-4H-pyrrolo[1,2-b]pyrazole |
| i. 2-Methyl-5-[2-(pyridin-2-yl)-5,6-dihydro-4H-pyrrolo[1,2-b]pyrazol-3-yl]-benzothiazole |
| j. 2-Methyl-5-[2-(6-methyl-pyridin-2-yl)-5,6-dihydro-4H-pyrrolo[1,2-b]pyrazol-3-yl]-benzothiazole |
| k. 3-(4-Fluoro-benzofuran-7-yl)-2-(6-methyl-pyridin-2-yl)-5,6-dihydro-4H-pyrrolo[1,2-b]pyrazole |
| l. 7-[2-(Pyridin-2-yl)-5,6-dihydro-4H-pyrrolo[1,2-b]pyrazol-3-yl]-isoquinoline |
| m. 1-Methyl-5-[2-(pyridin-2-yl)-5,6-dihydro-4H-pyrrolo[1,2-b]pyrazol-3-yl]-1H-indole |
| n. 1-Methyl-5-[2-(pyridin-2-yl)-5,6-dihydro-4H-pyrrolo[1,2-b]pyrazol-3-yl]-1H indole |

TABLE I-continued

| COMPOUND NAME |
|---| o. 3-(Pyrazin-2-yl)-2-(pyridin-2-yl)-5,6-dihydro-4H-pyrrolo[1,2-b]pyrazole
p. 2-(6-Methyl-pyridin-2-yl)-(3-pyrazin-2-yl)-5,6-dihydro-4H-pyrrolo[1,2-b]pyrazole
q. 3-(2,3-Dihydro-benzofuran-5-yl)-2-(6-methyl-pyridin-2-yl)-5,6-dihydro-4H-pyrrolo[1,2-b]pyrazole
r. 3-(Furan-3-yl)-2-(6-methyl-pyridin-2-yl)-5,6-dihydro-4H-pyrrolo[1,2-b]pyrazole
s. 2-(6-Methyl-pyridin-2-yl)-3-(thiophen-3-yl)-5,6-dihydro-4H-pyrrolo[1,2-b]pyrazole
t. 3-(Benzofuran-5-yl)-2-(6-methyl-pyridin-2-yl)-5,6-dihydro-4H-pyrrolo[1,2-b]pyrazole
u. 6-[2-(Pyridin-2-yl)-5,6-dihydro-4H-pyrrolo[1,2-b]pyrazol-3-yl]-pyrazolo[1,5-a]pyrimidine
v. 3-(3,4-Dihydro-2H-benzo[b][1,4]dioxepin-7-yl)-2-(pyridin-2-yl)-5,6-dihydro-4H-pyrrolo[1,2-b]pyrazole
w. 3-Morpholin-4-ylmethyl-6-[2-(pyridin-2-yl)-5,6-dihydro-4H-pyrrolo[1,2-b]pyrazol-3-yl]-imidazo[1,2-a]pyridine
x. 1-Morpholin-4-yl-2-[6-(2-pyridin-2-yl-5,6-dihydro-4H-pyrrolo[1,2-b]pyrazol-3-yl)-imidazo[1,2-a]pyridin-3-yl]-ethanone
y. 6-[2-(Pyridin-2-yl)-5,6-dihydro-4H-pyrrolo[1,2-b]pyrazol-3-yl]-imidazo[1,2-a]pyridine-3-carboxylic acid
z. 6-[2-(Pyridin-2-yl)-4,5,6,7-tetrahydro-pyrazolo[1,5-a]pyridin-3-yl]-imidazo[1,2-a]pyridine
aa. 1-Morpholin-4-yl-2-[6-(2-pyridin-2-yl)-5,6-dihydro-4H-pyrrolo[1,2-b]pyrazol-3-yl)-imidazo[1,2-a]pyridin-2-yl]-ethanone
bb. 6-[2-(Pyridin-2-yl)-5,6-dihydro-4H-pyrrolo[1,2-b]pyrazol-3-yl]-imidazo[1,2-a]pyridine-3-carboxylic acid (2-dimethylamino-ethyl)-amide
cc. 6-[2-(6-Methyl-pyridin-2-yl)-5,6-dihydro-4H-pyrrolo[1,2-b]pyrazol-3-yl]-imidazo[1,2-a]pyridine-2-carboxylic acid ethyl ester
dd. 6-[2-(6-Methyl-pyridin-2-yl)-5,6-dihydro-4H-pyrrolo[1,2-b]pyrazol-3-yl]-imidazo[1,2-a]pyridine-2-carboxylic acid amide
ee. 8-Fluoro-6-[2-(pyridin-2-yl)-5,6-dihydro-4H-pyrrolo[1,2-b]pyrazol-3-yl]-imidazo[1,2-a]pyridine
ff. [6-[2-(Pyridin-2-yl)-5,6-dihydro-4H-pyrrolo[1,2-b]pyrazol-3-yl]-imidazo[1,2-a]pyridin-3-yl]-(1,1,3,3-tetramethyl-butyl)-amine
gg. -[6-[2-(Pyridin-2-yl)-5,6-dihydro-4H-pyrrolo[1,2-b]pyrazol-3-yl]-imidazo[1,2-a]pyridin-3-yl]-acetamide
hh. 6-[2-(Pyridin-2-yl)-5,6-dihydro-4H-pyrrolo[1,2-b]pyrazol-3-yl]-imidazo[1,2-a]pyridine-3-carboxylic Acid Amide
ii. 6-[2-(6-Methyl-pyridin-2-yl)-5,6-dihydro-4H-pyrrolo[1,2-b]pyrazol-3-yl]-imidazo[1,2-a]pyridine-2-carboxylic Acid (2-Dimethylamino-ethyl)-amide
jj. 6-[2-(6-Methyl-pyridin-2-yl)-5,6-dihydro-4H-pyrrolo[1,2-b]pyrazol-3-yl]-imidazo[1,2-a]pyridine-3-carboxylic Acid Amide
kk. 7-[2-(Pyridin-2-yl)-5,6-dihydro-4H-pyrrolo[1,2-b]pyrazol-3-yl]-imidazo[1,2-a]pyridine
ll. 3-(4-Chloro-phenyl)-6-[2-(6-methyl-pyridin-2-yl)-5,6-dihydro-4H-pyrrolo[1,2-b]pyrazol-3-yl]-imidazo[1,2-a]pyridine
mm. 5-[2-(6-Methyl-pyridin-2-yl)-5,6-dihydro-4H-pyrrolo[1,2-b]pyrazol-3-yl]-1H-benzoimidazole
nn. 1-Methyl-6-[2-(6-methyl-pyridin-2-yl)-5,6-dihydro-4H-pyrrolo[1,2-b]pyrazol-3-yl]-1H-benzoimidazole
oo. 1-Methyl-6-[2-(pyridin-2-yl)-5,6-dihydro-4H-pyrrolo[1,2-b]pyrazol-3-yl]-1H-benzoimidazole
pp. 1-Methyl-5-[2-(pyridin-2-yl)-5,6-dihydro-4H-pyrrolo[1,2-b]pyrazol-3-yl]-1H-benzoimidazole
qq. 1-Methyl-5-[2-(6-methyl-pyridin-2-yl)-5,6-dihydro-4H-pyrrolo[1,2-b]pyrazol-3-yl]-1H-benzoimidazole
rr. 5-[2-(6-Methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole
ss. 6-[2-(6-Methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole
tt. 5-[2-(Pyridin-2-yl)-5,6-dihydro-4H-pyrrolo[1,2-b]pyrazol-3-yl]-1-[3-(tetrahydro-pyran-2-yloxy)-propyl]-1H-benzoimidazole
uu. 6-[2-(Pyridin-2-yl)-5,6-dihydro-4H-pyrrolo[1,2-b]pyrazol-3-yl]-1-[3-(tetrahydro-pyran-2-yloxy)-propyl]-1H-benzoimidazole
vv. 2-{7-[2-(6-Methyl-pyridin-2-yl)-5,6-dihydro-4H-pyrrolo[1,2-b]pyrazol-3-yl]-pyrido[2,3-b]pyrazin-2-yloxy}-ethanol
ww. 7-[2-(6-Methyl-pyridin-2-yl)-5,6-dihydro-4H-pyrrolo[1,2-b]pyrazol-3-yl]-1H-quinoxalin-2-one
xx. 3-[2-(6-Methyl-pyridin-2-yl)-5,6-dihydro-4H-pyrrolo[1,2-b]pyrazol-3-yl][1,5]naphthyridine
yy. 3-[6-[2-(6-Methyl-pyridin-2-yl)-5,6-dihydro-4H-pyrrolo[1,2-b]pyrazol-3-yl]-benzoimidazol-1-yl]-propan-1-ol
zz. 3-[6-[2-(Pyridin-2-yl)-5,6-dihydro-4H-pyrrolo[1,2-b]pyrazol-3-yl]-benzoimidazol-1-yl]-propan-1-ol
aaa. Methanesulfonic Acid 3-[6-[2-(6-Methyl-pyridin-2-yl)-5,6-dihydro-4H-pyrrolo[1,2-b]pyrazol-3-yl]-benzoimidazol-1-yl]-propyl Ester

TABLE I-continued

| | COMPOUND NAME |
|---|---|
| bbb. | Methanesulfonic acid 3-[6-[2-(pyridin-2-yl)-5,6-dihydro-4H-pyrrolo[1,2-b]pyrazol-3-yl]-benzoimidazol-1-yl]-propyl ester |
| ccc. | Dimethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine |
| ddd. | Diethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine |
| eee. | 6-[2-(6-Methyl-pyridin-2-yl)-5,6-dihydro-4H-pyrrolo[1,2-b]pyrazol-3-yl]-1-(3-morpholin-4-yl-propyl)-1H-benzoimidazole |
| fff. | 6-[2-(6-Methyl-pyridin-2-yl)-5,6-dihydro-4H-pyrrolo[1,2-b]pyrazol-3-yl]-1-(3-pyrrolidin-1-yl-propyl)-1H-benzoimidazole |
| ggg. | 6-[2-(6-Methyl-pyridin-2-yl)-5,6-dihydro-4H-pyrrolo[1,2-b]pyrazol-3-yl]-1-(3-piperidin-1-yl-propyl)-1H-benzoimidazole |
| hhh. | 5-[2-(Pyridin-2-yl)-5,6-dihydro-4H-pyrrolo[1,2-b]pyrazol-3-yl]-1H-benzoimidazole |
| iii. | 6-[2-(6-Methyl-pyridin-2-yl)-5,6-dihydro-4H-pyrrolo[1,2-b]pyrazol-3-yl]-quinoxaline |
| jjj. | 2-[2-(Pyridin-2-yl)-5,6-dihydro-4H-pyrrolo[1,2-b]pyrazol-3-yl]-quinoxaline |
| kkk. | 2-[7-[2-(6-Methyl-pyridin-2-yl)-5,6-dihydro-4H-pyrrolo[1,2-b]pyrazol-3-yl]-quinoxalin-2-yloxy]-ethanol |
| lll. | 4-[2-(Pyridin-2-yl)-5,6-dihydro-4H-pyrrolo[1,2-b]pyrazol-3-yl]-[1,6]naphthyridine |
| mmm. | 6-[2-(6-Methyl-pyridin-2-yl)-5,6-dihydro-4H-pyrrolo[1,2-b]pyrazol-3-yl]-isoquinoline |
| nnn. | 6-[2-(Pyridin-2-yl)-5,6-dihydro-4H-pyrrolo[1,2-b]pyrazol-3-yl]-benzothiazole |
| ooo. | 5-[2-(Pyridin-2-yl)-5,6-dihydro-4H-pyrrolo[1,2-b]pyrazol-3-yl]-benzothiazol-2-ylamine |
| ppp. | 4-[2-(Pyridin-2-yl)-5,6-dihydro-4H-pyrrolo[1,2-b]pyrazol-3-yl]-1H-indole |
| qqq. | 3-[2-(Pyridin-2-yl)-5,6-dihydro-4H-pyrrolo[1,2-b]pyrazol-3-yl]-1H-indole |
| rrr. | 3-(2,3-Dihydro-benzofuran-5-yl)-2-(pyridin-2-yl)-5,6-dihydro-4H-pyrrolo[1,2-b]pyrazole |
| sss. | Acetic acid 5-[2-(6-methyl-pyridin-2-yl)-5,6-dihydro-4H-pyrrolo[1,2-b]pyrazol-3-yl]-benzofuran-3-yl ester |
| ttt. | 3-(5-Methoxy-benzofuran-3-yl)-2-(6-methyl-pyridin-2-yl)-5,6-dihydro-4H-pyrrolo[1,2-b]pyrazole |
| uuu. | 5-[2-(6-Methyl-pyridin-2-yl)-5,6-dihydro-4H-pyrrolo[1,2-b]pyrazol-3-yl]-benzofuran-2-carboxylic acid |
| vvv. | 3-(Benzofuran-2-yl)-2-(6-methyl-pyridin-2-yl)-5,6-dihydro-4H-pyrrolo[1,2-b]pyrazole |
| www. | 5-[2-(Pyridin-2-yl)-5,6-dihydro-4H-pyrrolo[1,2-b]pyrazol-3-yl]-pyrazolo[1,5-a]pyrimidine |
| xxx. | 5-[2-(6-Methyl-pyridin-2-yl)-5,6-dihydro-4H-pyrrolo[1,2-b]pyrazol-3-yl]-pyrazolo[1,5-a]pyrimidine |
| yyy. | 5-[2-(Pyridin-2-yl)-4,5,6,7-tetrahydro-pyrazolo[1,5-a]pyridin-3-yl]-pyrazolo[1,5-a]pyrimidine |
| zzz. | 8-[2-(Pyridin-2-yl)-5,6-dihydro-4H-pyrrolo[1,2-b]pyrazol-3-yl]-[1,6]naphthyridine |
| aaaa. | 3-[2-(Pyridin-2-yl)-5,6-dihydro-4H-pyrrolo[1,2-b]pyrazol-3-yl)-pyrazolo[1,5-a]pyrimidine |
| bbbb. | 2-[2-(Pyridin-2-yl)-5,6-dihydro-4H-pyrrolo[1,2-b]pyrazol-3-yl]-[1,5]naphthyridine |
| cccc. | Dimethyl-(2-{7-[2-(6-methyl-pyridin-2-yl)-5,6-dihydro-4H-pyrrolo[1,2-b]pyrazol-3-yl]-quinoxalin-2-yloxy}-ethyl)-amine |
| dddd. | Dimethyl-(2-{7-[2-(6-methyl-pyridin-2-yl)-5,6-dihydro-4H-pyrrolo[1,2-b]pyrazol-3-yl]-quinoxalin-2-yloxy}-propyl)-amine |
| eeee. | 7-[2-(6-Methyl-pyridin-2-yl)-5,6-dihydro-4H-pyrrolo[1,2-b]pyrazol-3-yl]-quinoxaline-2-carboxylic acid amide |

Conditions "characterized by enhanced TGF-β activity" include those wherein TGF-β synthesis is stimulated so that TGF-β is present at increased levels or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case "enhanced activity" refers to any condition wherein the biological activity of TGF-β is undesirably high, regardless of the cause.

A number of diseases have been associated with TGF-β1 over production. Inhibitors of TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery are associated with TGF-β overproduction.

Fibrotic diseases associated with TGF-β1 overproduction can be divided into chronic conditions such as fibrosis of the kidney, lung and liver and more acute conditions such as dermal scarring and restenosis (Chamberlain, J. Cardiovascular Drug Reviews, 19(4):329-344). Synthesis and secretion of TGF-β1 by tumor cells can also lead to immune suppression such as seen in patients with aggressive brain or breast tumors (Arteaga, et al. (1993) J. Clin. Invest. 92:2569-2576). The course of Leishmanial infection in mice is drastically altered by TGF-β1 (Barral-Netto, et al. (1992) Science 257: 545-547). TGF-β1 exacerbated the disease, whereas TGF-β1 antibodies halted the progression of the disease in genetically susceptible mice. Genetically resistant mice became susceptible to Leishmanial infection upon administration of TGF-β1.

The profound effects of TGF-β1 on extracellular matrix deposition have been reviewed (Rocco and Ziyadeh (1991) in Contemporary Issues in Nephrology v.23, Hormones, autocoids and the kidney. ed. Jay Stein, Churchill Livingston, N.Y. pp. 391-410; Roberts, et al. (1988) Rec. Prog. Hormone Res. 44:157-197) and include the stimulation of the synthesis and the inhibition of degradation of extracellular matrix components. Since the structure and filtration properties of the glomeralus are largely determined by the extracellular matrix composition of the mesangium and glomerular membrane, it is not surprising that TGF-β1 has profound effects on the kidney. The accumulation of mesangial matrix in proliferative glomeralonephritis (Border, et al. (1990) Kidney Int. 37:689-695) and diabetic nephropathy (Mauer, et al. (1984) J. Clin. Invest. 74:1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90:1814-1818). TGF-β1 is an important mediator in the genesis of renal fibrosis in a number of animal models (Phan, et al. (1990) Kidney Int. 37:426; Okuda, et al. (1990) J. Clin. Invest. 86:453). Suppression of experimentally induced glomerulonephritis in rats has been demonstrated by antiserum against TGF-β1 (Border, et al. (1990) Nature 346:371) and by an extracellular matrix protein, decorin, which can bind TGF-β1 (Border, et al. (1992) Nature 360:361-363).

Too much TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339:213-214). At the same time there was reduced angiogenesis, reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90:10759-10763). The TGF-β1 induced hyperplasia was not as extensive as that induced with PDGF-BB, but the extracellular matrix was more extensive with TGF-β1 transfectants. No extracellular matrix deposition was associated with FGF-1 (a secreted form of FGF) induced hyperplasia in this gene transfer pig model (Nabel (1993) Nature 362:844-846).

There are several types of cancer where TGF-β1 produced by the tumor may be deleterious. MATLyLu rat prostate cancer cells (Steiner and Barrack (1992) Mol. Endocrinol 6:15-25) and MCF-7 human breast cancer cells (Arteaga, et al. (1993) Cell Growth and Differ. 4:193-201) became more tumorigenic and metastatic after transfection with a vector expressing the mouse TGF-β1. TGF-β1 has been associated with angiogenesis, metastasis and poor prognosis in human prostate and advanced gastric cancer (Wikstrom, P., et al. (1998) Prostate 37: 19-29; Saito, H. et al. (1999) Cancer 86: 1455-1462). In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J. Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGF-β1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGF-β1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328:1592-1598). Patients with high circulating TGF-β before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at risk patients and 2) that reduction of TGF-β1 could decrease the morbidity and mortality of these common treatments for breast cancer patients.

Many malignant cells secrete transforming growth factory (TGF-β), a potent immunosuppressant, suggesting that TGF-β production may represent a significant tumor escape mechanism from host immunosurveillance. Establishment of a leukocyte sub-population with disrupted TGF-β signaling in the tumor-bearing host offers a potential means for immunotherapy of cancer. A transgenic animal model with disrupted TGF-β signaling in T cells is capable of eradicating a normally lethal TGF-β overexpressing lymphoma tumor, EL4 (Gorelik and Flavell, (2001) Nature Medicine 7(10): 1118-1122). Down regulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerized host. The immunosuppressive effects of TGF-β have also been implicated in a subpopulation of HIV patients with lower than predicted immune response based on their CD4/CD8 T cell counts (Garba, et al. J. Immunology (2002) 168: 2247-2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system overexpressing TGF-β in keratinocytes. While the transgenics were more resisitant to formation of benign skin lesions, the rate of metastatic conversion in the transgenics was dramatically increased (Cui, et al (1996) Cell 86(4):531-42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β on cell/cell and cell/stroma interactions result in a greater propensity for invasion and metastasis. Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities such as radiation therapy and chemotherapy induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate much of the cytotoxic effects of radiation therapy and chemotherapy and the treatment-dependent activation of TGF-β in the stroma may even be detrimental as it can make the microenvironment more conducive to tumor progression and contributes to tissue damage leading to fibrosis. The development of a TGF-β signal transduction inhibitors is likely to benefit the treatment of progressed cancer alone and in combination with other therapies.

The compounds are useful for the treatment of cancer and other disease states influenced by TGF-β by inhibiting TGF-β in a patient in need thereof by administering said compound(s) to said patient. TGF-β would also be useful against atherosclerosis (T. A. McCaffrey: TGF-βs and TGF-β Receptors in Atherosclerosis: Cytokine and Growth Factor Reviews 2000, 11, 103-114) and Alzeheimer's (Masliah, E.; Ho, G.; Wyss-Coray, T.: Functional Role of TGF-β in Alzheimer's Disease Microvascular Injury: Lessons from Trangenic Mice: Neurochemistry International 2001, 39, 393-400) diseases.

Pharmaceutical Compositions

The compositions of the present invention are therapeutically effective amounts of the TGF-β antagonists, noted above. The composition may be formulated with common excipients, diluents or carriers, and compressed into tablets, or formulated elixirs or solutions for convenient oral administration or administered by intramuscular intravenous routes. The compounds can be administered transdermally and maybe formulated as sustained release dosage forms and the like.

The method of treating a human patient according to the present invention includes administration of the TGF-β antagonists. The TGF-β antagonists are formulated into formulations which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations useful for separate administration of the TGF-β antagonists will normally consist of at least one compound selected from the compounds specified herein mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, for injection, and for oral ingestion.

We claim:

1. A compound selected from the group of:
a) 2-(Pyridin-2-yl)-3-(thiophen-2-yl)-5,6-dihydro-4H-pyrrolo[1,2-b]pyrazole;
b) 5-[2-(Pyridin-2-yl)-5,6-dihydro-4H-pyrrolo[1,2-b]pyrazol-3-yl]-1H-indole;
c) 3-(2-Phenyl-oxazol-5-yl)-2-(pyridin-2-yl)-5,6-dihydro-4H-pyrrolo[1,2-b]pyrazole;
d) 4-[2-(Pyridin-2-yl)-5,6-dihydro-4H-pyrrolo [1,2-b]pyrazol-3-yl]-benzo[2,1,3]thiadiazole;
e) 5-[2-(Pyridin-2-yl)-5,6-dihydro-4H-pyrrolo[1,2-b]pyrazol-3-yl]benzo[2,1,3]thiadiazole;
f) 6-[2-(Pyridin-2-yl)-5,6-dihydro-4H-pyrrolo[1,2-b]pyrazol-3-yl]-quinoxaline;
g) 5-[2-(Pyridin-2-yl)-5,6-dihydro-4H-pyrrolo[1,2-b]pyrazol-3-yl]-quinoxaline;
h) 2-[2-(Pyridin-2-yl)-5,6-dihydro-4H-pyrrolo [1,2-b]pyrazol-3-yl]-1H-imidazo[4,5-b]pyridine;
i) 2-[2-(Pyridin-2-yl)-5,6-dihydro-4H-pyrrolo[1,2-b]pyrazol-3-yl]-1H-imidazo[4,5-c]pyridine;
j) 2-[2-(Pyridin-2-yl)-5,6-dihydro-4H-pyrrolo[1,2-b]pyrazol-3-yl]-1H-benzoimidazole;
k) 2-[2-(Pyridin-2-yl)-5,6-dihydro-4H-pyrrolo[1,2-b]pyrazol-3-yl]-oxazolo[4,5-b]pyridine;
l) 2-Dimethylamino-N-[6-[2-(pyridin-2-yl)-5,6-dihydro-4H-pyrrolo[1,2-b]pyrazol-3-yl]-[1,8]naphthyridin-2-yl]-acetamide;
m) 4-[2-(Pyridin-2-yl)-5,6-dihydro-4H-pyrrolo[1,2-b]pyrazol-3-yl]-[1,8]naphthyridine;
n) 2-(Pyridin-2-yl)-3-(imidazo[1,2-a]pyridin-6-yl)-5,6-dihydro-4H-pyrrolo[1,2-b]pyrazole;
o) 7-[2-(6-Methyl-pyridin-2-yl)-5,6-dihydro-4H-pyrrolo[1,2-b]pyrazol-3-yl]-isoquinoline;
p) 4-[2-(Pyridin-2-yl)-5,6-dihydro-4H-pyrrolo[1,2-b]pyrazol-3-yl]-isoquinoline;
q) 3-(4-Fluoro-benzofuran-7-yl)-2-(pyridin-2-yl)-5,6-dihydro-4H-pyrrolo[1,2-b]pyrazole;
r) 2-Methyl-5-[2-(pyridin-2-yl)-5,6-dihydro-4H-pyrrolo[1,2-b]pyrazol-3-yl]-benzothiazole;
s) 2-Methyl-5-[2-(6-methyl-pyridin-2-yl)-5,6-dihydro-4H-pyrrolo[1,2-b]pyrazol-3-yl]-benzothiazole;
t) 3-(4-Fluoro-benzofuran-7-yl)-2-(6-methyl-pyridin-2-yl)-5,6-dihydro-4H-pyrrolo[1,2-b]pyrazole;
u) 7-[2-(Pyridin-2-yl)-5,6-dihydro-4H-pyrrolo[1,2-b]pyrazol-3-yl]-isoquinoline;
v) 1-Methyl-5-[2-(6-methyl-pyridin-2-yl)-5,6-dihydro-4H-pyrrolo[1,2-b]pyrazol-3-yl]-1H-indole;
w) 1-Methyl-5-[2-(pyridin-2-yl)-5,6-dihydro-4H-pyrrolo[1,2-b]pyrazol-3-yl]-1H indole;
x) 3-(Pyrazin-2-yl)-2-(pyridin-2-yl)-5,6-dihydro-4H-pyrrolo[1,2-b]pyrazole;
y) 2-(6-Methyl-pyridin-2-yl)-3-(pyrazin-2-yl)-5,6-dihydro-4H-pyrrolo[1,2-b]pyrazole;
z) 3-(2,3-Dihydro-benzofuran-5-yl)-2-(6-methyl-pyridin-2-yl)-5,6-dihydro-4H-pyrrolo[1,2-b]pyrazole;
aa) 3-(Furan-3-yl-2)-(6-methyl-pyridin-2-yl)-5,6-dihydro-4H-pyrrolo[1,2-b]pyrazole;
bb) 3-(Furan-3-yl)-2-(pyridin-2-yl)-5,6-dihydro-4H-pyrrolo[1,2-b]pyrazole;
cc) 2-(6-Methyl-pyridin-2-yl)-3-(thiophen-3-yl)-5,6-dihydro-4H-pyrrolo[1,2-b]pyrazole;
dd) 3-(Benzofuran-5-yl)-2-(6-methyl-pyridin-2-yl)-5,6-dihydro-4H-pyrrolo[1,2-b]pyrazole;
ee) 6-[2-(Pyridin-2-yl)-5,6-dihydro-4H-pyrrolo[1,2-b]pyrazol-3-yl]-pyrazolo[1,5-a]pyrimidine;
ff) 3-(3,4-Dihydro-2H-benzo[b][1,4]dioxepin-7-yl)-2-(pyridin-2-yl)-5,6-dihydro-4H-pyrrolo[1,2-b]pyrazole;
gg) 3-Morpholin-4-ylmethyl-6-[2-(pyridin-2-yl)-5,6-dihydro-4H-pyrrolo[1,2-b]pyrazol-3-yl]-imidazo[1,2-a]pyridine;
hh) 1-Morpholin-4-yl-2-[6-(2-pyridin-2-yl-5,6-dihydro-4H-pyrrolo[1,2-b]pyrazol-3-yl)-imidazo[1,2-a]pyridin-3-yl]-ethanone;
ii) 6-[2-(Pyridin-2-yl)-5,6-dihydro-4H-pyrrolo[1,2-b]pyrazol-3-yl]-imidazo[1,2-a]pyridine-3-carboxylic acid;
jj) 6-[2-(Pyridin-2-yl)-4,5,6,7-tetrahydro-pyrazolo[1,5-a]pyridin-3-yl]-imidazo[1,2-a]pyridine;
kk) 1-Morpholin-4-yl-2-[6-(2-pyridin-2-yl)-5,6-dihydro-4H-pyrrolo[1,2-b]pyrazol-3-yl)-imidazo[1,2-a]pyridin-2-yl]-ethanone;
ll) 6-[2-(Pyridin-2-yl)-5,6-dihydro-4H-pyrrolo[1,2-b]pyrazol-3-yl]-imidazo[1,2-a]pyridine-3-carboxylic acid (2-dimethylamino-ethyl)-amide;
mm) 6-[2-(6-Methyl-pyridin-2-yl)-5,6-dihydro-4H-pyrrolo[1,2-b]pyrazol-3-yl]-imidazo[1,2-a]pyridine-2-carboxylic acid ethyl ester;
nn) 6-[2-(6-Methyl-pyridin-2-yl)-5,6-dihydro-4H-pyrrolo[1,2-b]pyrazol-3-yl]-imidazo[1,2-a]pyridine-2-carboxylic acid amide;
oo) 8-Fluoro-6-[2-(pyridin-2-yl)-5,6-dihydro-4H-pyrrolo[1,2-b]pyrazol-3-yl]-imidazo[1,2-a]pyridine;
pp) [6-[2-(Pyridin-2-yl)-5,6-dihydro-4H-pyrrolo[1,2-b]pyrazol-3-yl]-imidazo[1,2-a]pyridin-3-yl]-(1,1,3,3-tetramethyl-butyl)-amine;
qq) N-[6-[2-(Pyridin-2-yl)-5,6-dihydro-4H-pyrrolo[1,2-b]pyrazol-3-yl]-imidazo[1,2-a]pyridin-3-yl]-acetamide;
rr) 6-[2-(Pyridin-2-yl)-5,6-dihydro-4H-pyrrolo[1,2-b]pyrazol-3-yl]-imidazo[1,2-a]pyridine-3-carboxylic Acid Amide;
ss) 6-[2-(6-Methyl-pyridin-2-yl)-5,6-dihydro-4H-pyrrolo[1,2-b]pyrazol-3-yl]-imidazo[1,2-a]pyridine-2-carboxylic Acid (2-Dimethylamino-ethyl)-amide;
tt) 6-[2-(6-Methyl-pyridin-2-yl)-5,6-dihydro-4H-pyrrolo[1,2-b]pyrazol-3-yl]-imidazo[1,2-a]pyridine-3-carboxylic Acid Amide;
uu) 7-[2-(Pyridin-2-yl)-5,6-dihydro-4H-pyrrolo[1,2-b]pyrazol-3-yl]-imidazo[1,2-a]pyridine;
vv) 3-(4-Chloro-phenyl)-6-[2-(6-methyl-pyridin-2-yl)-5,6-dihydro-4H-pyrrolo[1,2-b)pyrazol-3-yl]-imidazo[1,2-a]pyridine;
ww) 5-[2-(6-Methyl-pyridin-2-yl)-5,6-dihydro-4H-pyrrolo[1,2-b]pyrazol-3-yl]-1H-benzoimidazole;
xx) 1-Methyl-6-[2-(6-methyl-pyridin-2-yl)-5,6-dihydro-4H-pyrrolo[1,2-b]pyrazol-3-yl]-1H-benzoimidazole;
yy) 1-Methyl-6-[2-(pyridin-2-yl)-5,6-dihydro-4H-pyrrolo[1,2-b]pyrazol-3-yl]-1H-benzoimidazole;
zz) 1-Methyl-5-[2-(pyridin-2-yl)-5,6-dihydro-4H-pyrrolo[1,2-b]pyrazol-3-yl]-1H-benzoimidazole;
aaa) 1-Methyl-5-[2-(6-methyl-pyridin-2-yl)-5,6-dihydro-4H-pyrrolo[1,2-b]pyrazol-3-yl]-1H-benzoimidazole;
bbb) 5-[2-(6-Methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole;
ccc) 6-[2-(6-Methyl-pyridin-2-yl)-5,6-dihydro-4H-pyrrolo[1,2-b]pyrazol-3-yl]-1-[3-(tetrahydro-pyran-2-yloxy)-propyl]-1H-benzoimidazole;

ddd) 5-[2-(Pyridin-2-yl)-5,6-dihydro-4H-pyrrolo[1,2-b]pyrazol-3-yl]-1-[3-(tetrahydro-pyran-2-yloxy)-propyl]-1H-benzoimidazole;

eee) 6-[2-(Pyridin-2-yl)-5,6-dihydro-4H-pyrrolo[1,2-b]pyrazol-3-yl]-1-[3-(tetrahydro-pyran-2-yloxy)-propyl]-1H-benzoimidazole;

fff) 2-{7-[2-(6-Methyl-pyridin-2-yl)-5,6-dihydro-4H-pyrrolo[1,2-b]pyrazol-3-yl]-pyrido[2,3-b]pyrazin-2-yloxy}-ethanol (Ex. 55a)

ggg) 7-[2-(6-Methyl-pyridin-2-yl)-5,6-dihydro-4H-pyrrolo[1,2-b]pyrazol-3-yl]-1H-quinoxalin-2-one;

hhh) 3-[2-(6-Methyl-pyridin-2-yl)-5,6-dihydro-4H-pyrrolo[1,2-b]pyrazol-3-yl][1,5]naphthyridine (Ex. 55c)

iii) 3-[6-[2-(6-Methyl-pyridin-2-yl)-5,6-dihydro-4H-pyrrolo [1,2-b]pyrazol-3-yl]-benzoimidazol-1-yl]-propan-1-ol;

jjj) 3-[6-[2-(Pyridin-2-yl)-5,6-dihydro-4H-pyrrolo[1,2-b]pyrazol-3-yl]-benzoimidazol-1-yl]-propan-1-ol;

kkk) Methanesulfonic Acid 3-[6-[2-(6-Methyl-pyridin-2-yl)-5,6-dihydro-4H-pyrrolo[1,2-b]pyrazol-3-yl]-benzoimidazol-1-yl]-propyl Ester;

lll) Methanesulfonic acid 3-[6-[2-(pyridin-2-yl)-5,6-dihydro-4H-pyrrolo[1,2-b]pyrazol-3-yl]-benzoimidazol-1-yl]-propyl ester (Ex. 57b)

mmm) Dimethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine;

nnn) Diethyl-[3-[6-[2-(6-methyl-pyridin-2-yl)-5,6-dihydro-4H-pyrrolo[1,2-b]pyrazol-3-yl]-1H-benzoimidazol-1-yl]propyl]amine;

ooo) 6-[2-(6-Methyl-pyridin-2-yl)-5,6-dihydro-4H-pyrrolo[1,2-b]pyrazol-3-yl]-1-(3-morpholin-4-yl-propyl)-1H-benzoimidazole;

ppp) 6-[2-(6-Methyl-pyridin-2-yl)-5,6-dihydro-4H-pyrrolo[1,2-b]pyrazol-3-yl]-1-(3-pyrrolidin-1-yl-propyl)-1H-benzoimidazole;

qqq) 6-[2-(6-Methyl-pyridin-2-yl)-5,6-dihydro-4H-pyrrolo[1,2-b]pyrazol-3-yl]-1-(3-piperidin-1-yl-propyl)-1H-benzoimidazole;

rrr) 5-[2-(Pyridin-2-yl)-5,6-dihydro-4H-pyrrolo[1,2-b]pyrazol-3-yl]-1H-benzoimidazole;

sss) 6-[2-(6-Methyl-pyridin-2-yl)-5,6-dihydro-4H-pyrrolo[1,2-b]pyrazol-3-yl]-quinoxaline;

ttt) 2-[2-(Pyridin-2-yl)-5,6-dihydro-4H-pyrrolo[1,2-b]pyrazol-3-yl]-quinoxaline;

uuu) 2-[7-[2-(6-Methyl-pyridin-2-yl)-5,6-dihydro-4H-pyrrolo[1,2-b]pyrazol-3-yl]-quinoxalin-2-yloxy]-ethanol;

vvv) 4-[2-(Pyridin-2-yl)-5,6-dihydro-4H-pyrrolo[1,2-b]pyrazol-3-yl]-[1,6]naphthyridine;

www) 6-[2-(6-Methyl-pyridin-2-yl)-5,6-dihydro-4H-pyrrolo[1,2-b]pyrazol-3-yl]-isoquinoline;

xxx) 6-[2-(Pyridin-2-yl)-5,6-dihydro-4H-pyrrolo[1,2-b]pyrazol-3-yl]-benzothiazole;

yyy) 2-[2-(Pyridin-2-yl)-5,6-dihydro-4H-pyrrolo[1,2-b]pyrazol-3-yl]-benzothiazole;

zzz) 5-[2-(Pyridin-2-yl)-5,6-dihydro-4H-pyrrolo[1,2-b]pyrazol-3-yl]-benzothiazol-2-ylamine;

aaaa) 4-[2-(Pyridin-2-yl)-5,6-dihydro-4H-pyrrolo[1,2-b]pyrazol-3-yl]-1H-indole;

bbbb) 3-[2-(Pyridin-2-yl)-5,6-dihydro-4H-pyrrolo[1,2-b]pyrazol-3-yl]-1H-indole;

cccc) 3-(2,3-Dihydro-benzofuran-5-yl)-2-(pyridin-2-yl)-5,6-dihydro-4H-pyrrolo[1,2-b]pyrazole;

dddd) Acetic acid 5-[2-(6-methyl-pyridin-2-yl)-5,6-dihydro-4H-pyrrolo[1,2-b]pyrazol-3-yl]-benzofuran-3-yl ester;

eeee) 3-(5-Methoxy-benzofuran-3-yl)-2-(6-methyl-pyridin-2-yl)-5,6-dihydro-4H-pyrrolo[1,2-b]pyrazole;

ffff) 5-[2-(6-Methyl-pyridin-2-yl)-5,6-dihydro-4H-pyrrolo[1,2-b]pyrazol-3-yl]-benzofuran-2-carboxylic acid;

gggg) 3-(Benzofuran-2-yl)-2-(6-methyl-pyridin-2-yl)-5,6-dihydro-4H-pyrrolo[1,2-b]pyrazole;

hhhh) 5-[2-(Pyridin-2-yl)-5,6-dihydro-4H-pyrrolo[1,2-b]pyrazol-3-yl]-pyrazolo[1,5-a]pyrimidine;

iiii) 5-[2-(6-Methyl-pyridin-2-yl)-5,6-dihydro-4H-pyrrolo[1,2-b]pyrazol-3-yl]-pyrazolo[1,5-a]pyrimidine;

jjjj) 5-[2-(Pyridin-2-yl)-4,5,6,7-tetrahydro-pyrazolo[1,5-a]pyridin-3-yl]-pyrazolo[1,5-a]pyrimidine;

kkkk) 8-(2-Pyridin-2-yl-5,6-dihydro-4H-pyrrolo[1,2-b]pyrazol-3-yl)-[1,6]naphthyridine;

llll) 3-[2-(Pyridin-2-yl)-5,6-dihydro-4H-pyrrolo[1,2-b]pyrazol-3-yl)-pyrazolo[1,5-a]pyrimidine;

mmmm) 2-[2-(Pyridin-2-yl)-5,6-dihydro-4H-pyrrolo[1,2-b]pyrazol-3-yl]-[1,5]naphthyridine;

nnnn) 2-Chloro-7-[2-(6-methyl-pyridin-2-yl)-5,6-dihydro-4H-pyrrolo[1,2-b]pyrazol-3-yl]-quinoxaline;

oooo) Dimethyl-(2-{7-[2-(6-methyl-pyridin-2-yl)-5,6-dihydro-4H-pyrrolo[1,2-b]pyrazol-3-yl]-quinoxalin-2-yloxy}-ethyl)-amine;

pppp) Dimethyl-(2-{7-[2-(6-methyl-pyridin-2-yl)-5,6-dihydro-4H-pyrrolo[1,2-b]pyrazol-3-yl]-quinoxalin-2-yloxy}-propyl)-amine;

qqqq) 7-[2-(6-Methyl-pyridin-2-yl)-5,6-dihydro-4H-pyrrolo[1,2-b]pyrazol-3-yl]-quinoxaline-2-carboxylic acid amide;

or a pharmaceutically acceptable salt thereof.

\* \* \* \* \*